(12) United States Patent
Shatalov et al.

(10) Patent No.: US 10,383,964 B2
(45) Date of Patent: Aug. 20, 2019

(54) STORAGE DEVICE INCLUDING ULTRAVIOLET ILLUMINATION

(71) Applicant: Sensor Electronic Technology, Inc., Columbia, SC (US)

(72) Inventors: Maxim S. Shatalov, Columbia, SC (US); Timothy James Bettles, Irmo, SC (US); Alexander Dobrinsky, Silver Spring, MD (US); Remigijus Gaska, Columbia, SC (US); Michael Shur, Latham, NY (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 15/700,533

(22) Filed: Sep. 11, 2017

(65) Prior Publication Data

US 2017/0368215 A1     Dec. 28, 2017

Related U.S. Application Data

(63) Continuation-in-part of application No. 15/388,394, filed on Dec. 22, 2016, which is a continuation-in-part of application No. 14/629,508, filed on Feb. 24, 2015, now Pat. No. 9,919,068, which is a continuation-in-part of application No. 14/012,682, filed on Aug. 28, 2013, now Pat. No. 9,034,271.

(Continued)

(51) Int. Cl.
*A61L 2/10* (2006.01)
*F25D 17/04* (2006.01)
(Continued)

(52) U.S. Cl.
CPC .............. *A61L 2/10* (2013.01); *F25D 17/042* (2013.01); *G01G 19/52* (2013.01); *G01N 27/121* (2013.01);
(Continued)

(58) Field of Classification Search
None
See application file for complete search history.

(56) References Cited

U.S. PATENT DOCUMENTS 2,482,507 A    9/1949  Rentschler et al.
3,817,703 A    6/1974  Atwood
(Continued)

FOREIGN PATENT DOCUMENTS

CN    1269246 A    10/2000
CN    2488020 Y     4/2002
(Continued)

OTHER PUBLICATIONS

Cox, A., U.S. Appl. No. 14/012,637, Notice of Allowance, dated Jan. 19, 2018, 43 pages.

(Continued)

*Primary Examiner* — Kishor Mayekar
(74) *Attorney, Agent, or Firm* — LaBatt, LLC

(57) ABSTRACT

Ultraviolet radiation is directed within an area. Items located within the area and/or one or more conditions of the area are monitored over a period of time. Based on the monitoring, ultraviolet radiation sources are controlled by adjusting a direction, an intensity, a pattern, and/or a spectral power of the ultraviolet radiation generated by the ultraviolet radiation source. Adjustments to the ultraviolet radiation source(s) can correspond to one of a plurality of selectable operating configurations including a storage life preservation operating configuration, a disinfection operating configuration, and an ethylene decomposition operating configuration.

20 Claims, 39 Drawing Sheets

Related U.S. Application Data

(60) Provisional application No. 62/385,581, filed on Sep. 9, 2016, provisional application No. 62/042,737, filed on Aug. 27, 2014, provisional application No. 61/943,915, filed on Feb. 24, 2014, provisional application No. 61/694,229, filed on Aug. 28, 2012, provisional application No. 61/694,232, filed on Aug. 28, 2012.

(51) Int. Cl.
  *G01N 27/12* (2006.01)
  *G01G 19/52* (2006.01)
  *H04N 5/33* (2006.01)
  *H04N 7/18* (2006.01)

(52) U.S. Cl.
  CPC ............ *H04N 5/332* (2013.01); *H04N 7/183* (2013.01); *A61L 2202/14* (2013.01); *A61L 2202/21* (2013.01); *F25D 2317/0417* (2013.01)

(56) References Cited

U.S. PATENT DOCUMENTS

| | | |
|---|---|---|
| 4,736,416 A | 4/1988 | Weinert |
| 4,857,277 A | 8/1989 | Broomfield |
| 4,867,052 A | 9/1989 | Cipelletti |
| 5,078,971 A | 1/1992 | Matuda et al. |
| 5,117,642 A | 6/1992 | Nakanishi et al. |
| 5,136,170 A | 8/1992 | Gellert |
| 5,230,220 A | 7/1993 | Kang et al. |
| 5,364,645 A | 11/1994 | Lagunas-Solar et al. |
| 5,454,944 A | 10/1995 | Clack |
| 5,768,898 A | 6/1998 | Seok et al. |
| 5,836,669 A | 11/1998 | Hed |
| 5,865,959 A | 2/1999 | Meinzer et al. |
| 5,889,684 A | 3/1999 | Ben-David et al. |
| 5,901,564 A | 5/1999 | Comeau, II |
| 5,919,422 A | 7/1999 | Yamanaka et al. |
| 6,165,526 A | 12/2000 | Newman |
| 6,182,453 B1 | 2/2001 | Forsberg |
| 6,312,608 B1 | 11/2001 | Buckner |
| 6,447,721 B1 | 9/2002 | Horton, III et al. |
| 6,471,136 B1 | 10/2002 | Chatterjee et al. |
| 6,477,853 B1 | 11/2002 | Khorram |
| 6,524,529 B1 | 2/2003 | Horton, III |
| 6,565,803 B1 | 5/2003 | Bolton et al. |
| 6,574,984 B1 | 6/2003 | McCrea et al. |
| 6,576,188 B1 | 6/2003 | Rose et al. |
| 6,579,495 B1 | 6/2003 | Maiden |
| 6,592,816 B1 | 7/2003 | Ebel et al. |
| 6,673,137 B1 | 1/2004 | Wen |
| 6,735,479 B2 | 5/2004 | Fabian et al. |
| 6,818,177 B1 | 11/2004 | Turcotte |
| 6,878,761 B2 | 4/2005 | Gugumus |
| 7,026,018 B2 | 4/2006 | Kranovich |
| 7,160,370 B2 | 1/2007 | Baca et al. |
| 7,296,422 B2 | 11/2007 | Strohm et al. |
| 7,323,065 B2 | 1/2008 | Fencl et al. |
| 7,401,469 B2 | 7/2008 | Joshi et al. |
| 7,452,561 B2 | 11/2008 | Newman |
| 7,634,996 B2 | 12/2009 | Gaska et al. |
| 7,645,381 B2 | 1/2010 | Oranski et al. |
| 7,754,156 B2 | 7/2010 | Hyde et al. |
| 7,897,104 B2 | 3/2011 | Kwon |
| 8,062,589 B2 | 11/2011 | Naarup |
| 8,114,342 B2 | 2/2012 | Jung et al. |
| 8,178,042 B2 | 5/2012 | Jung et al. |
| 8,277,734 B2 | 10/2012 | Koudymov et al. |
| 8,384,047 B2 | 2/2013 | Shur et al. |
| 8,828,315 B2 | 9/2014 | Ryska et al. |
| 9,006,680 B2 | 4/2015 | Bettles et al. |
| 9,042,967 B2 | 5/2015 | Dacosta et al. |
| 9,061,082 B2 | 6/2015 | Gaska et al. |
| 9,138,499 B2 | 9/2015 | Bettles et al. |
| 9,179,703 B2 | 11/2015 | Shur et al. |
| 9,572,903 B2 | 2/2017 | Dobrinsky et al. |
| 9,603,960 B2 | 3/2017 | Dobrinsky et al. |
| 9,687,577 B2 | 6/2017 | Dobrinsky et al. |
| 9,707,307 B2 | 7/2017 | Shur et al. |
| 9,878,061 B2 | 1/2018 | Shur et al. |
| 2002/0063954 A1 | 5/2002 | Horton, III |
| 2002/0074559 A1 | 6/2002 | Dowling et al. |
| 2002/0122743 A1 | 9/2002 | Huang |
| 2002/0176809 A1 | 11/2002 | Siess |
| 2003/0019222 A1 | 1/2003 | Takahashi et al. |
| 2003/0019505 A1 | 1/2003 | Scheir et al. |
| 2003/0164754 A1 | 9/2003 | Roseen |
| 2003/0194692 A1 | 10/2003 | Purdum |
| 2004/0018125 A1 | 1/2004 | Yang et al. |
| 2004/0210099 A1 | 10/2004 | Shiratori |
| 2005/0165499 A1 | 7/2005 | Stein |
| 2005/0178977 A1 | 8/2005 | Koenck et al. |
| 2005/0186124 A1 | 8/2005 | Fink et al. |
| 2005/0217282 A1 | 10/2005 | Strohm et al. |
| 2005/0257827 A1 | 11/2005 | Gaudiana et al. |
| 2005/0274965 A1 | 12/2005 | Phillips et al. |
| 2006/0091310 A1 | 5/2006 | Furry |
| 2006/0130498 A1 | 6/2006 | Joshi et al. |
| 2006/0147339 A1 | 7/2006 | Hunter et al. |
| 2006/0163169 A1 | 7/2006 | Eckhardt et al. |
| 2006/0216193 A1 | 9/2006 | Johnson et al. |
| 2006/0237687 A1 | 10/2006 | Yue et al. |
| 2007/0051901 A1 | 3/2007 | Hopaluk et al. |
| 2007/0104841 A1 | 5/2007 | Min et al. |
| 2007/0164232 A1 | 7/2007 | Rolleri et al. |
| 2007/0172560 A1 | 7/2007 | Mirtsching et al. |
| 2007/0172661 A1 | 7/2007 | Fechner et al. |
| 2007/0196235 A1 | 8/2007 | Shur et al. |
| 2007/0205382 A1 | 9/2007 | Gaska et al. |
| 2007/0248487 A1 | 10/2007 | Kay et al. |
| 2007/0295203 A1 | 12/2007 | Shekarriz et al. |
| 2008/0061005 A1 | 3/2008 | Hopaluk et al. |
| 2008/0067418 A1* | 3/2008 | Ross ........................ A61L 2/10 250/455.11 |
| 2008/0168788 A1 | 7/2008 | Hurlebaus et al. |
| 2008/0168790 A1 | 7/2008 | Hurlebaus et al. |
| 2008/0213129 A1 | 9/2008 | van der Pol et al. |
| 2008/0286146 A1 | 11/2008 | Schroll et al. |
| 2008/0295033 A1 | 11/2008 | Lee et al. |
| 2008/0307818 A1 | 12/2008 | Min et al. |
| 2009/0110933 A1 | 4/2009 | Hyde et al. |
| 2009/0185960 A1 | 7/2009 | Busujima |
| 2009/0228155 A1 | 9/2009 | Slifkin et al. |
| 2009/0229287 A1 | 9/2009 | Prentner |
| 2009/0280035 A1 | 11/2009 | Koudymov et al. |
| 2010/0065632 A1 | 3/2010 | Babcock et al. |
| 2010/0097013 A1 | 4/2010 | Inskeep |
| 2010/0101432 A1 | 4/2010 | Biotti et al. |
| 2010/0227031 A1 | 9/2010 | Vasilenko |
| 2010/0296971 A1 | 11/2010 | Gaska et al. |
| 2010/0307973 A1 | 12/2010 | Grcevic |
| 2011/0030560 A1 | 2/2011 | Bohlen et al. |
| 2011/0044848 A1 | 2/2011 | Wright |
| 2011/0147617 A1 | 6/2011 | Shur et al. |
| 2011/0163046 A1 | 7/2011 | Neal et al. |
| 2011/0228534 A1 | 9/2011 | Zhang et al. |
| 2011/0297241 A1 | 12/2011 | Biotti et al. |
| 2011/0306262 A1 | 12/2011 | Aprin |
| 2012/0011874 A1 | 1/2012 | Conradt et al. |
| 2012/0017628 A1 | 1/2012 | Okabe et al. |
| 2012/0025104 A1 | 2/2012 | Park et al. |
| 2012/0051030 A1 | 3/2012 | Johnson |
| 2012/0085116 A1 | 4/2012 | Maeng et al. |
| 2012/0104021 A1 | 5/2012 | Cur et al. |
| 2012/0126134 A1 | 5/2012 | Deal et al. |
| 2013/0015753 A1* | 1/2013 | Son ........................ F25D 29/00 312/405 |
| 2013/0048545 A1 | 2/2013 | Shatalov et al. |
| 2013/0270445 A1* | 10/2013 | Gaska ........................ A61L 2/10 250/372 |
| 2013/0337121 A1 | 12/2013 | Sugano et al. |
| 2014/0042012 A1 | 2/2014 | Clement et al. |
| 2014/0060094 A1 | 3/2014 | Shur et al. |

(56) References Cited

U.S. PATENT DOCUMENTS

| | | | |
|---|---|---|---|
| 2014/0060095 A1 | 3/2014 | Shur et al. | |
| 2014/0060096 A1 | 3/2014 | Shur et al. | |
| 2014/0060104 A1 | 3/2014 | Shur et al. | |
| 2014/0102127 A1 | 4/2014 | Yum et al. | |
| 2014/0202962 A1 | 7/2014 | Bilenko et al. | |
| 2014/0209928 A1 | 7/2014 | Teng et al. | |
| 2015/0008167 A1 | 1/2015 | Shturm et al. | |
| 2015/0069270 A1 | 3/2015 | Shur et al. | |
| 2015/0161909 A1 | 6/2015 | Won et al. | |
| 2015/0165079 A1 | 6/2015 | Shur et al. | |
| 2015/0217011 A1 | 8/2015 | Betties et al. | |
| 2015/0297767 A1 | 10/2015 | Gaska et al. | |
| 2015/0336810 A1 | 11/2015 | Smetona et al. | |
| 2016/0000953 A1 | 1/2016 | Bettles et al. | |
| 2016/0058020 A1 | 3/2016 | Shur et al. | |
| 2016/0114186 A1 | 4/2016 | Dobrinsky et al. | |
| 2016/0128526 A1 | 5/2016 | Dobrinsky et al. | |
| 2016/0324996 A1 | 11/2016 | Bilenko et al. | |
| 2017/0057842 A1 | 3/2017 | Dobrinsky et al. | |
| 2017/0071332 A1* | 3/2017 | Herring .................. | A47B 21/02 |
| 2017/0100494 A1 | 4/2017 | Dobrinsky et al. | |
| 2017/0100495 A1 | 4/2017 | Shur et al. | |
| 2017/0100496 A1 | 4/2017 | Shur et al. | |
| 2017/0157276 A1 | 6/2017 | Dobrinsky et al. | |
| 2017/0189711 A1 | 7/2017 | Shur et al. | |
| 2017/0197002 A1 | 7/2017 | Dobrinsky et al. | |
| 2017/0245527 A1 | 8/2017 | Dobrinsky et al. | |
| 2017/0245616 A1 | 8/2017 | Lakios et al. | |
| 2017/0281812 A1 | 10/2017 | Dobrinsky et al. | |
| 2018/0243458 A1 | 8/2018 | Shatalov et al. | |

FOREIGN PATENT DOCUMENTS

| | | | |
|---|---|---|---|
| CN | 1580626 A | | 2/2005 |
| CN | 101171938 A | | 5/2008 |
| CN | 101322000 A | | 12/2008 |
| CN | 102389579 A | * | 3/2012 |
| CN | 202236462 U | | 5/2012 |
| CN | 102564003 A | | 7/2012 |
| CN | 103550799 A | | 2/2014 |
| EP | 1038536 B1 | | 6/2005 |
| JP | 2002204653 A | | 7/2002 |
| KR | 1020090074966 A | | 7/2009 |
| KR | 1020110057773 A | | 6/2011 |
| KR | 1020120011458 A | | 2/2012 |
| WO | 2013096243 A1 | | 6/2013 |
| WO | 2014036137 A1 | | 3/2014 |

OTHER PUBLICATIONS

Mayekar, K., U.S. Appl. No. 15/388,394, Office Action1, dated Mar. 30, 2018, 81 pages.
Bialka et al., "Decontamination of *Escherichia coli* O157:H7 and *Salmonella enterica* on Blueberries Using Ozone and Pulsed UV-Light," Journal of Food Science, 2007, 7 pages, vol. 72, No. 9.
Bialka et al., "Modeling the inactivation of *Escherichia coli* O157:H7 and *Salmonella enterica* on raspberries and strawberries resulting from exposure to ozone or pulsed UV-light," Journal of Food Engineering, 2008, 6 pages, vol. 85.
Bialka et al., "Pulsed UV-light Penetration of Characterization and the Inactivation of *Escherichia coli* K12 in Solid Model Systems," Abstract, American Society of Agricultural and Biological Engineers, 2013, 1 page.
Bialka et al., "Efficacy of Pulsed UV-Light for the Decontamination of *Escherichia coli* O157:H7 and *Salmonella* spp. on Raspberries and Strawberries," Journal of Food Science, 2008, 7 pages, vol. 73, No. 5.
Chang et al., "Removal of Ethylene and Secondary Organic Aerosols Using UV-C 254+185 with TiO2 Catalyst," Aerosol and Air Quality Research, 2013, 9 pages.
Cheba et al., "Inactivation of *E Coli* cell viability and DNA Photo-breakage by Pulsed Nitrogen Laser Radiation," American Institute of Physics, 2005, 5 pages.
Chisari et al., "Improving the quality of fresh-cut melon through inactivation of degradative oxidase and pectinase enzymatic activities by UV-C treatment," Institute of Food Science and Technology, 2011, 6 pages.
Demirci et al., "Disinfection of water by flow-through a Pulsed UV Light Sterilization System," Abstract, Ultrapure Water Journal, 2000, 1 page.
Demirci et al., "Pulsed Ultraviolet Light," Sage Publications, 2008, 5 pages.
Hillegas et al., "Inactivation of Clostridium sporogenes in Clover Honey by Pulsed UV-light Treatment," Abstract, American Society of Agricultural and Biological Engineers, 2013, 1 page.
Jun et al., "Pulsed UV-light treatment of corn meal for inactivation of Aspergillus niger spores," International Journal of Food Science and Technology, 2003, 6 pages.
Kennedy et al., "An investigation of the thermal inactivation of *Staphylococcus aurues* and the potential for increased thermotolerance as a result of chilled storage," Journal of Applied Microbiology, 2005, 7 pages.
Krishnamurthy et al., "Inactivation of *Staphylococcus aureus* by Pulsed UV-Light Sterilization," Abstract, Journal of Food Protection, 2004, 1 page.
Krishnamurthy et al., "Inactivation of *Staphylococcus aureus* in Milk and Milk Foam by Pulsed UV-Light Treatment and Su+R170rFace Response Modeling," Abstract, American Society of Agriculutural and Biological Engineers, 2013, 1 page.
Krishnamurthy et al., "Inactivation of *Staphylococcus aureus* in Milk Using Flow-Through Pulsed UV-Light Treatment System," Journal of Food Science, 2007, 7 pages, vol. 72, No. 7.
Krishnamurthy et al., "Microscopic and Spectroscopic Evaluation of Inactivation of *Staphylococcus aureus* by Pulsed UV Light and Infrared Heating," Food Bioprocess Technology, 2010, 12 pages.
Ozer et al., "Inactivation of *Escherichia coli* O157:H7 and Listeria monocytogenes inoculated on raw salmon fillets by pulsed UV-light treatment," International Journal of Food Science and Technology, 2006, 7 pages.
Sharma et al., "Inactivation of *Escherichia coli* O157:H7 on Inoculated Alfalfa Seed with Pulsed Ultraviolet Light and Response Surface Modeling," Food Microbiology and Safety, 2003, 6 pages.
Zhang et al., "Nonthermal Processing Technologies for Food," Chapters 18 and 19, IFT Press, 2011, 21 pages.
Mayekar, K., U.S. Appl. No. 14/012,682, Non-Final Rejection, dated Sep. 24, 2014, 20 pages.
Mayekar, K., U.S. Appl. No. 14/012,682, Notice of Allowance, dated Jan. 22, 2015, 16 pages.
Mayekar, K., U.S. Appl. No. 14/629,508, Non-Final Rejection, dated Jun. 13, 2017, 74 pages.
Martin, E., U.S. Appl. No. 14/012,667, Notice of Allowance, dated Jun. 16, 2017, 25 pages.
Martin, E., U.S. Appl. No. 14/012,667, Final Rejection2, dated Nov. 30, 2016, 25 pages.
Martin, E., U.S. Appl. No. 14/012,667, Non-Final Rejection, dated Dec. 3, 2015, 73 pages.
Martin, E., U.S. Appl. No. 14/012,667, Final Rejection 1, dated Apr. 1, 2016, 15 pages.
Martin, E., U.S. Appl. No. 14/012,667, Non-Final Rejection2, dated Jun. 28, 2016, 20 pages.
Martin, E., U.S. Appl. No. 14/541,245, Notice of Allowance, dated Apr. 3, 2017, 18 pages.
Martin, E., U.S. Appl. No. 14/541,245, Final Rejection 1, dated Nov. 28, 2016, 23 pages.
Martin, E., U.S. Appl. No. 14/541,245, Non-Final Rejection 1, dated Jun. 17, 2016, 60 pages.
Mendoza-Wilkenfe, E., U.S. Appl. No. 14/012,652, Notice of Allowance, dated Mar. 10, 2017, 37 pages.
Mendoza-Wilkenfe, E., U.S. Appl. No. 14/012,652, Final Rejection, dated Nov. 17, 2016, 22 pages.
Mendoza-Wilkenfe, E., U.S. Appl. No. 14/012,652, Non-Final Rejection, dated Jun. 1, 2016, 74 pages.
Cheng, X., Application No. 201380053723.1, Office Action1 (with English translation), dated Jun. 6, 2016, 11 pages.

(56) References Cited

OTHER PUBLICATIONS

Zhou, Z., Application No. 201380056459.7, Office Action1 (with English translation), dated Jun. 14, 2017, 13 pages (dated Jun. 30, 2017).
Zhou, Z., Application No. 201380053729.9, Office Action1 (with English translation), dated Mar. 14, 2017, 21 pages.
Li, X., Application No. 201380053801.8, Office Action2 (with English translation), dated Apr. 21, 2017, 16 pages (dated May 5, 2017).
Li, X., Application No. 201380053801.8, Office Action1 (with English translation), dated Jul. 22, 2016, 7 pages.
Kim, International Application No. PCT/US2013/057077, Search Report and Written Opinion, dated Nov. 8, 2013, 10 pages.
Yang, International Application No. PCT/US2013/056997, Search Report and Written Opinion, dated Nov. 28, 2013, 12 pages.
Yang, International Application No. PCT/US2013/056986, Search Report and Written Opinion, dated Nov. 29, 2013, 12 pages.
Yang, International Application No. PCT/US2013/056983, Search Report and Written Opinion, dated Dec. 19, 2013, 12 pages.
Stoffa, W., U.S. Appl. No. 14/012,644, Non-Final Rejection, dated Mar. 10, 2014, 30 pages.
Stoffa, W., U.S. Appl. No. 14/012,644, Final Rejection, dated Jul. 3, 2014, 18 pages.
Stoffa, W., U.S. Appl. No. 14/012,644, Non-Final Rejection, dated Oct. 21, 2014, 19 pages.
Stoffa, W., U.S. Appl. No. 14/012,644, Notice of Allowance, dated Apr. 1, 2015, 15 pages.
Stoffa, W., U.S. Appl. No. 14/012,644, Notice of Allowance, dated Jul. 9, 2015, 32 pages.
Stoffa, W., U.S. Appl. No. 14/937,090, Notice of Allowance, dated Mar. 2, 2017, 18 pages.
Stoffa, W., U.S. Appl. No. 14/937,090, Final Rejection, dated Oct. 27, 2016, 45 pages.
Stoffa, W., U.S. Appl. No. 14/937,090, Non-Final Rejection, dated Jun. 1, 2016, 45 pages.
Stoffa, W., U.S. Appl. No. 15/388,506, Non-Final Rejection, dated Apr. 12, 2017, 51 pages.
Cox, A., U.S. Appl. No. 14/012,637, Final Rejection, dated Feb. 2, 2017, 33 pages.
Cox, A., U.S. Appl. No. 14/012,637, Final Rejection1 (updated to Non-Final Rejection dated Nov. 18, 2016), dated Aug. 25, 2016, 27 pages.
Cox, A., U.S. Appl. No. 14/012,637, Non-Final Rejection, dated Feb. 19, 2016, 49 pages.
Cox, A., U.S. Appl. No. 14/012,637, Non-Final Rejection, dated Jun. 29, 2017, 35 pages.
Krishnamurthy et al., "Food Processing Operations and Modeling: Design and Analysis," UV Pasteurization of Food Materials, Chapter 11, 2009, 22 pages.
Stoffa, W., U.S. Appl. No. 15/388,506, Notice of Allowance, dated Sep. 6, 2017, 35 pages.
Mayekar, K., U.S. Appl. No. 14/629,508, Notice of Allowance, dated Nov. 16, 2017, 22 pages.
Li, X., Application No. 201380053801.8, Rejection Decision—with English translation, dated Nov. 6, 2017, 14 pages.
Zhou, Z., Application No. 201380053729.9, Office Action2 (with English translation), dated Jan. 29, 2018, 13 pages.
Mendoza-Wilkenfe, E., U.S. Appl. No. 14/012,652, Office Action1, dated Apr. 9, 2018, 68 pages.
Martin, E., U.S. Appl. No. 15/670,750, Non-Final Rejection, dated Mar. 15, 2018, 62 pages.
Martin, E., U.S. Appl. No. 15/982,611, Non-Final Rejection, dated Aug. 1, 2018, 31 pages.
Stoffa, W., U.S. Appl. No. 15/856,978, Office Action, dated Sep. 7, 2018, 30 pages.
Mendoza-Wilkenfe, E., U.S. Appl. No. 14/012,652, Final Office Action1, dated Sep. 4, 2018, 13 pages.
Mayekar, K., U.S. Appl. No. 15/388,394, Final Office Action, dated Nov. 9, 2018, 7 pages.
Zhou, Z., Application No. 201380053729.9, Rejection Devision (with English translation), dated Jul. 25, 2018, received Aug. 22, 2018, 13 pages.
Wang, R., Application No. 201510249047.6, Office Action 1, dated Feb. 11, 2019, 11 pages.
Martin, E., U.S. Appl. No. 15/982,611, Notice of Allowance, dated Dec. 11, 2018, 11 pages.
Martin, E., U.S. Appl. No. 15/670,750, Notice of Allowance, dated Aug. 27, 2018, 7 pages.
Stoffa, W., U.S. Appl. No. 15/856,978, Final Office Action 1, dated Apr. 24, 2019, 7 pages.
Mayekar, K., U.S. Appl. No. 15/388,394, Notice of Allowance, dated May 28, 2019, 7 pages.
Mendoza-Wilkenfe, E., U.S. Appl. No. 14/012,652, Notice of Allowance, dated May 31, 2019, 13 pages.

\* cited by examiner

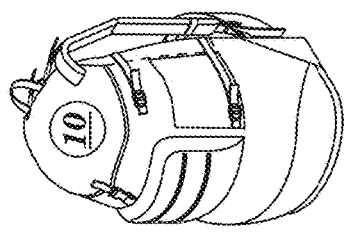
FIG. 4D
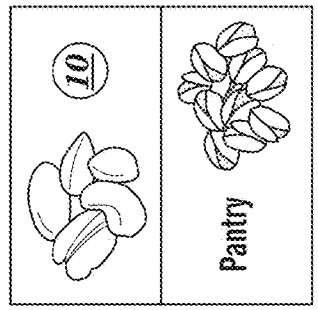
FIG. 4H
FIG. 4C
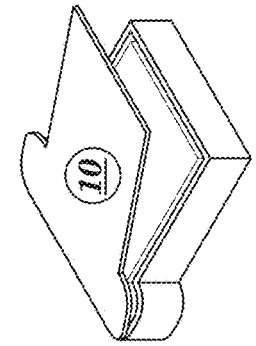
FIG. 4G
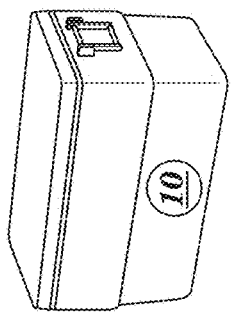
FIG. 4B
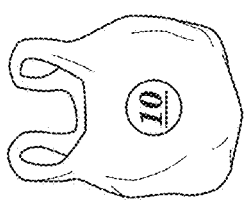
FIG. 4F
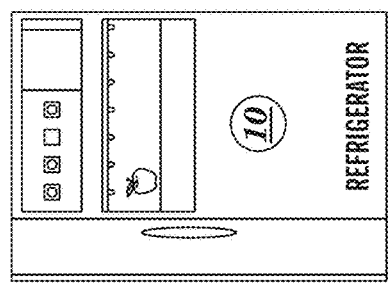
FIG. 4A
FIG. 4E

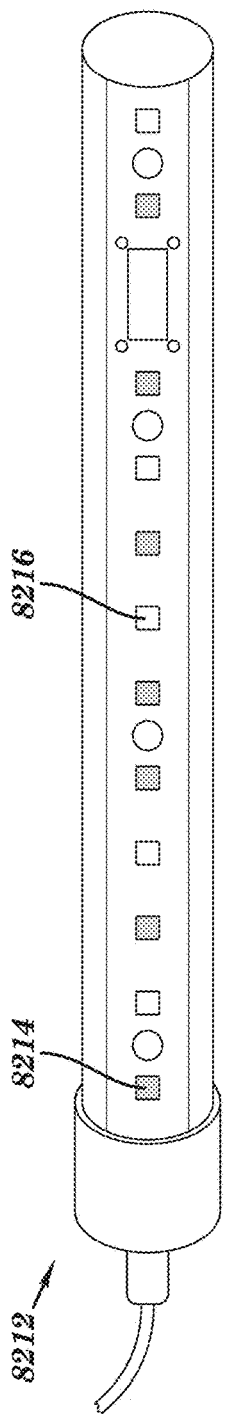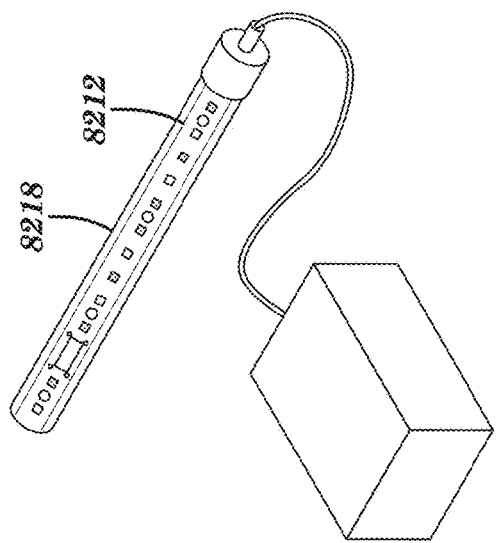
FIG. 12A
FIG. 12B

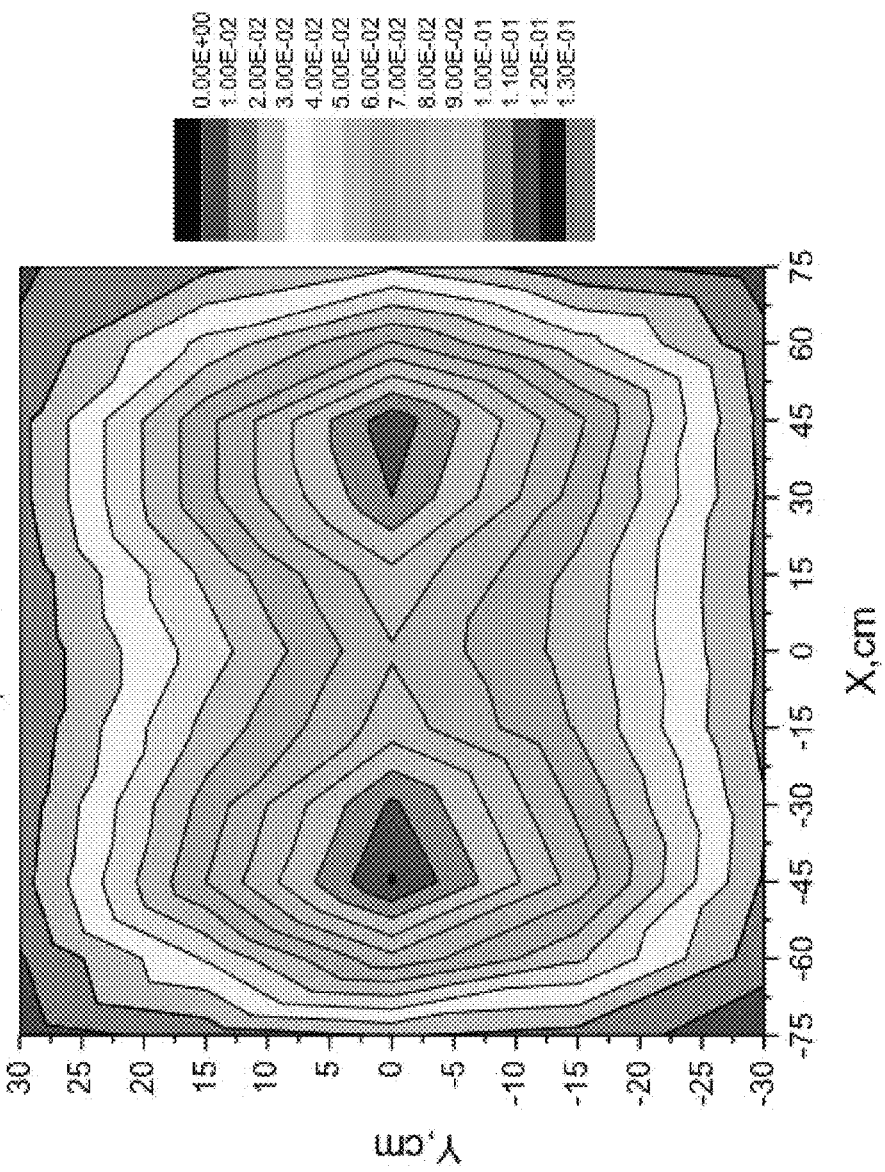

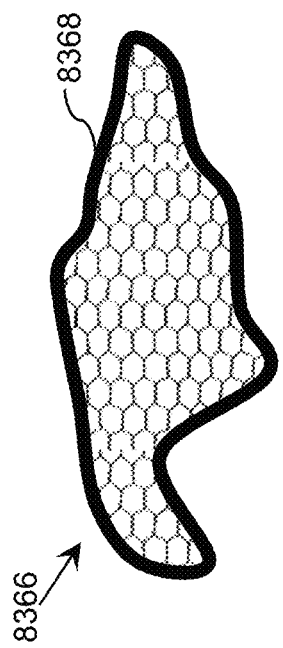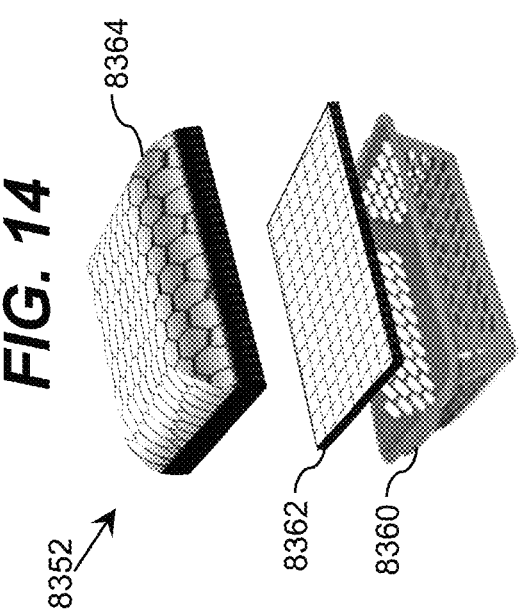

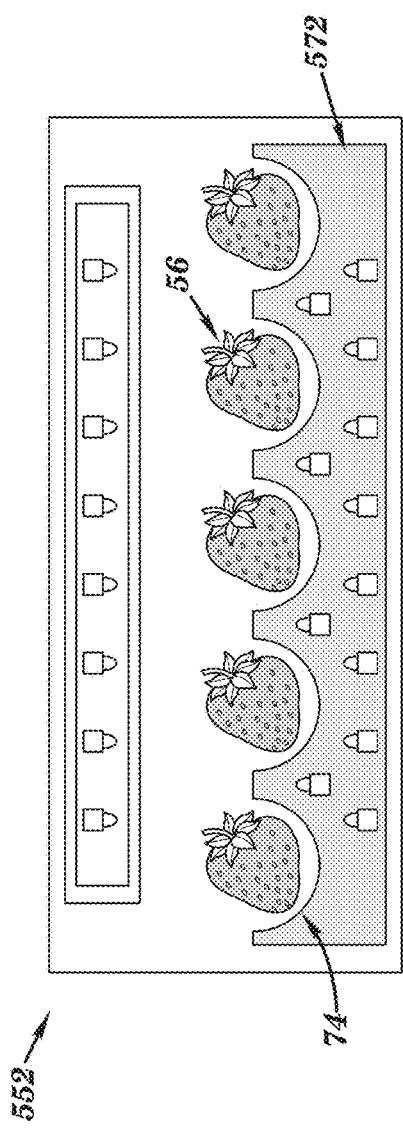
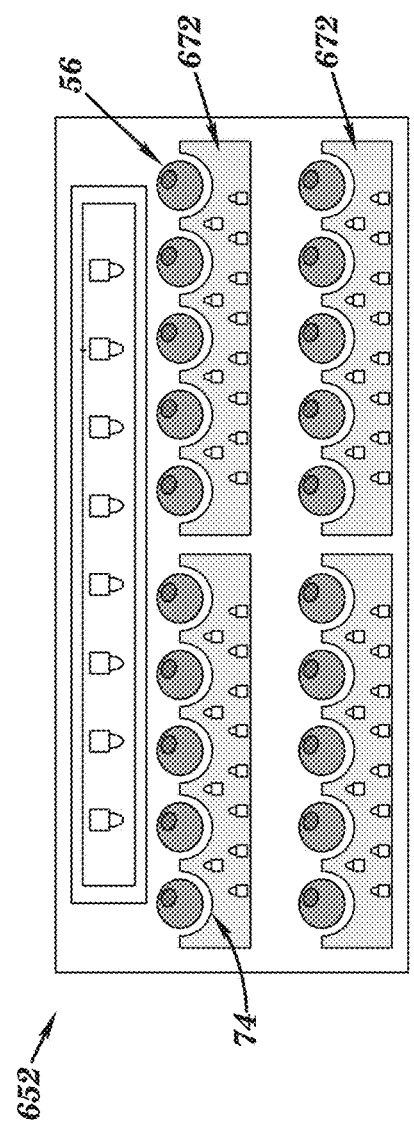
FIG. 20A
FIG. 20B

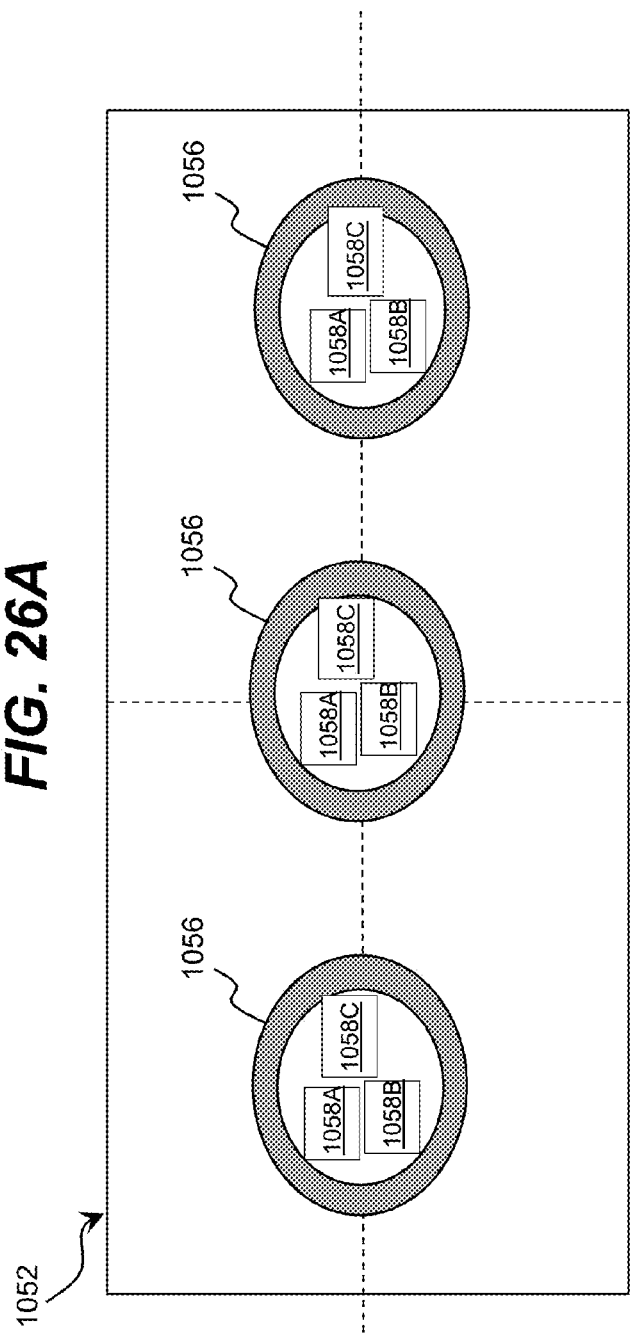
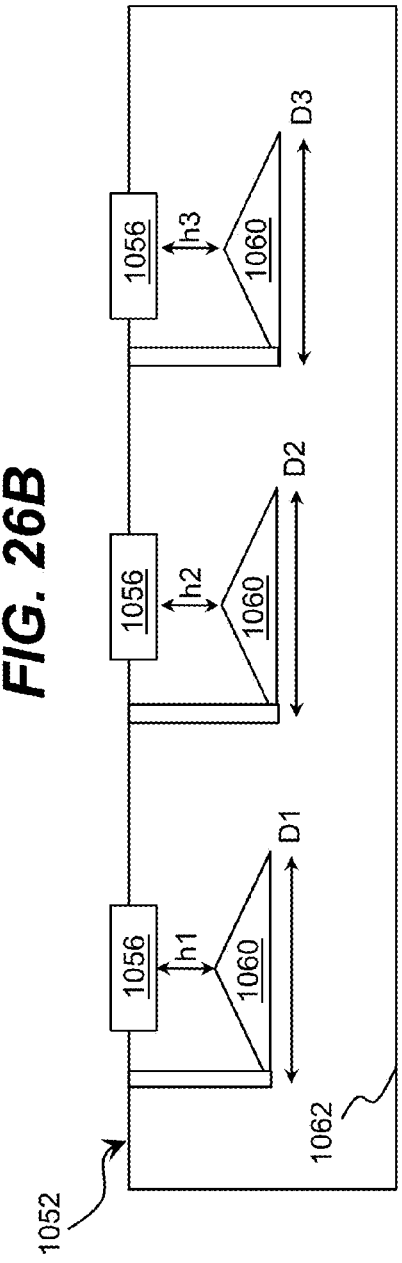
FIG. 26A
FIG. 26B

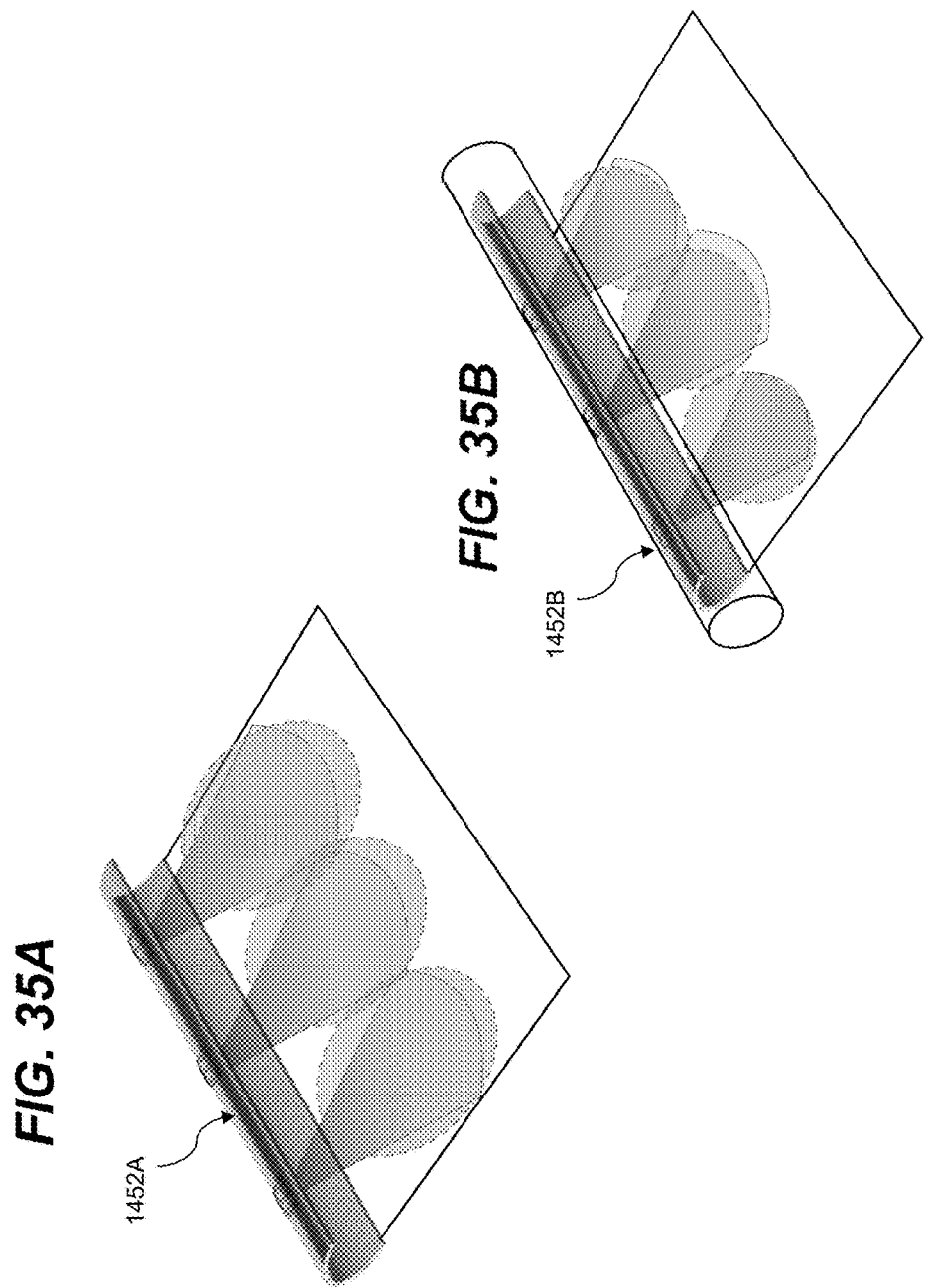

STORAGE DEVICE INCLUDING ULTRAVIOLET ILLUMINATION

REFERENCE TO RELATED APPLICATIONS

The current application claims the benefit of U.S. Provisional Application No. 62/385,581, filed on 9 Sep. 2016, which is hereby incorporated by reference. The current application is also a continuation-in-part application of U.S. application Ser. No. 15/388,394, filed on 22 Dec. 2016, which is a continuation-in-part application of U.S. application Ser. No. 14/629,508, filed on 24 Feb. 2015, which claims the benefit of U.S. Provisional Application No. 61/943,915, filed on 24 Feb. 2014, and U.S. Provisional Application No. 62/042,737, filed on 27 Aug. 2014, and which is also a continuation-in-part application of U.S. application Ser. No. 14/012,682, filed on 28 Aug. 2013, now U.S. Pat. No. 9,034,271, issued 19 May 2015, which claims the benefit of U.S. Provisional Application No. 61/694,229, filed on 28 Aug. 2012, and U.S. Provisional Application No. 61/694,232, filed on 28 Aug. 2012, all of which are hereby incorporated by reference. Additional aspects of the invention are related to the invention disclosed in the U.S. application Ser. No. 14/478,266, filed on 5 Sep. 2014, which is hereby incorporated by reference.

TECHNICAL FIELD

The disclosure relates generally to ultraviolet radiation, and more particularly, to a solution for preserving, disinfecting, and/or the like, stored items within an area, such as food items located in a storage area of a refrigerated unit, using ultraviolet radiation.

BACKGROUND ART

Reliable, hygienic storage of sanitary and biological items, such as food, is a major problem. For example, the problem is present throughout the food industry, e.g., manufacturers, retailers, restaurants, and in every household, and is especially significant for food service establishments, in which related issues of food quality control also are significant. In addition to food storage and quality control in fixed locations (e.g., a refrigerator) where access to electricity is readily available, proper food storage and quality control also is important in situations for which access to unlimited electricity and/or a stationary storage device, such as a refrigerator, is not available, such as picnics, camping, mobile food kiosks, hospitality or battlefield meal locations, search and rescue, etc. In addition to food, other stored items also require hygienic storage. For example, medical and chemical equipment, construction wood, etc., also require storage in a biologically safe environment. Since ambient temperature significantly affects bacterial activity, effective control of the ambient temperature is an important tool in ensuring reliable, hygienic storage of various items.

Fresh food products can be processed using ultraviolet light as a germicidal medium to reduce the food-born microbial load. Water has been treated with ultraviolet light to provide safe drinking water for quite some time. Fruit and vegetable products capable of being pumped through a system generally are very suitable for processing by ultraviolet light to reduce the microbial load. Today, most of these products are pasteurized to obtain microbiologically safe and nutritious products. However, pasteurization can change the taste and flavor of such products because of the temperature and processing time. Juices from different sources can be treated by exposure to ultraviolet light at different doses. On the other hand, variables such as exposure time, type of fruit product, juice color and juice composition, among other variables, need to be studied to obtain fruit products with reduced microbial load, increased shelf life and adequate sensory and nutritional characteristics. Reduction of microbial load through ultraviolet light application as a disinfection medium for food products other than liquids also is being studied. Moreover, ultraviolet technology could be a source for pasteurization of liquids, or disinfection of solid foods as an alternative technology, instead of thermal treatment or application of antimicrobial compounds.

In general, ultraviolet (UV) light is classified into three wavelength ranges: UV-C, from about 200 nanometers (nm) to about 280 nm; UV-B, from about 280 nm to about 315 nm; and UV-A, from about 315 nm to about 400 nm. Generally, ultraviolet light, and in particular, UV-C light is "germicidal," i.e., it deactivates the DNA of bacteria, viruses and other pathogens and thus destroys their ability to multiply and cause disease. This effectively results in sterilization of the microorganisms. Specifically, UV-C light causes damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. UV light with a wavelength of approximately between about 250 to about 280 nm provides the highest germicidal effectiveness. While susceptibility to UV light varies, exposure to UV energy for about 20 to about 34 milliwatt-seconds/cm2 is adequate to deactivate approximately 99 percent of the pathogens.

Various approaches have sought to use ultraviolet light to disinfect a compartment, such as compartments found in refrigerators. For example, one approach proposes a plurality of small, low current UV lights which utilize the standard circuitry of the refrigerator to power the UV light source. Another approach uses a UV lamp installed in a top portion of the refrigerator and reflective lining throughout the interior to reflect the UV radiation throughout the compartment. Another approach provides a UV system with a single UV source attached to an internal sidewall of a refrigerator to radiate light to the entire compartment, or in the alternative, provide UV exposure to a limited compartment. Still another approach proposes an air cleaner for an internal compartment of a refrigerator, which utilizes a UV filter to reduce pathogens in the re-circulated air. Still another approach provides a refrigerator with UV light irradiation components to eradicate low-level light from the storage containers contained therein to promote freshness of foodstuffs.

SUMMARY OF THE INVENTION

While refrigerators have been widely used to maintain the freshness of foods stored therein, and several approaches for using UV light devices in connection with refrigerators have been proposed, the inventors recognize that these approaches fail to adequately address food life prolongation, disinfection, ethylene decomposition, and/or the like, through the use of UV source(s), such as UV light emitting diode(s), capable of emitting UV radiation of different wavelengths and/or intensities.

The inventors provide a solution for preserving, disinfecting, and/or the like, stored items within a storage area, such as a storage area of a refrigerated unit, using ultraviolet radiation. For example, an embodiment of the solution is configured to monitor biodegradable items within the storage area and determine and apply a target amount of ultraviolet radiation to preserve and/or disinfect the items, without affecting the quality of the items. Embodiments of the system can be implemented in any of various types of storage environments, such as refrigerators, pantries, reusable grocery bags, coolers, boxes, biological and/or sterile object storage containers, and/or the like.

Aspects of the invention provide a solution in which ultraviolet radiation is directed within an area. Items located within the area and/or one or more conditions of the area are monitored over a period of time. Based on the monitoring, ultraviolet radiation sources are controlled by adjusting a direction, an intensity, a pattern, and/or a spectral power of the ultraviolet radiation generated by the ultraviolet radiation source. Adjustments to the ultraviolet radiation source(s) can correspond to one of a plurality of selectable operating configurations including a storage life preservation operating configuration, a disinfection operating configuration, an ethylene decomposition operating configuration, and/or the like.

A first aspect of the invention provides a system comprising: at least one ultraviolet radiation source configured to generate ultraviolet radiation directed within a storage area; and a control system for controlling ultraviolet radiation generated by the at least one ultraviolet radiation source using one of a plurality of selectable operating configurations and a set of current conditions of at least one of: the storage area or a set of items located in the storage area, wherein the controlling includes adjusting at least one of: a direction, an intensity, a pattern, or a spectral power of ultraviolet radiation directed within the storage area based on the set of current conditions of the storage area and a set of target conditions for at least one of: the storage area or a set of items located in the storage area corresponding to a currently selected one of the plurality of selectable operating configurations, and wherein the plurality of selectable operating configurations include: a storage life preservation operating configuration, a disinfection operating configuration, and an ethylene decomposition operating configuration.

A second aspect of the invention provides a food storage device comprising: a storage area configured to store at least one perishable food item; at least one ultraviolet radiation source configured to generate ultraviolet radiation directed within the storage area; and a monitoring system for monitoring a set of current conditions of at least one of: the storage area or a set of items located in the storage area, wherein the set of current conditions includes a set of current biological conditions of the storage area and an operating condition of the at least one ultraviolet radiation source.

A third aspect of the invention provides a refrigeration device comprising: a storage area configured to store at least one refrigerated item; a component configured to control at least one environmental condition of the storage area, wherein the at least one environmental condition includes at least one of: a temperature, a humidity, a gas convection, or a fluid convection; at least one ultraviolet radiation source configured to generate ultraviolet radiation directed within the storage area; and a monitoring and control system for managing the storage area by performing a method comprising: monitoring a set of current conditions of at least one of: the storage area or a set of items located in the storage area; and controlling ultraviolet radiation generated by the at least one ultraviolet radiation source using one of a plurality of selectable operating configurations and the set of current conditions, wherein the controlling includes adjusting at least one of: a direction, an intensity, a pattern, or a spectral power of ultraviolet radiation directed within the storage area based on the set of current conditions of the storage area and a set of target conditions for at least one of: the storage area or a set of items located in the storage area corresponding to a currently selected one of the plurality of selectable operating configurations, and wherein the plurality of selectable operating configurations include: a storage life preservation operating configuration, a disinfection operating configuration, and an ethylene decomposition operating configuration.

A fourth aspect of the invention provides a system comprising: a storage device including a storage area for containing at least one item, wherein the storage area is at least partially defined by: a transparent region fixed in the storage device, wherein the transparent region is configured to transmit ultraviolet radiation; and a reflecting region adjacent to the transparent region, wherein the reflecting region is configured to reflect ultraviolet radiation into the storage area; and a set of ultraviolet radiation sources configured to generate ultraviolet radiation into the storage area, wherein at least one of the set of ultraviolet radiation sources is adjacent to the at least one transparent region.

A fifth aspect of the invention provides a storage device comprising: a storage area for containing at least one item; means for removably mounting an ultraviolet radiation source configured to generate ultraviolet radiation directed into the storage area, wherein the means for removably mounting includes: a reflecting region adjacent to the ultraviolet radiation source, the reflecting region configured to reflect ultraviolet radiation into the storage area; and a transparent region isolating the ultraviolet radiation source from an interior of the storage area, the transparent region configured to transmit ultraviolet radiation into the storage area; and a monitoring and control system for monitoring a set of current conditions for at least one of: the storage area and the at least one item, and for controlling the ultraviolet radiation source based on the set of current conditions.

A sixth aspect of the invention provides a storage device comprising: a storage area for containing at least one item; a set of ultraviolet radiation sources located within the storage device and configured to generate ultraviolet radiation into the storage area, wherein the set of ultraviolet radiation sources are located in a hollow region defined by a reflecting surface configured to reflect ultraviolet radiation into the storage area and a transparent surface configured to transmit ultraviolet radiation; a set of visible and infrared radiation sources configured to generate radiation into the storage area; and a monitoring and control system for monitoring a set of current conditions of the storage area and controlling the set of ultraviolet radiation sources and the set of visible and infrared radiation sources using the set of current conditions.

A seventh aspect of the invention provides a system comprising: a storage device including a storage area for containing at least one item, wherein the storage area includes at least one shelf for holding the at least one item; a set of ultraviolet radiation sources configured to generate ultraviolet radiation into the storage area; a set of sensing devices configured to monitor a set of current conditions of at least one of: the storage area or the at least one item; and a control system configured to control the set of ultraviolet radiation sources based on the set of current conditions.

An eighth aspect of the invention provides a storage device comprising: a storage area including at least one shelf for holding at least one item; a set of ultraviolet radiation sources configured to generate ultraviolet radiation into the storage area; a set of sensing devices configured to monitor a set of current conditions of at least one of: the storage area or the at least one item, the set of sensing devices including a visual camera configured to capture an image of the at least one item; and a control system configured to control the set of ultraviolet radiation sources based on the set of current conditions.

A ninth aspect of the invention provides a storage device comprising: a storage area including at least one shelf for holding at least one item, wherein the at least one shelf includes a plurality of sub-compartments; a set of ultraviolet radiation sources configured to generate ultraviolet radiation into the storage area; a set of sensing devices configured to monitor a set of current conditions of at least one of: the storage area or the at least one item, the set of sensing devices including a visual camera configured to capture an image of the at least one item; and a control system configured to control the set of ultraviolet radiation sources based on the set of current conditions.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 4A-4H show illustrative storage devices for use with an ultraviolet radiation system according to embodiments.

FIG. 8A shows a feedback loop according to an embodiment, while

FIG. 12A shows an illustrative ultraviolet radiation source for use with a storage device according to an embodiment, while FIG. 12B shows an illustrative ultraviolet radiation source within an ultraviolet transparent enclosure according to an embodiment.

FIG. 13 shows an exemplary power distribution plot according to an embodiment.

FIG. 14 shows an illustrative storage device for use with an ultraviolet radiation system according to an embodiment.

FIG. 15 shows an illustrative mesh for a storage device according to an embodiment.

FIGS. 20A and 20B show cross-sectional views of illustrative storage devices according to embodiments.

FIGS. 26A and 26B show a top view and a cross-sectional view, respectively, of an illustrative structure for use in conjunction with a storage device according to an embodiment.

FIGS. 35A and 35B show the light diffusion of ultraviolet radiation sources without a transparent enclosure and with a transparent enclosure, respectively, according to an embodiment.

FIG. 39A shows an illustrative ultraviolet radiation system including a rail system for the ultraviolet radiation sources according to an embodiment, while

FIG. 42A shows an illustrative lamp for use with an ultraviolet radiation system according to an embodiment, while

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution in which ultraviolet radiation is directed within an area. Items located within the area and/or one or more conditions of the area are monitored over a period of time. Based on the monitoring, ultraviolet radiation sources are controlled by adjusting a direction, an intensity, a pattern, and/or a spectral power of the ultraviolet radiation generated by the ultraviolet radiation source. Adjustments to the ultraviolet radiation source(s) can correspond to one of a plurality of selectable operating configurations including a storage life preservation operating configuration, a disinfection operating configuration, an ethylene decomposition operating configuration, and/or the like.

As used herein, unless otherwise noted, the term "set" means one or more (i.e., at least one) and the phrase "any solution" means any now known or later developed solution. Furthermore, as used herein, ultraviolet radiation/light means electromagnetic radiation having a wavelength ranging from approximately 10 nanometers (nm) to approximately 400 nm, while ultraviolet-C (UV-C) means electromagnetic radiation having a wavelength ranging from approximately 100 nm to approximately 280 nm, ultraviolet-B (UV-B) means electromagnetic radiation having a wavelength ranging from approximately 280 to approximately 315 nanometers, and ultraviolet-A (UV-A) means electromagnetic radiation having a wavelength ranging from approximately 315 to approximately 400 nanometers. As also used herein, a material/structure is considered to be "reflective" to ultraviolet light of a particular wavelength when the material/structure has an ultraviolet reflection coefficient of at least thirty percent for the ultraviolet light of the particular wavelength. In a more particular embodiment, a highly ultraviolet reflective material/structure has an ultraviolet reflection coefficient of at least eighty percent. Furthermore, a material/structure is considered to be "transparent" to ultraviolet light of a particular wavelength when the material/structure allows a significant amount of the ultraviolet radiation to pass there through. In an embodiment, the ultraviolet transparent structure is formed of a material and has a thickness, which allows at least ten percent of the ultraviolet radiation to pass there through.

Figure 1:
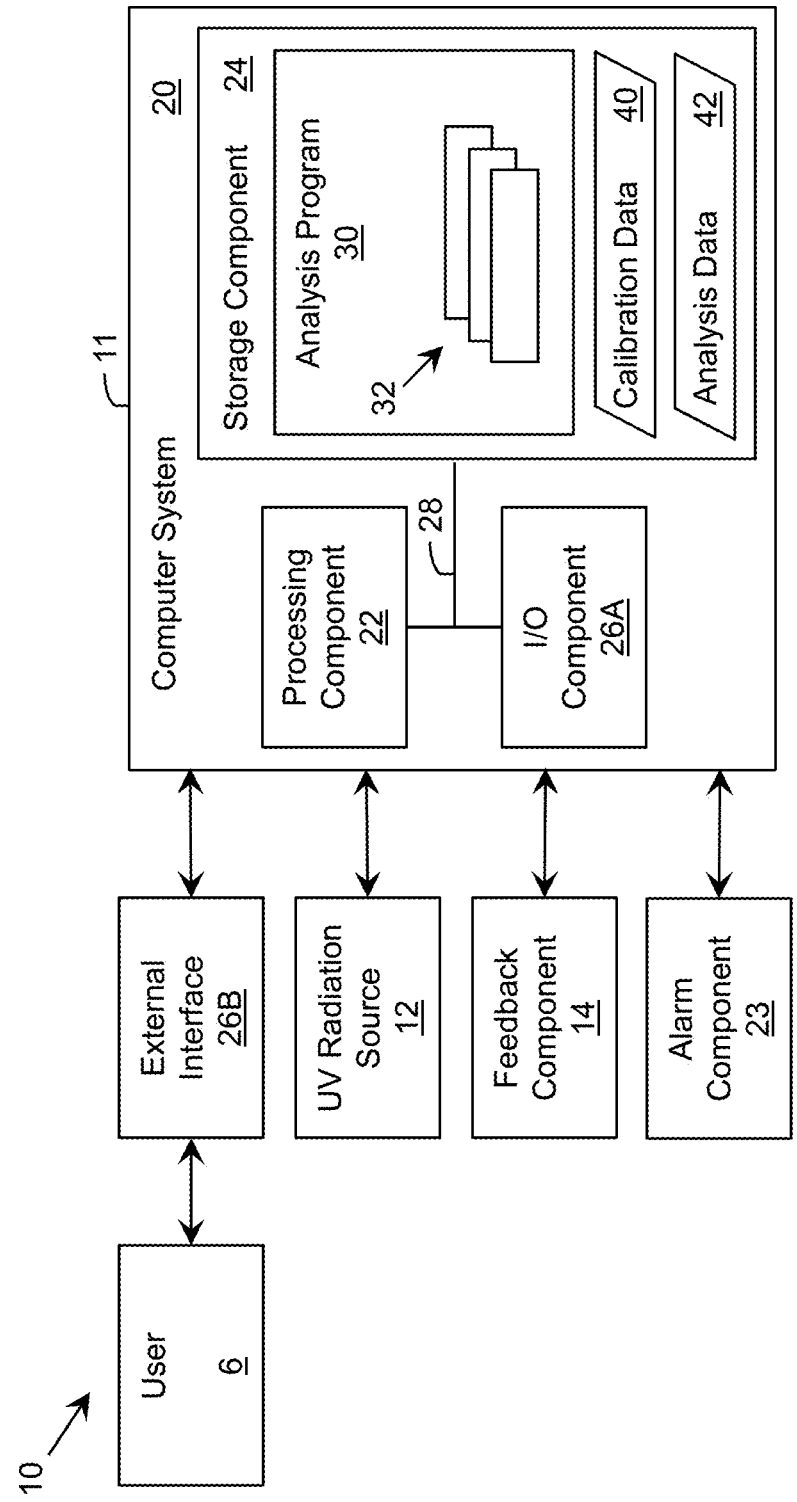
FIG. 1 shows an illustrative ultraviolet radiation system according to an embodiment.

Turning to the drawings, FIG. 1 shows an illustrative ultraviolet radiation system 10 according to an embodiment. In this case, the system 10 includes a monitoring and/or control system 11, which is implemented as a computer system 20 including an analysis program 30, which makes the computer system 20 operable to manage an ultraviolet (UV) radiation source 12 by performing a process described herein. In particular, the analysis program 30 can enable the computer system 20 to operate the UV radiation source 12 to generate and direct ultraviolet radiation within an area and process data corresponding to one or more conditions of the area and/or an item located in the area, which is acquired by a feedback component 14. While a single UV radiation source 12 is shown, it is understood that the area can include any number of UV radiation sources 12, the operation of which the computer system 20 can separately manage using a process described herein.

In an embodiment, during an initial period of operation (e.g., after recent access to the area, addition/removal/reconfiguration of item(s) placed within the area, and/or the like), the computer system 20 can acquire data from the feedback component 14 regarding one or more attributes of the items in the area and/or conditions of the area and generate analysis data 42 for further processing. The analysis data 42 can include information on the color, appearance, and/or the like, of items in the area, the presence of microorganisms on the items or within the area, and/or the like. Furthermore, the analysis data 42 can include information on the presence of ethylene gas within the area. The computer system 20 can use the analysis data 42 to generate calibration data 40 for controlling one or more aspects of the ultraviolet radiation generated by the ultraviolet radiation source(s) 12 using one of a plurality of selectable operating configurations as discussed herein. Furthermore, one or more aspects of the operation of the ultraviolet radiation source 12 can be controlled by a user 6 via an external interface component 26B.

The computer system 20 is shown including a processing component 22 (e.g., one or more processors), a storage component 24 (e.g., a storage hierarchy), an input/output (I/O) component 26A (e.g., one or more I/O interfaces and/or devices), and a communications pathway 28. In general, the processing component 22 executes program code, such as the analysis program 30, which is at least partially fixed in the storage component 24. While executing program code, the processing component 22 can process data, which can result in reading and/or writing transformed data from/to the storage component 24 and/or the I/O component 26A for further processing. The pathway 28 provides a communications link between each of the components in the computer system 20. The I/O component 26A and/or the external interface component 26B can comprise one or more human I/O devices, which enable a human user 6 to interact with the computer system 20 and/or one or more communications devices to enable a system user 6 to communicate with the computer system 20 using any type of communications link. To this extent, during execution by the computer system 20, the analysis program 30 can manage a set of interfaces (e.g., graphical user interface(s), application program interface, and/or the like) that enable human and/or system users 6 to interact with the analysis program 30. Furthermore, the analysis program 30 can manage (e.g., store, retrieve, create, manipulate, organize, present, etc.) the data, such as calibration data 40 and analysis data 42, using any solution.

In any event, the computer system 20 can comprise one or more general purpose computing articles of manufacture (e.g., computing devices) capable of executing program code, such as the analysis program 30, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 30 can be embodied as any combination of system software and/or application software.

Furthermore, the analysis program 30 can be implemented using a set of modules 32. In this case, a module 32 can enable the computer system 20 to perform a set of tasks used by the analysis program 30, and can be separately developed and/or implemented apart from other portions of the analysis program 30. When the computer system 20 comprises multiple computing devices, each computing device can have only a portion of the analysis program 30 fixed thereon (e.g., one or more modules 32). However, it is understood that the computer system 20 and the analysis program 30 are only representative of various possible equivalent monitoring and/or control systems 11 that may perform a process described herein. To this extent, in other embodiments, the functionality provided by the computer system 20 and the analysis program 30 can be at least partially implemented by one or more computing devices that include any combination of general and/or specific purpose hardware with or without program code. In each embodiment, the hardware and program code, if included, can be created using standard engineering and programming techniques, respectively. In another embodiment, the monitoring and/or control system 11 can be implemented without any computing device, e.g., using a closed loop circuit implementing a feedback control loop in which the outputs of one or more sensing devices are used as inputs to control the operation of one or more other devices (e.g., LEDs). Illustrative aspects of the invention are further described in conjunction with the computer system 20. However, it is understood that the functionality described in conjunction therewith can be implemented by any type of monitoring and/or control system 11.

Regardless, when the computer system 20 includes multiple computing devices, the computing devices can communicate over any type of communications link. Furthermore, while performing a process described herein, the computer system 20 can communicate with one or more other computer systems, such as the user 6, using any type of communications link. In either case, the communications link can comprise any combination of various types of wired and/or wireless links; comprise any combination of one or more types of networks; and/or utilize any combination of various types of transmission techniques and protocols. This communications link, which can include a wireless or cable based transmission, can be utilized to transmit information about the state of one or more items and/or zones within the storage area 54.

The system 10 can be implemented within an existing storage device (e.g., a refrigerator) using any solution. For example, one or more ultraviolet radiation sources 12 and one or more devices included in a feedback component 14 can be fixed within various locations in the storage device (e.g., on walls, shelves, etc.) and configured for operation by the computer system 20. The locations of devices in the ultraviolet radiation source(s) 12 and/or the feedback component 14 can be selected to provide comprehensive coverage of the storage area of the storage device and the items located within the storage area. In an embodiment, the computer system 20 can be located outside of the storage area of the storage device.

The ultraviolet radiation source 12 can comprise any combination of one or more ultraviolet radiation emitters. For example, the UV source 12 can include a high intensity ultraviolet lamp (e.g., a high intensity mercury lamp), an ultraviolet light emitting diode (LED), and/or the like. In an embodiment, the UV source 12 includes a set of light emitting diodes manufactured with one or more layers of materials selected from the group-III nitride material system (e.g., $Al_xIn_yGa_{1-X-Y}N$, where $0 \le x$, $y \le 1$, and $x+y \le 1$ and/or alloys thereof). Additionally, the UV source 12 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like, within the storage area. Illustrative wave guiding structures include, but are not limited to, a plurality of ultraviolet fibers, each of which terminates at an opening, a diffuser, and/or the like. The computer system 12 can independently control each UV source 12.

The system 10 also can include an alarm component 23, which can be operated by the computer system 20 to indicate when ultraviolet radiation is being directed within the storage area. The alarm component 23 can include one or more devices for generating a visual signal, an auditory signal, and/or the like. For example, in the example shown in FIG. 4A, where the storage device 52 includes a refrigeration device, a panel 8 can display a flashing light, text, an image, and/or the like, to indicate that ultraviolet radiation is currently being directed into a corresponding storage area 54. Furthermore, the alarm component 23 can generate a noise, such as a bell, a beep, and/or the like, to indicate that ultraviolet radiation is currently being directed to the storage area 54.

Figure 2:
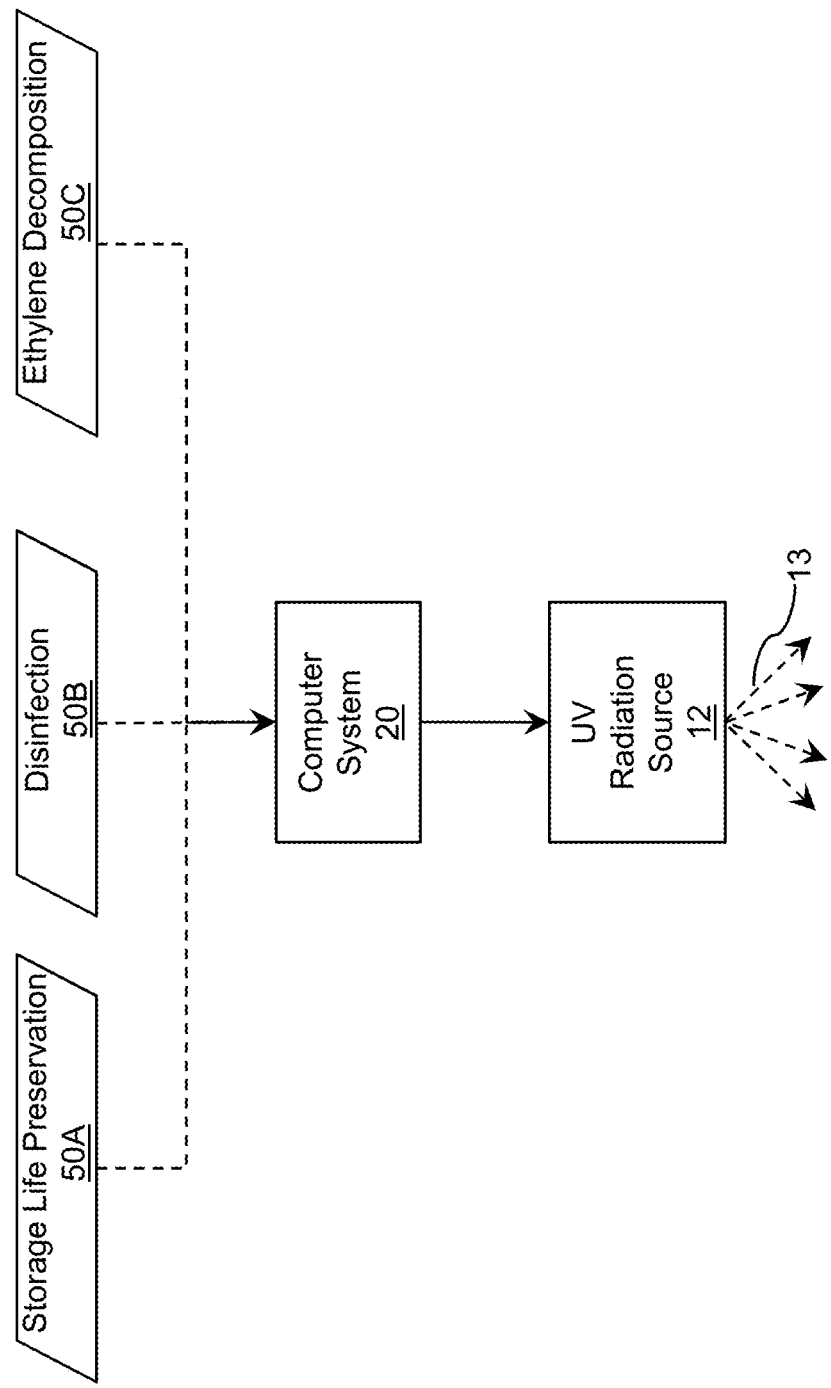
FIG. 2 shows a block diagram illustrating use of operating configurations for operating an ultraviolet radiation source according to an embodiment.

FIG. 2 shows a block diagram illustrating use of operating configurations for operating an ultraviolet radiation source 12 according to an embodiment. As illustrated, the computer system 20 can use data corresponding to a selected operating configuration 50A-50C to adjust one or more aspects of the ultraviolet radiation 13 generated by the ultraviolet radiation source(s) 12. In an embodiment, the operating configurations 50A-50C can include a storage life preservation operating configuration 50A, a disinfection operating configuration 50B, and an ethylene decomposition operating configuration 50C. In an embodiment, the storage life preservation operating configuration 50A is configured to increase a storage lifespan of items stored within the area, while the disinfection operating configuration 50B is configured to eliminate and/or decrease an amount of microorganisms present within the area or on item(s) located within the area. The ethylene decomposition operating configuration 50C can be configured to remove ethylene from the atmosphere of the storage area, which would otherwise decrease the storage lifespan of items located within the area. One or more of these operating configurations can be configured to improve and/or maintain the visual appearance and/or nutritional value of the items within the storage area. For example, increasing the storage lifespan can include suppressing microorganism growth, maintaining and/or improving nutritional value, maintaining and/or improving visual appearance, and/or the like. Also, the operating configurations can be configured to prevent the build-up of mold within the storage area and/or on the items within the storage area.

The computer system 20 is configured to control and adjust a direction, an intensity, a pattern, and/or a spectral power (e.g., wavelength) of the ultraviolet radiation sources 12 to correspond to a particular operating configuration 50A-50C. The computer system 20 can control and adjust each property of the UV source 12 independently. For example, the computer system 20 can adjust the intensity, the time duration, and/or time scheduling (e.g., pattern) of the UV source 12 for a given wavelength. Each operating configuration 50A-50C can designate a unique combination of: a target ultraviolet wavelength, a target intensity level, a target pattern for the ultraviolet radiation (e.g., time scheduling, including duration (e.g., exposure/illumination time), duty cycle, time between exposures/illuminations, and/or the like), a target spectral power, and/or the like, in order to meet a unique set of goals corresponding to each operating configuration 50A-50C.

For example, the storage life preservation operating configuration 50A can require an ultraviolet wavelength of approximately 290 nm peak emission of a relatively lower intensity substantially continuous radiation. For example, an illustrative intensity range can be between approximately 0.1 milliwatt/m$^2$ and approximately 1000 milliwatt/m$^2$. In an embodiment, the intensity for the ultraviolet radiation in the storage life preservation operating configuration 50A can be approximately 400 microwatts/cm$^2$. In a more specific illustrative embodiment, the ultraviolet LEDs can direct ultraviolet radiation having an intensity of a few (e.g., 1-3) microwatts/cm$^2$ for approximately seven days within an enclosure that does not allow ultraviolet radiation to escape, such as an aluminum tube.

The disinfection operating configuration 50B can require any subset of ultraviolet wavelengths in the range of ultraviolet wavelengths (e.g., between approximately 10 nm and approximately 400 nm) and higher intensity levels. In an embodiment, the intensity range can be between approximately 1 milliwatt/m$^2$ and approximately 10 watt/m$^2$. In a more specific embodiment, the ultraviolet wavelength and intensity levels for the disinfection operating configuration 50B can be between approximately 250-290 nm and approximately 20 microwatt/cm$^2$ or higher, respectively, and the ultraviolet light can be applied for approximately 20 minutes. In this case, the dosage of ultraviolet radiation for the disinfection operating configuration 50B can be approximately 24 milliJoule/cm$^2$. However, it is understood that this is only illustrative and a dosage can be at least approximately 16 milliJoule/cm$^2$. The ethylene decomposition operating configuration 50C can require even higher intensity levels and the disinfection operating configuration 50B and a relatively low ultraviolet wavelength of approximately 230-270 nm. In an embodiment, the intensity range can be between approximately 1 milliwatt/m$^2$ and approximately 1000 watt/m$^2$.

Figure 3:
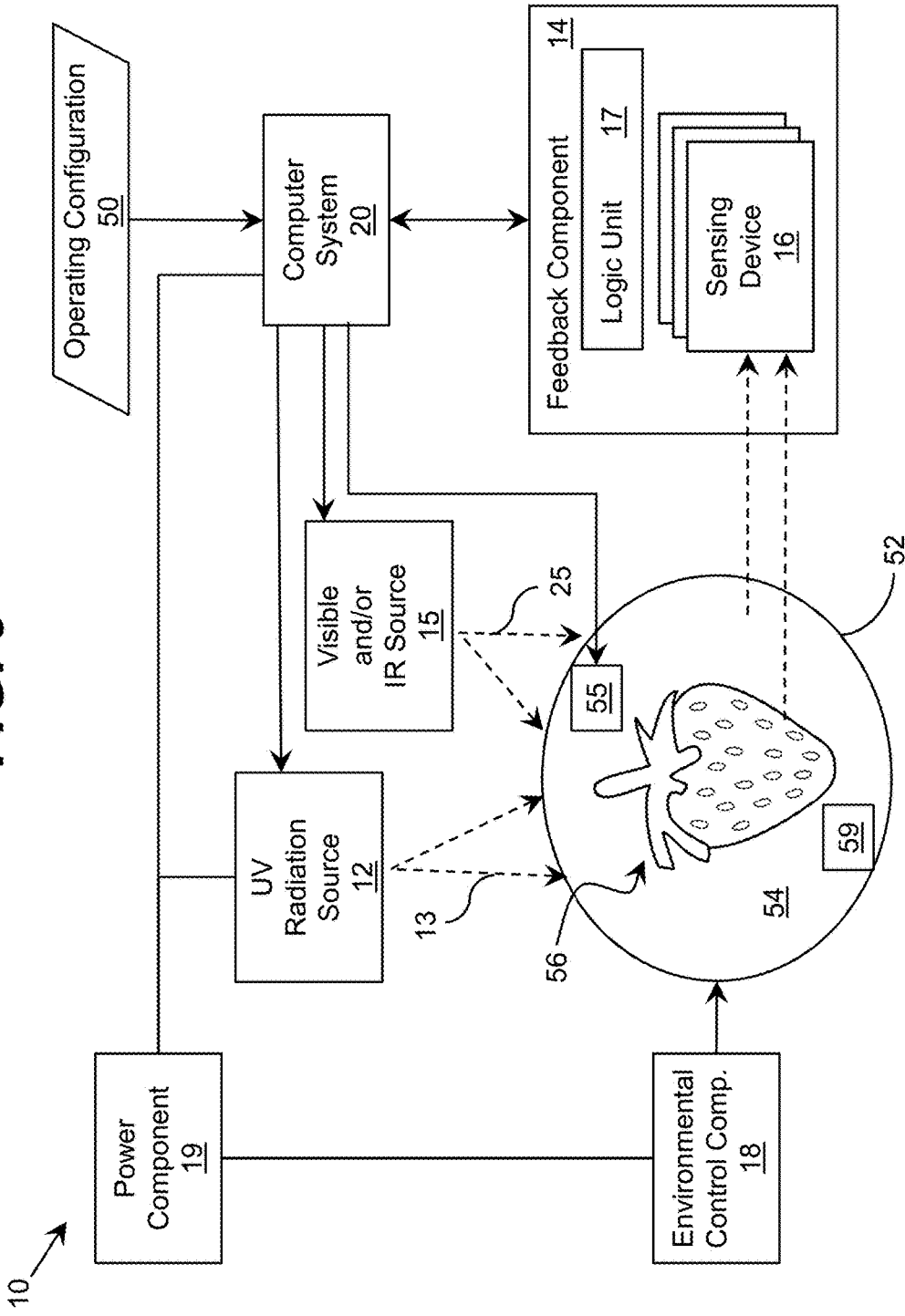
FIG. 3 shows an illustrative system including an ultraviolet radiation system according to an embodiment.

FIG. 3 shows an illustrative system including an ultraviolet radiation system 10 according to an embodiment. The computer system 20 is configured to control the ultraviolet radiation source 12 to direct ultraviolet radiation 13 into a storage area 54 of a storage device 52, within which a set of items 56 are located. The feedback component 14 is configured to acquire data used to monitor a set of current conditions of the storage area 54 and/or the items 56 over a period of time. As illustrated, the feedback component 14 can include a plurality of sensing devices 16, each of which can acquire data used by the computer system 20 to monitor the set of current conditions.

In an embodiment, the sensing devices 16 include at least one of a visual camera or a chemical sensor. The visual camera can acquire data (e.g., visual, electronic, and/or the like) used to monitor the storage area 54 and/or one or more of the items 56 located therein, while the chemical sensor can acquire data (e.g., chemical, electronic, and/or the like) used to monitor the storage area 54 and/or one or more of the items 56 located therein. The set of current conditions of the storage area 54 and/or items 56 can include the color or visual appearance of the items 56, the presence of microorganisms within the storage area 54, and/or the like. In an embodiment, the visual camera comprises a fluorescent optical camera. In this case, when the computer system 20 is operating the UV radiation source 12 in the storage life preservation operating configuration 50A (FIG. 2), the visual camera can be operated to detect the presence of microorganisms as they fluoresce in the ultraviolet light. In an embodiment, the chemical sensor is an infrared sensor, which is capable of detecting any combination of one or more gases, such as ethylene, ethylene oxide, and/or the like. However, it is understood that a visual camera and a chemical sensor are only illustrative of various types of sensors that can be implemented. For example, the sensing devices 16 can include one or more mechanical sensors (including piezoelectric sensors, various membranes, cantilevers, a micro-electromechanical sensor or MEMS, a nanomechanical sensor, and/or the like), which can be configured to acquire any of various types of data regarding the storage area 54 and/or items 56 located therein. In the ethylene decomposition operating configuration 50C, the storage device 52 can include a high efficiency ethylene destruction chamber 55 that includes a high UV reflectivity, high UV intensity radiation chamber for chemical (e.g., ethylene) destruction. In this embodiment, the computer system 20 can operate the one or more devices in the chamber 55 to destroy ethylene, which may be present within the atmosphere of the storage area 54. The computer system 20 can separately monitor the ethylene levels and the level of microorganism activity.

In an embodiment, the sensing devices 16 can also include a load sensor configured to detect the load (e.g., the weight) of the one or more items 56 located within the storage area 54. A precision of the load sensor can be +/−10 grams. The load sensor can be located anywhere within a storage area 54. For example, when the storage device 52 includes a storage area with a shelf, such as a refrigerator and/or freezer (FIG. 4A), a pantry (FIG. 4H), and/or the like, the load sensor can be located on the shelf. It is understood that if the storage device includes multiple shelves, that each shelf can include a load sensor. For example, in FIG. 13, two shelves 472 are shown in the storage device 452 and each shelf 472 can include a load sensor. In another embodiment, each shelf within a storage device 52 can include a set of regions and each region can include a load sensor that is configured to detect the weight of the one or more items 56 located on the shelf within that region. For example, in FIG. 15, the shelf 772 is divided into a first sub-compartment 76 and a second sub-compartment 78 and each sub-compartment 76, 78 can include a load sensor. The feedback component 14 also can include one or more additional devices. For example, the feedback component 14 is shown including a logic unit 17. In an embodiment, the logic unit 17 receives data from a set of sensing devices 16 and provides data corresponding to the set of conditions of the storage area 54 and/or items 56 located in the storage area 54 for processing by the computer system 20. In a more particular embodiment, the computer system 20 can provide information corresponding to the currently selected operating configuration 50 for use by the feedback component 14. For example, the logic unit 17 can adjust the operation of one or more of the sensing devices 16, operate a unique subset of the sensing devices 16, and/or the like, according to the currently selected operating configuration 50. In response to data received from the feedback component 14, the computer system 20 can automatically adjust and control one or more aspects of the ultraviolet radiation 13 generated by the ultraviolet radiation source 12 according to the currently selected operating configuration 50.

In an embodiment, the logic unit 17 can receive data corresponding to the weight of the items 56 located within the storage area 54 for processing by the computer system 20. For example, the logic unit 17 can provide a weight map to the computer system 20 that shows the distribution of the weight within the storage area 54. The computer system 20 can evaluate this data to determine the distribution of the weight of the items 56 across one or more shelves located within the storage area 54. In an embodiment, the computer system 20 can evaluate the weight data in combination with data from a visual camera in order to determine the type of item 56 located in the storage area 54. The visual camera can provide a 2-dimensional (2D) or 3-dimensional (3D) image of the items 56 located within the storage area 54. The visual camera can provide a visual image based on at least one of visible photography, infrared photography, ultraviolet photography, and/or the like.

In an embodiment, the system 10 can include visible and/or infrared (IR) sources 15 which can be controlled by the computer system 20 to generate light 25 directed within the storage area 54. For example, the computer system 20 can control the visible source 15 to generate light 25 with wavelengths configured to increase photosynthesis in one or more food items 56. Additionally, the computer system 20 can control the IR source 15 to generate light 25 directed onto certain foods to locally increase the temperature of the food items 56. The visible and/or IR source 15 also can generate light 25 to excite fluorescence from microorganisms that may be present on items 56, so that a sensing device 16 of the feedback component 14 can detect the microorganisms. Furthermore, the visible and/or IR source 15 can generate light 25 to facilitate a target (e.g., optimal) photocatalytic reaction for the catalyst 59.

As described herein, embodiments can be implemented as part of any of various types of storage systems. FIGS. 4A-4H show illustrative storage devices for use with an ultraviolet radiation system 10 (FIG. 1) according to embodiments. For example, the storage device can be a refrigerator and/or freezer (FIG. 4A) for storing a plurality of food items. Alternatively, the storage device can be a container for biological objects (FIG. 4B). The storage device can be a cooler (FIG. 4C), a backpack (FIG. 4D), a food container (FIG. 4E), a plastic bag (FIG. 4F), a lunchbox (FIG. 4G), a pantry (FIG. 4H, e.g., a shelf in the pantry), and/or the like. In each case, an embodiment of the system 10 can be implemented in conjunction therewith using any solution. To this extent, it is understood that embodiments of the system 10 can vary significantly in the number of devices, the size of the devices, the power requirements for the system, and/or the like. Regardless, it is understood that these are only exemplary storage devices and that the system 10 may be applicable to other storage devices not specifically mentioned herein.

Figure 5:
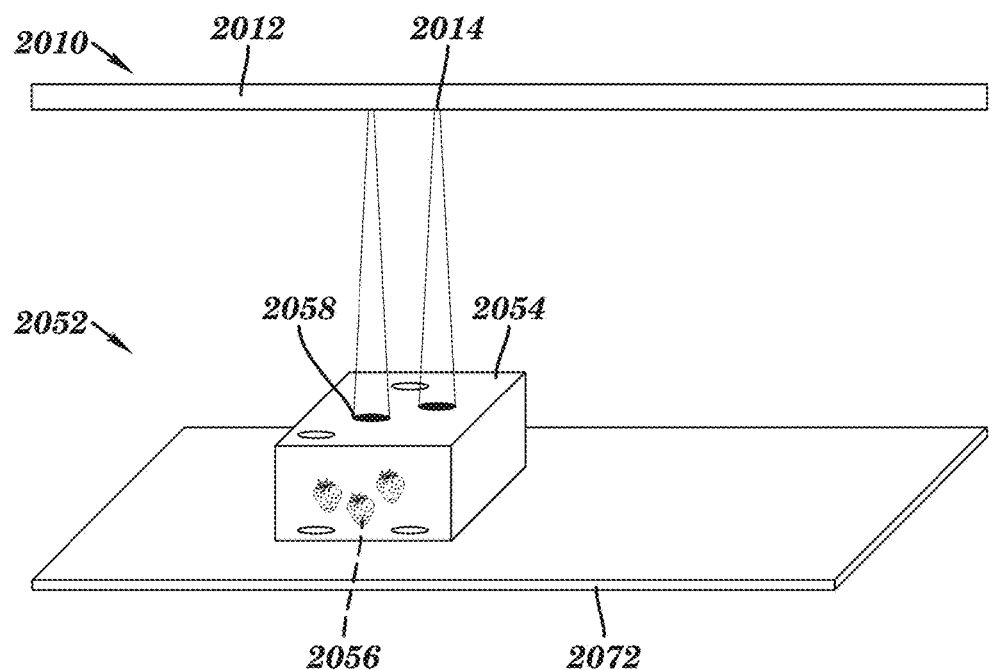
FIG. 5 shows an illustrative storage device for use with an ultraviolet radiation system according to an embodiment.

For example, in the embodiment shown in FIG. 5, a system 2010 can include a storage device 2052 with a shelf 2072. A set of boxes 2054 can be located on the shelf 2072. Although only one box 2054 is shown, it is understood that the storage device 2052 can include any number of boxes on the shelf 2072. Each box 2054 includes a set of openings 2058 that can be located anywhere on the surface of the box 2054. An ultraviolet radiation source 2012 is located above the shelf 2072 and includes a plurality of emitters 2014. The ultraviolet radiation source 2012 is configured to generate ultraviolet radiation in a pattern that corresponds to the location of the set of openings 2056 on the side of the box 2054 that faces the ultraviolet radiation source 2012, so that the ultraviolet radiation radiates onto the set of items 2056 within the box 2054. The location of the set of openings 2058 can be determined using a sensing device 16 (FIG. 3) (e.g., a visual camera). In another embodiment, the location of the set of openings 2058 can be determined using reflectivity measurements from the box 2054. For instance, the box 2054 can be scanned by a laser and the reflected light can be used to determine if the set of openings 2058 in the box 2054 have been located. Such measurements are well known in the art of 3D scanning, for example.

Figure 6:
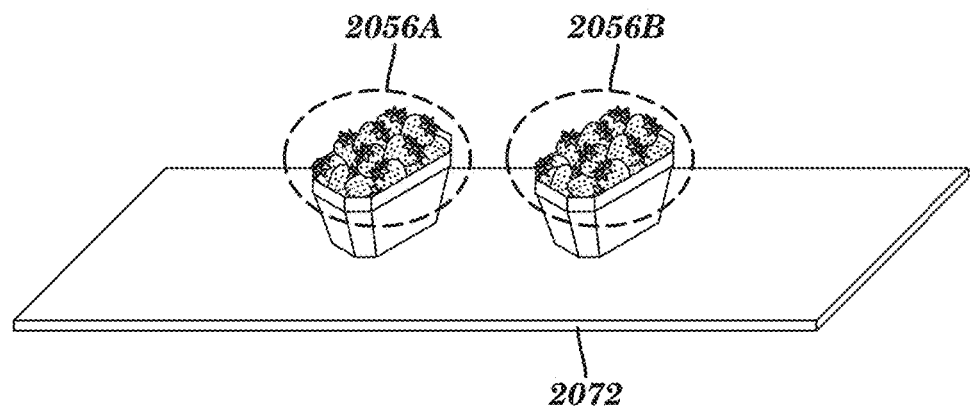
FIG. 6 shows an illustrative shelf including a set of items for use with an ultraviolet radiation system according to an embodiment.
Figure 7:
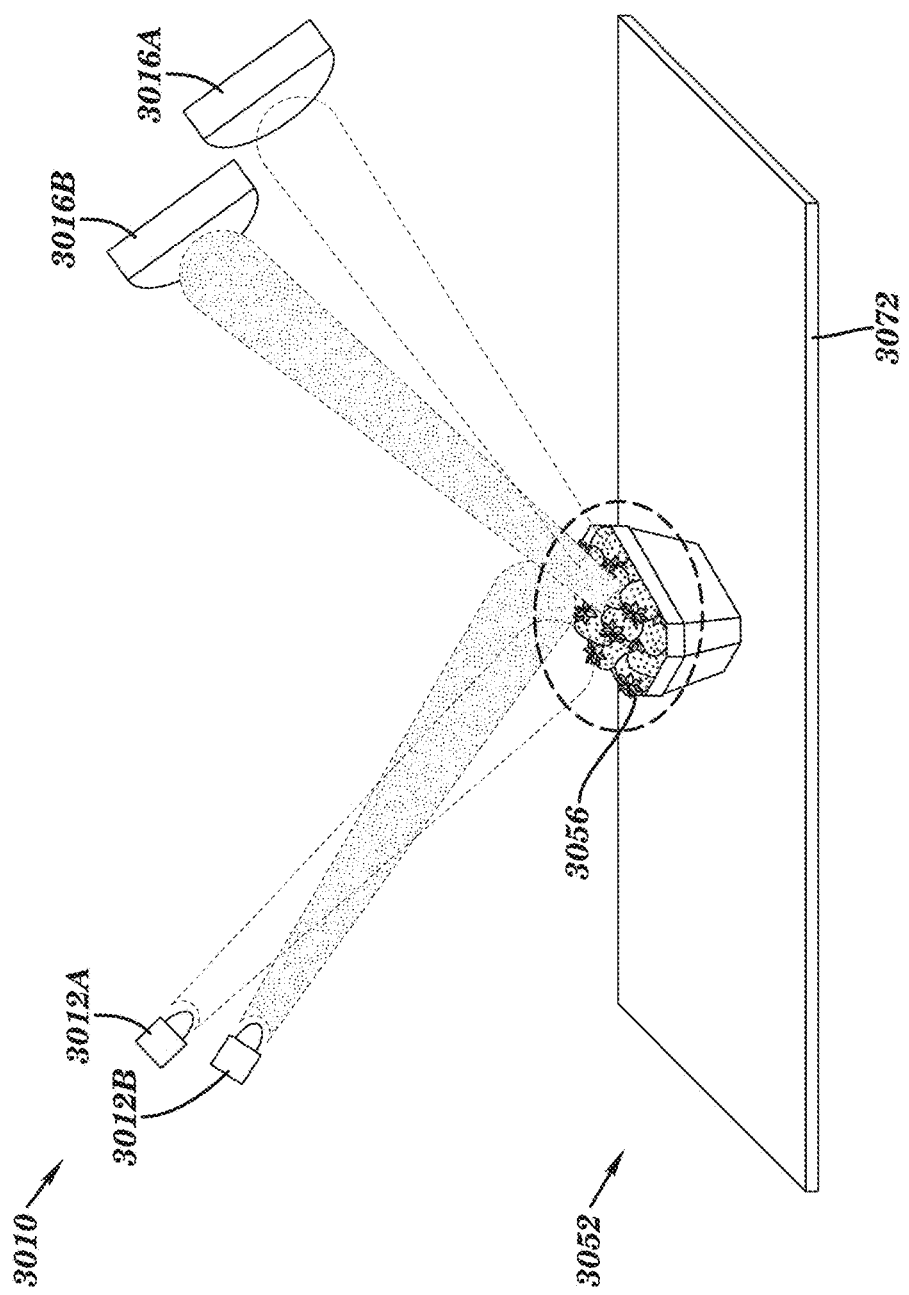
FIG. 7 shows an illustrative storage device for use with an ultraviolet radiation system according to an embodiment.

For a set of items with a short storage time (e.g., strawberries), exposing only a portion of the set of items to ultraviolet radiation can induce an overall beneficial effect on the storage life for the set of items. Turning now to FIG. 6, a first basket of strawberries 2056A and a second basket of strawberries 2056B are located on a shelf 2072. It is understood that this shelf 2072 can be located in any type of storage device described herein. Furthermore, although it is not shown, it is understood that the first and/or second basket of strawberries 2056A, 2056B can be located within a box, such as the box 2054 shown in FIG. 5. As mentioned above, the shelf 2072 can include a load sensor configured to detect the load (e.g., the weight), and an approximate volume, of the items 2056A, 2056B located on the shelf 2072. The sensing device 16 (FIG. 3) can also include a visual camera for detecting an exposed area of the set of items 2056A, 2056B. In an embodiment, if the exposed area is sufficient for inducing an overall preservation of one or more of the items 2056A, 2056B, then ultraviolet radiation is generated to treat the items 2056A, 2056B. If the exposed area is not sufficient for inducing an overall preservation of the items 2056A, 2056B, an alarm component 23 (FIG. 1) can generate an alarm to indicate that the items 2056A, 2056B should be spread out over a larger area before ultraviolet radiation is used. In an embodiment, fluorescent signals induced by radiation can be evaluated in order to determine a set of attributes regarding a set of items within the storage area. Turning now to FIG. 7, a system 3010 can include a set of ultraviolet radiation sources 3012A, a set of visible light sources 3012B, and a set of fluorescent sensors 3016A, 3016B. The first fluorescent sensor 3016A can be configured to detect a fluorescent signal due to the ultraviolet radiation from the set of ultraviolet radiation sources 3016A, while the second fluorescent sensor 3016B can be configured to detect a fluorescent signal due to the visible radiation from the set of visible light sources 3012B. In an embodiment, the fluorescent signal induced by each of the radiation sources are compared to determine the set of attributes regarding the set of items 3056, such as the presence of flavonoids, flavones, and/or the like. While the set of items 3056 are shown as located directly on a shelf 3072, it is understood that the set of items 3056 can be first placed in a storage area with walls (e.g., a box, such as the box 2056 in FIG. 7) in order to provide more control.

Figure 8A:
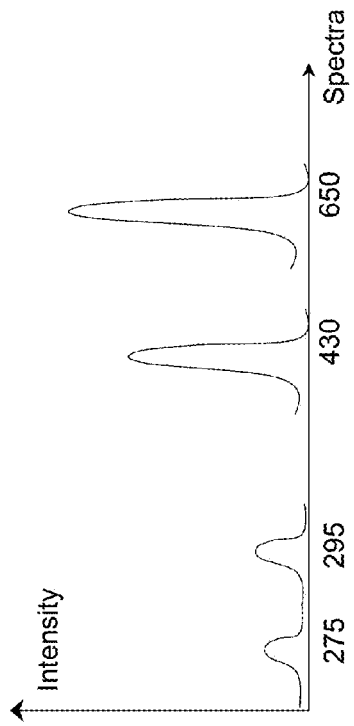

As seen in the flow chart of FIG. 8A, it is understood that other input parameters in addition to ultraviolet radiation and visible light can be used in a feedback loop (e.g., feedback component 14 in FIG. 3) to determine the set of attributes regarding the set of items within the storage area. For example, as seen in FIG. 8C, in addition to ultraviolet radiation and visible light, the input parameters can include adjusting a humidity (Water Input), a temperature (Air Temperature Input), a concentration of gas (e.g., ethylene, carbon dioxide ($CO_2$), and/or the like) (CO2 input), using an environmental control component 18 (FIG. 3). It is understood that the input parameters can be changed according to the sensing devices 16 (FIG. 3). The fluorescent signals are measured and used by the computer system (e.g., computer system 20 in FIG. 3) to determine the set of attributes. In an embodiment, a Fluorescent Test (FT), as known in the art, can be used. As shown in FIG. 8C, the set of items 3056 are first radiated by ultraviolet radiation using the set of ultraviolet radiation sources 3012A and then secondly radiated by visible light using the set of visible light sources 3012B. In FIG. 8C, the UV radiation is shown as shifted in phase with visible radiation. A first fluorescent signal is sensed using the first fluorescent sensor 3016A, and then a second fluorescent signal is sensed using the second fluorescent sensor 3016B. The ratio of the second and the first fluorescent signals (FT ratio) is used to determine the presence of flavonoids. Large ratios indicate a larger presence of flavonoids, while smaller ratios indicate a smaller flavonoid content.

Figure 8B:
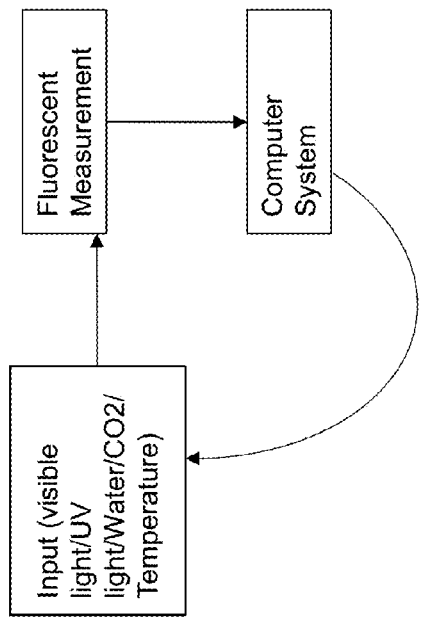
FIG. 8B shows illustrative peak wavelengths for ultraviolet and visible radiation according to an embodiment.
Figure 8C:
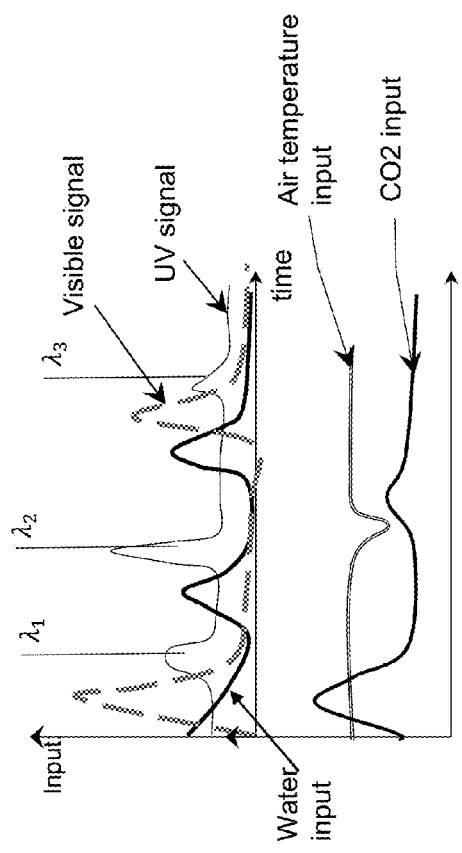
FIG. 8C shows an exemplary plot of changing input parameters according to an embodiment.

As seen in FIG. 8B, the set of ultraviolet radiation sources 3012A (FIG. 7) can include peak wavelengths at 275 nm and 295 nm, while the set of visible light sources 3012B (FIG. 7) can include peak wavelengths at 430 nm and 650 nm. The UV peak wavelengths are responsible for disinfection and food preservation, and visible light can promote physio-chemical response in the plant such as photosynthesis.

Figure 9:
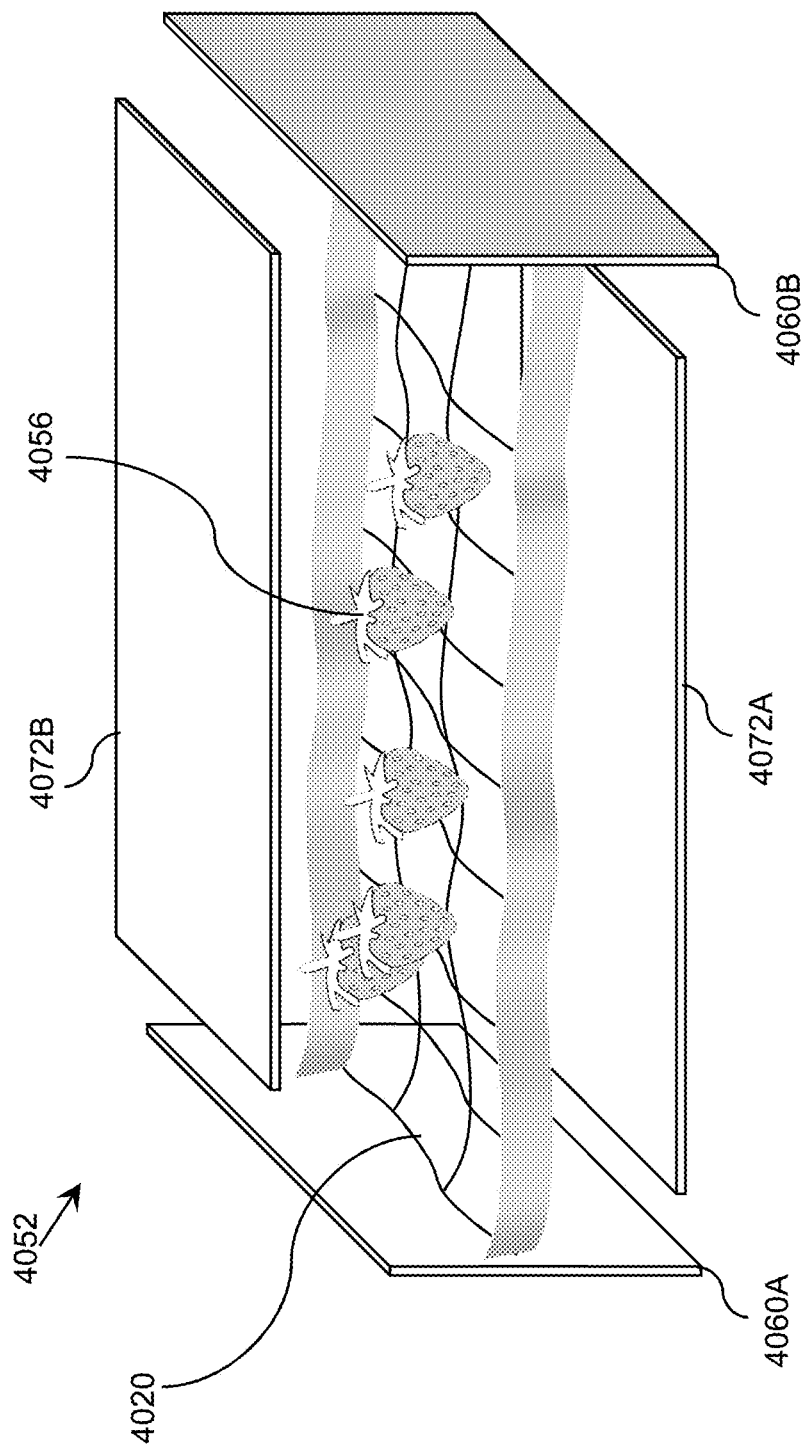
FIG. 9 shows an illustrative storage device for use with an ultraviolet radiation system according to an embodiment.

Turning now to FIG. 9, a storage area 4052 according to another embodiment is shown. In this embodiment, the radiation exposure area for the set of items 4056 can be increased in order to increase the beneficial effects of the radiation. In this embodiment, the storage area 4052 includes a net 4020 that is suspended between a first wall 4060A and a second wall 4060B. In this embodiment, a bottom shelf 4072A and a top shelf 4072B can be located under and over the net 4020. Each of the shelves 4072A, 4072B can include a set of ultraviolet radiation sources (not shown) in order to direct ultraviolet radiation at the set of items 4056 from both the top and the bottom.

Figure 10:
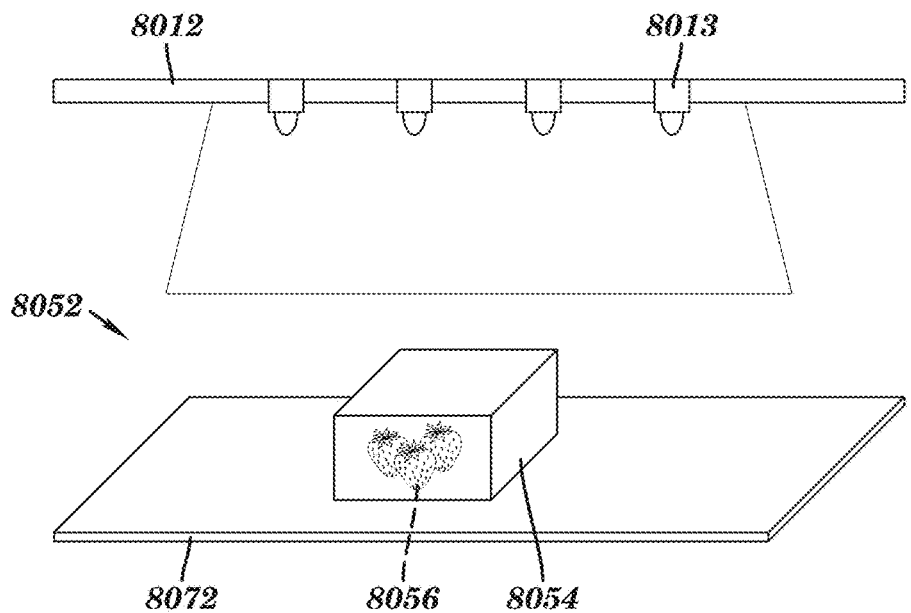
FIG. 10 shows an illustrative storage device for use with an ultraviolet radiation system according to an embodiment.

Turning now to FIG. 10, an illustrative storage device 8052 according to another embodiment is shown. In this embodiment, an ultraviolet radiation source 8012 including a plurality of emitters 8013 is positioned over a shelf 8072. A storage container (e.g., box) 8054 including a set of items (e.g., strawberries) 8056 is located on top of the shelf 8072. Although only one storage container 8054 is shown on the shelf 8072, it is understood that any number of storage containers can be located on the shelf. In an embodiment, the storage container 8054 may be formed of a UV transparent material, such as a UV transparent fluoropolymer, so that the set of items 8056 located within the storage container 8054 can be exposed to the ultraviolet radiation generated by the ultraviolet radiation source 8012. For example, the storage container 8054 can be formed of polytetrafluoroethylene (PTFE), fluorinated ethylene propylene (FEP) resin, ethylene chlorotrifluoroethylene (ECTFE), polychlorotrifluoroethene (PCTFE), perfluoroalkoxy alkanes (PFA) resins, polyvinylidene difluoride (PVDF), ethylene tetrafluoroethylene (ETFE), MFA, ethylene tetrafluoroethylene hexafluoropropylene fluoroterpolymer (EFEP), THV, HTE, silicon-based polymers, quarts, cellophane, and/or the like. In an embodiment, the storage container 8054 can be formed of any material that is partially transparent to radiation in the wavelength range of 200-380 nanometers. In an embodiment, for a storage container wall formed of a thin film of material (e.g., approximately 200 microns or less), the transmission rate can be at least 30%.

Polytetrafluoroethylene (PTFE) is a polymer including recurring tetrafluoroethylene monomer units whose formula is [CF2-CF2]n. PTFE does not melt to form a liquid and cannot be melt extruded. On heating the virgin resin, it forms a clear, coalescent gel at 626° F. ±18° (330° C. ±15°). Once processed, the gel point (often referred to as the melting point) is 18° F. (10° C.) lower than that of the virgin resin. PTFE is generally sold as a granular powder, a fine powder, or an aqueous dispersion. Each is processed in a different manner.

Fluorinated ethylene propylene (FEP) resin is a copolymer of tetrafluoroethylene and hexafluoropropylene with the formula [(CF(CF3)-CF2)x(CF2-CF2)y]n. FEP has a melting point range of 473°-536° F. (245°-280° C.) and is melt processable. FEP is supplied in the form of translucent pellets, powder, or as an aqueous dispersion.

Ethylene chlorotrifluoroethylene (ECTFE) is a copolymer of ethylene and chlorotrifluoroethylene having the formula [(CH2-CH2)x-(CFCl-CF2)y]n. ECTFE has a melting point range of 428°-473° F. (220°-245° C.) and is melt processable. ECTFE is available in the form of translucent pellets and as a fine powder.

Polychlorotrifluoroethene (PCTFE) is a polymer of chlorotrifluoroethylene with the formula [CF2-CFCl]n. PCTFE has a melting point range of 410°-428° F. (210°-220° C.) and is melt processable. PCTFE is available in pellet, granular and powder form.

Perfluoroalkoxy alkanes (PFA) resins are copolymers of TFE fluorocarbon monomers containing perfluoroalkoxy side chains. PFA melts at 536° F. (280° C.) minimum and is melt processable. PFA is available in the form of pellets, powder, and as an aqueous dispersion.

Polyvinylidene difluoride (PVDF) is a homopolymer of vinylidene fluoride having the formula [CH2-CF2]n or a copolymer of vinylidene fluoride and hexafluoropropylene having the formula [CF(CF3)-CF2)x(CH2-CF2)y]n. Copolymers of vinylidene fluoride are also produced with (1) chlorotrifluoroethylene, (2) tetrafluoroethylene, and (3) tetrafluoroethylene and hexafluoropropylene. These are all sold as PVDF copolymers. PVDF polymers/copolymers melt at 194°-352° F. (90°-178° C.), are melt processable, and are supplied in the form of powder, pellets, and dispersions.

Ethylene tetrafluoroethylene (ETFE) is a copolymer of ethylene and tetrafluoroethylene of the formula [(CF2-CF2)x-(CH2-CH2)y]n. ETFE melts at 428° F. (220° C.) minimum. ETFE is melt processable and is supplied in pellet and powder form. A fluorine based plastic, ETFE (ethylene tetrafluoroethylene) offers impressive corrosion resistance and strength over a very wide temperature range. Since ETFE is melt processable, it can be utilized in a vast range of applications.

MFA is a copolymer of tetrafluoroethylene and perfluoromethylvinylether. MFA belongs to the generic class of PFA polymers. MFA melts at 536°-554° F. (280°-290° C.). MFA is available in the form of translucent pellets and aqueous dispersions.

Ethylene tetrafluoroethylene hexafluoropropylene fluoroterpolymer (EFEP) is a copolymer of ethylene, tetrafluoroethylene, and hexafluoropropylene with the formula [(CH2-CH2)x(CF2-CF2)y(CF(CF3)-CF2)z]n. EFEP polymers melt at 311°-464° F. (155-240° C.), are melt processable, and are supplied in pellet form.

THV is a copolymer containing tetrafluoroethylene, hexafluoropropylene and vinylidenefluoride. THV is melt-processable with melting points from 240° to 455° F. (115° to 235° C.) depending on grade. THV is available in pellet, agglomerate or aqueous dispersions.

HTE is a copolymer of hexafluoropropylene, tetrafluoroethylene, and ethylene. HTE is melt processable with melting points from 310° to 420° F. (155° to 215° C.) depending on grade, and is available in pellet or agglomerate form.

Some illustrative fluoropolymers are marketed under the brand names Teflon® AF (an amorphous fluoroplastic) offered by E. I. du Pont de Nemours and Company and Cytop® (an amorphous fluoropolymer) offered by Bellex International Corporation, which are currently sold as liquid solutions or gels.

In an embodiment, an optoelectronic device can include an ultraviolet transparent fluoropolymer, such as one of fluoropolymers discussed herein. In a more specific embodiment, the optoelectronic device operates at a peak ultraviolet wavelength. Several important factors for materials utilized in packaging an ultraviolet optoelectronic device include: transparency to ultraviolet radiation; stability to exposure to ultraviolet radiation, which can translate into a long operating lifetime for the material and the device without significant changes in optical, mechanical or chemical properties; a capability to protect the device from the environment, which can include mechanical dexterity and chemical inertness; and adhesion to surfaces of the optoelectronic device. In a more specific embodiment, a highly ultraviolet transparent fluoropolymer is utilized in the packaging. Such polymers are available and have a long lifetime when exposed to ultraviolet light.

However, it is understood that aspects of the invention are not limited to any particular material or group of materials listed herein. To this extent, numerous other materials or their combinations and solutions exist which can have appropriate properties and be utilized as described herein. For example, various polymers can be mixed, and various additional compounds can be added to the polymers (primarily when in the melted stage) to alter their mechanical, thermal, chemical and/or optical properties.

Furthermore, it is understood that other UV transparent materials (besides fluoropolymers) can be used to form the storage container 8054. In an embodiment, such materials can include silicon dioxide ($SiO_2$) containers, other UV transparent glass containers, and/or the like.

Figure 11:
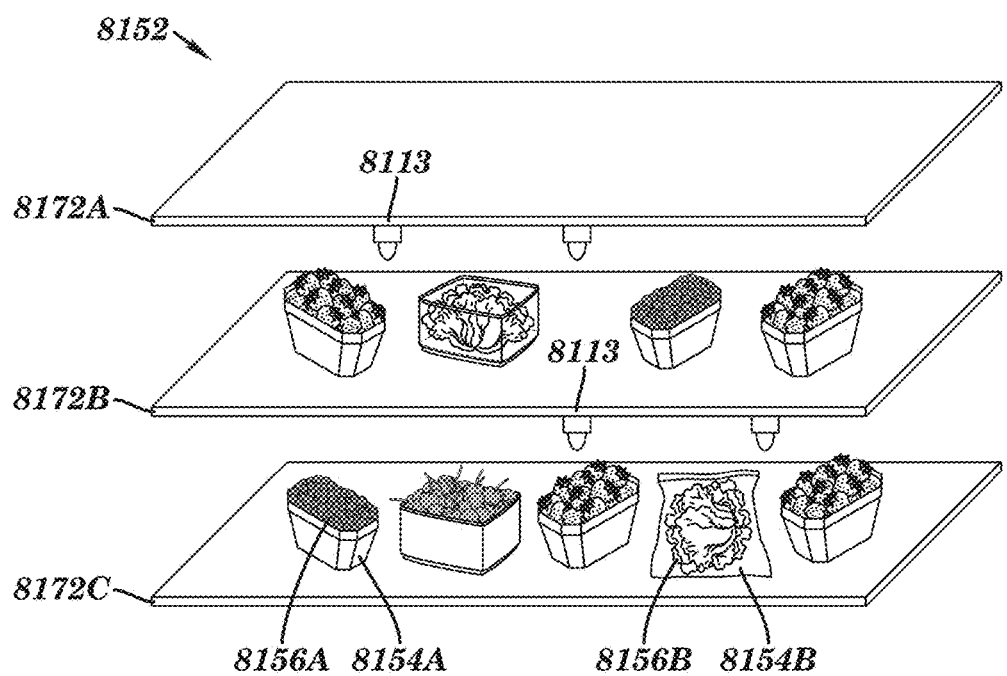
FIG. 11 show an illustrative storage device for use with an ultraviolet radiation system according to an embodiment.

Turning now to FIG. 11, an illustrative storage device 8152 according to another embodiment is shown. In this embodiment, the storage device 8152 can include a plurality of shelves 8172A-C. Although three shelves are shown, it is understood that the storage device 8152 can include any number of one or more shelves. It is also understood that each of the plurality of shelves 8172A-C can hold any number of items 8156A-B. The items 8156A-B can be any item susceptible to spoilage, including but not limited to food items, such as strawberries, blueberries, lettuce, cherries, and/or the like, that are affected by UV radiation that spans all wavelengths including UV-C, UV-B, and UV-A wavelengths. Any of the items 8156A-B can be contained within a UV transparent container 8154A-B, similar to the storage container 8054 shown in FIG. 10. In an embodiment, the spacing between each shelf 8172A-C is adjusted so that the vertical distance between the plurality of shelves 8172A-C is larger than the height of the container 8154A-B and the items 8156A-B. In an embodiment, all of the shelves except for the last shelf (e.g., shelves 8172A and 8172B and not shelf 8172C can include a set of ultraviolet radiation emitters 8113. For example, the set of ultraviolet radiation sources can be located on the bottom of each shelf 8172A-B and radiate ultraviolet radiation directed down towards the set of items 8156A-B located below each shelf 8172A-B, so only shelves 8172A-B would include the set of ultraviolet radiation sources.

Turning now to FIG. 12A, an illustrative ultraviolet radiation source 8212 according to an embodiment is shown. It is understood that the ultraviolet radiation source 8212 can be included in the ultraviolet radiation system for any storage device discussed herein. The ultraviolet radiation source 8212 includes a set of ultraviolet light emitting diodes 8214 and electronic drivers 8216 configured to deliver a specific power and time schedule to each of the ultraviolet light emitting diodes 8214. In FIG. 12B, an illustrative ultraviolet transparent enclosure 8218 for enclosing the ultraviolet radiation source 8212 according to an embodiment is shown. The ultraviolet transparent enclosure 8218 can be formed of any ultraviolet transparent material (e.g., a fluoropolymer). In an embodiment, the ultraviolet transparent enclosure 8218 is anti-befouled, wherein anti-befouled is defined as a surface that resists befouling.

Turning now to FIG. 13, an exemplary power distribution plot from several ultraviolet radiation sources is shown. In this embodiment, the ultraviolet radiation sources are positioned in parallel. The ultraviolet radiation sources are designed to deliver a relatively uniform intensity of illumination at a distance characteristics to the distance between the ultraviolet radiation source and the item to be disinfected. In an embodiment, the ultraviolet radiation source can provide a means for gradual changes of the ultraviolet exposure wavelength and intensities as functions of storage time. Feedback data can be acquired through the use of optical or fluorescent sensors that can detect the evolution of the produce during the produce storage. Such sources and detectors can be operated based on the changes in observed color, changes of fluorescence, identification of color changes at various places over the surfaces, and/or the like. In general, as discussed herein, the ultraviolet radiation source may include UV-A and/or violet light, as well as visible and/or infra-red illuminating sources for produce treatment, sensing of changes in color, as well as to illuminate the item in a favorable light for customer satisfaction. It is understood that radiation patterns can be adjusted, depending on the type of item (e.g., produce) present at a specific location. In such a case, the ultraviolet radiation system can include a set of optical sensors capable of image recognition.

It is understood that different storage devices can be used to store items for use with an ultraviolet radiation system according to embodiments discussed herein. For example, turning now to FIG. 14, an illustrative storage device 8352 according to an embodiment is shown. The storage device 8352 includes a basket 8360, a first cover 8362 located over the basket 8360, and a second cover 8364 located over the first cover 8362. The basket 8360, the first cover 8362, and the second cover 8364 can all be formed of a mesh and the openings in the mesh can be as large as 99% of the surface area of the first cover 8362. The mesh is designed with an opening with a characteristics size that is smaller than a characteristic size of an item (not shown) stored within the basket 8360 to ensure that basket 8360 can contain the items, while still allowing ultraviolet radiation to go through the openings. The mesh can be of any suitable material that can support holding the item. For instance, the mesh can be made of plastic, fiberglass, or metal.

Turning now to FIG. 15, an illustrative mesh 8366 according to an embodiment is shown. The mesh 8366 can be used to fabricate one or more of the components of the storage device 8352 shown in FIG. 14. For example, the mesh 8366 can be used for the first cover 8362 in FIG. 14. The mesh 8366 is formed of an ultraviolet transparent material and has an elastic rubber siding 8368 so that the mesh 8366 can be securely placed around the basket 8360 in FIG. 14. In an embodiment, the elastic rubber siding 8368 can be automatically placed around a mesh basket 8360 or any suitable storage device as discussed herein, e.g., by using a robotic system. The elasticity and strength of the elastic rubber siding 8368 is selected to be commensurate with the strength of the walls of the storage device 8352 to make sure that the elastic rubber siding 8368 does not crumble the storage device 8352.

Figure 16:
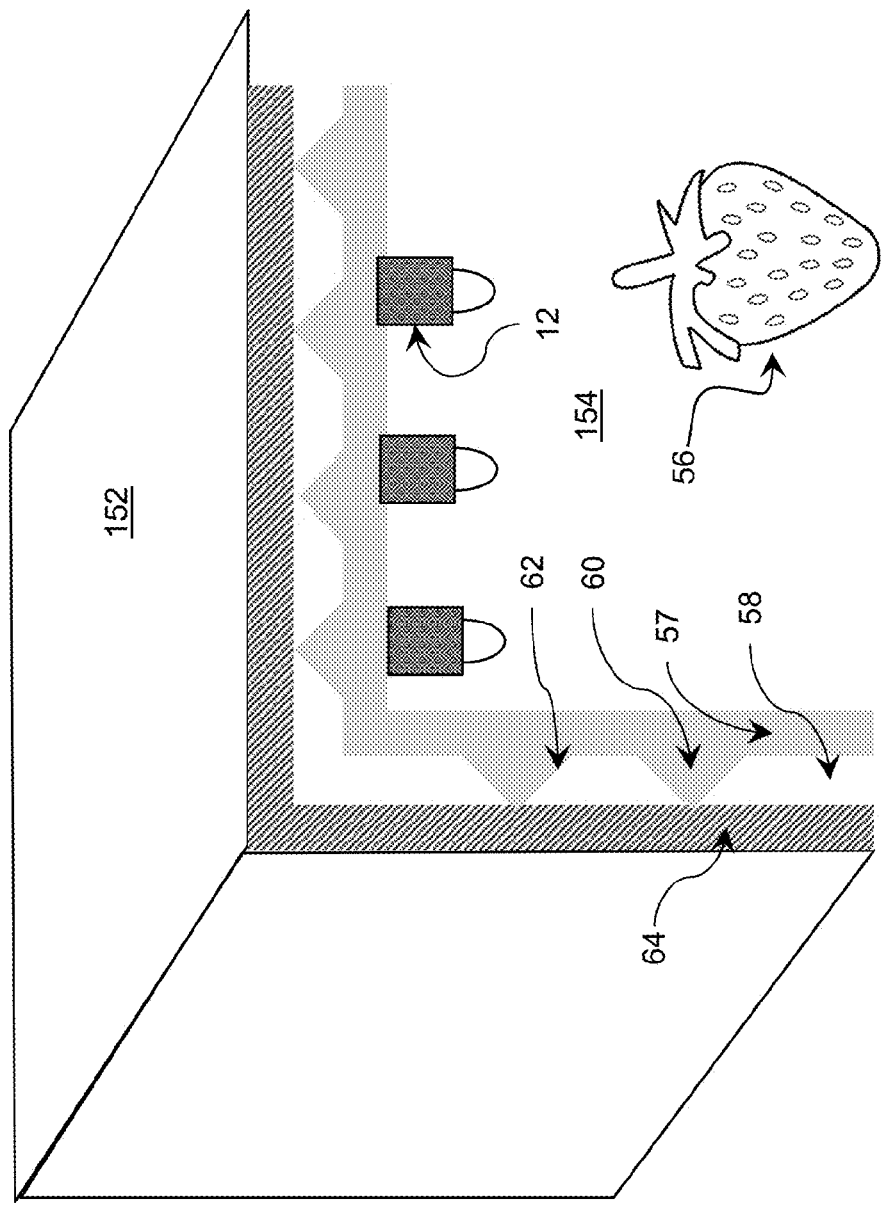
FIG. 16 shows a partial cross-sectional perspective view of an illustrative storage device according to an embodiment.

In an embodiment, the ultraviolet radiation source 12 can include a plurality of ultraviolet light emitters located in various locations adjacent to a storage area. To this extent, FIG. 16 shows a partial cross-sectional perspective view of an illustrative storage device 152 according to an embodiment. The storage device 152 includes a storage area 154 for containing at least one item 56. As shown in the figure, a plurality of ultraviolet radiation emitters 12 are located within the storage area 154. The storage device 152 can be comprised of multiple layers. The layers can protect other storage areas and/or components of the storage device 152 from ultraviolet radiation and/or increase the efficiency of the ultraviolet radiation within the storage area 154. The layers do not allow UV radiation to escape from the storage area 154. For example, an ultraviolet transparent wall 57 can surround the storage area 154 within which the ultraviolet radiation emitters 12 are located. A hollow region 58 can be located between the ultraviolet transparent wall 57 and a highly reflective wall 64.

The highly reflective wall 64 can reflect and/or absorb the UV radiation. The highly reflective wall can include a reflectivity of more than approximately 50% as measured for the UV radiation at the normal incidence direction. Approximately 20% of the volume of the hollow region 58 can include a refractive index lower than that of the ultraviolet transparent wall 57. A plurality of elements 60 can protrude from the ultraviolet transparent wall 57 into the hollow region 58. The plurality of elements 60 can include high/low index interfaces 62. During operation, once the ultraviolet radiation emitters 12 shine ultraviolet light into the storage area 154, the high/low index interfaces 60 and the highly reflective wall 64 reflect ultraviolet light back into the storage area 154. The ultraviolet transparent wall 57 can be made of one or more materials that allow ultraviolet radiation to pass through, such as fused silica, an amorphous fluoroplastic (e.g., Teflon by Dupont), and/or the like. Other illustrative materials include alumina sol-gel glass, alumina aerogel, sapphire, aluminum nitride (e.g., single crystal aluminum nitride), boron nitride (e.g., single crystal boron nitride), and/or the like. The outer reflective wall 64 can be made of one or more materials that reflects ultraviolet radiation, such as polished aluminum, a highly ultraviolet reflective expanding polytetrafluoroethylene (ePTFE) membrane (e.g., GORE® Diffuse Reflector Material), and/or the like.

Figure 17:
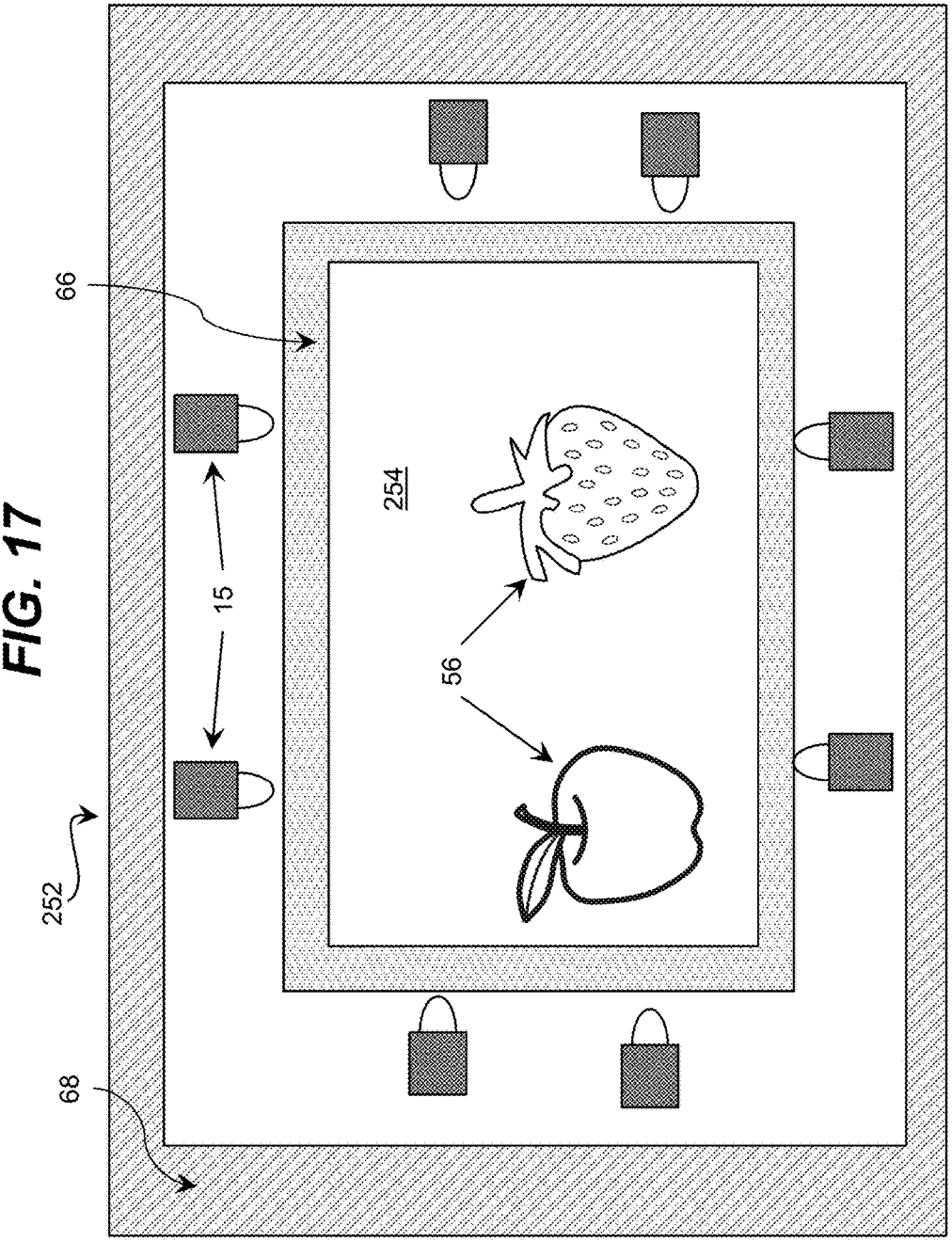
FIG. 17 shows a cross-sectional view of an illustrative storage device according to an embodiment.

FIG. 17 shows a cross-sectional view of another illustrative storage device 252 according to an embodiment. The storage device 252 is shown including an inner ultraviolet radiation transparent enclosure 66 surrounding a storage area 254. The inner ultraviolet radiation transparent enclosure 66 allows ultraviolet radiation emitted from ultraviolet radiation emitters 12 to reach items 56 located within the storage area 254. An outer ultraviolet radiation reflective wall 66 surrounds the inner ultraviolet radiation transparent enclosure 66 and blocks the ultraviolet radiation from exiting the storage device 252. The ultraviolet radiation emitters 12 can be located between the inner ultraviolet radiation transparent enclosure 66 and the outer ultraviolet radiation reflective wall 68.

Figure 18:
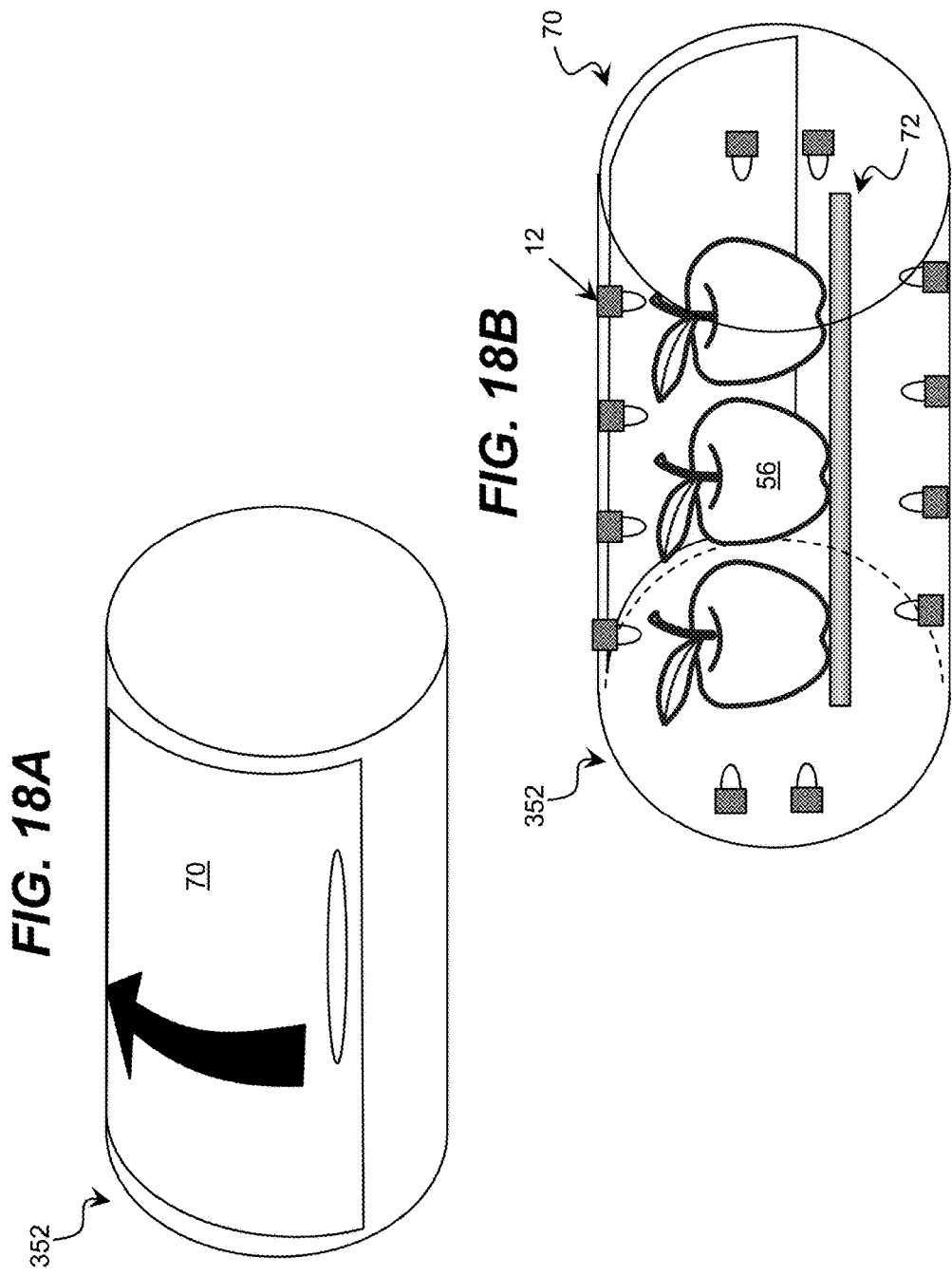
FIGS. 18A and 18B show perspective views of illustrative storage devices according to embodiments.

FIGS. 18A and 18B show perspective views of illustrative storage devices 352 according to other embodiments. In this case, each storage device 352 is shown as having a cylindrical shape. The cylindrical shape for the storage device 352 can allow for increased reflectivity of ultraviolet radiation back into the storage area 354 and onto the stored items from various sides/angles. Furthermore, the cylindrical shape can increase the surface area of items 56 that are exposed to ultraviolet radiation. The cylindrical shaped storage device 352 can be utilized to store, for example, medium sized round food items, such as apples, tomatoes, and/or the like. However, it is understood that the storage device 352 can include any shape and size. The storage device 352 in FIGS. 18A and 18B includes a sliding door 70 for access to the storage area within which items 56 may be located.

Figure 19:
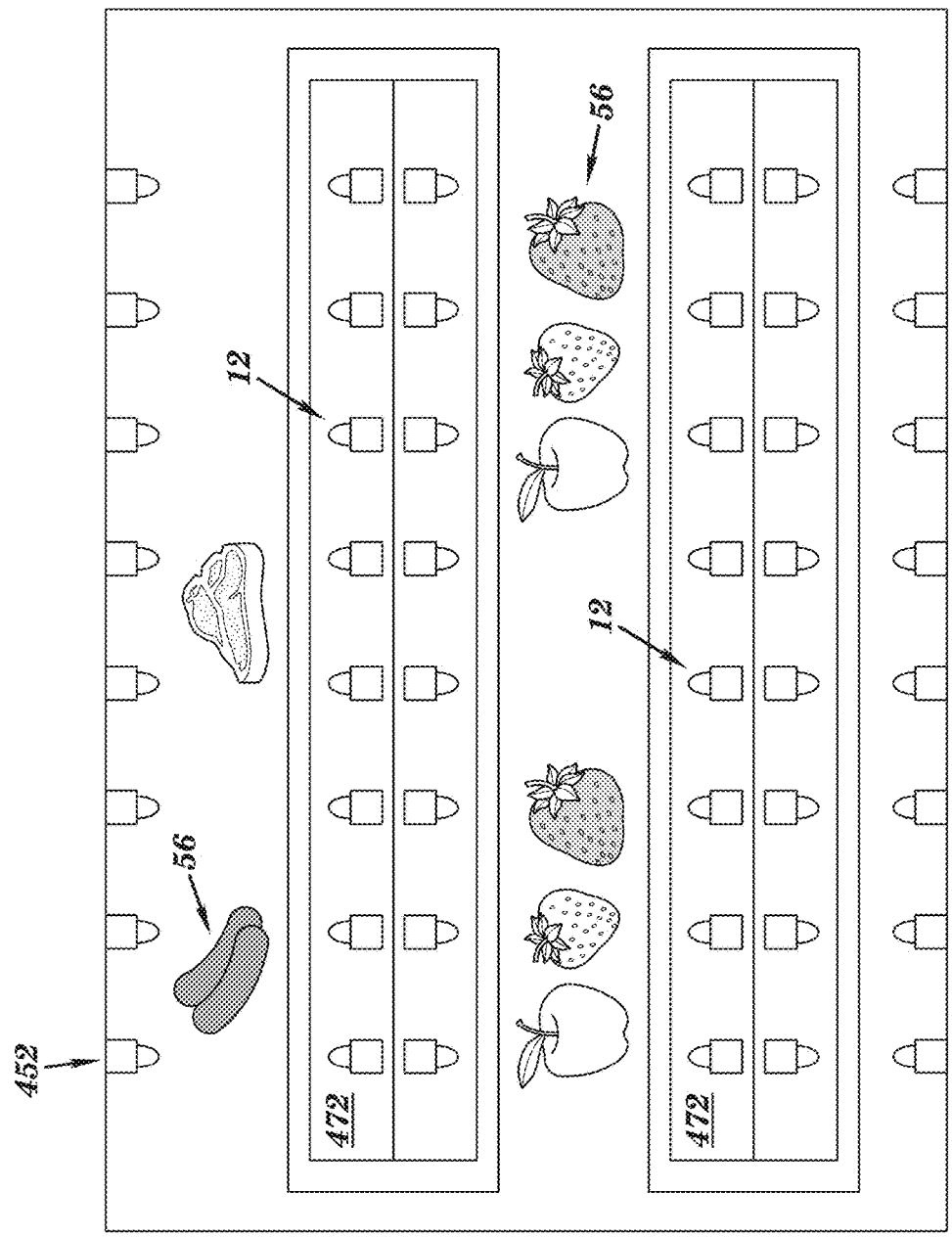
FIG. 19 shows a cross-sectional view of an illustrative storage device according to an embodiment.

A computer system 20 (FIG. 1) can be configured to control the ultraviolet radiation sources 12, such that when sliding door 70 is opened, the ultraviolet radiation sources 12 are turned off. Once sliding door 70 is closed, the ultraviolet radiation sources 12 are turned back on. Although not shown, the storage device 352 may also include an inner ultraviolet radiation transparent enclosure and an outer ultraviolet radiation reflective wall, as shown and described herein. Furthermore, the storage device 352 can include a shelf 72 for the items 56. In an embodiment, the shelf 72 is formed of an ultraviolet radiation transparent material so that the items 56 located on the shelf 72 can be subjected to ultraviolet radiation from any direction. FIG. 19 shows a cross-sectional view of an illustrative storage device 452 according to an embodiment. In this case, the storage device 452 includes a plurality of ultraviolet radiation transparent shelves 472 for a plurality of items 56. The shelves 472 can be entirely or only partially located within the storage device 452. Additionally, the ultraviolet radiation sources 12 can be located within each of the ultraviolet radiation transparent shelves 472.

FIGS. 20A and 20B show cross-sectional views of illustrative storage devices 552, 652, respectively, according to still other embodiments. In this case, the plurality of ultraviolet radiation transparent shelves 572, 672, respectively, include a plurality of dimensioned depressions 74. The dimensioned depressions 74 can be sized for any desired item to be stored thereon. For example, in FIG. 20A, the dimensioned depressions 74 are sized for strawberries 54. In FIG. 20B, the dimensioned depressions 74 are sized for blueberries 54. The dimensioned depressions 74 can also be sized, for example, for raspberries, kiwi fruit, broccoli, cauliflower, and/or the like. While each shelf 572, 672 is shown having multiple depressions of the same size, it is understood that a shelf 572, 672 can have any number of depressions of any of various sizes. The dimensioned depressions 74 can be configured to increase an amount of power of the ultraviolet radiation directed onto the item(s) stored therein. For example, a transparent depression can allow ultraviolet light to pass through the sides of the depression directed toward the stored item. Additionally, the depressions can prevent the stored items from touching one another, thereby increasing an amount of the surface area that can be illuminated by ultraviolet radiation.

Figure 21:
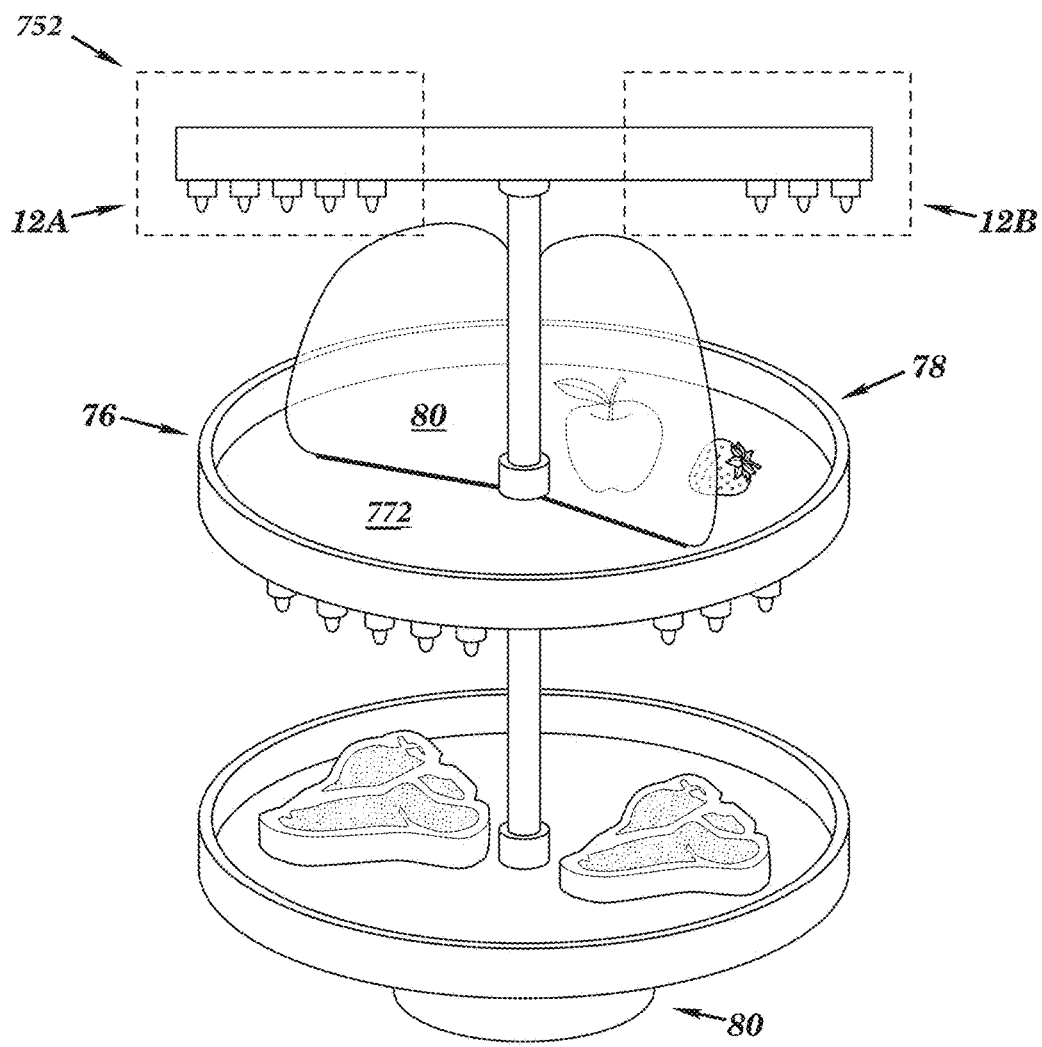
FIG. 21 shows a perspective view of an illustrative storage device according to an embodiment.

FIG. 21 shows a perspective view of an illustrative storage device 752 according to an embodiment. In this embodiment, the storage device 752 can include a plurality of sub-compartments that are individually/separately monitored by the computer system 20 (FIG. 1) using the feedback component 14 (FIG. 1). It is understood that the plurality of sub-compartments can be located within an inner ultraviolet radiation transparent enclosure, such as the enclosure 66 shown in FIG. 17. Furthermore, the ultraviolet radiation sources 12 in each sub-compartment can be individually controlled by the computer system 20. For example, a shelf 772 can be partitioned into a first sub-compartment 76 and a second sub-compartment 78, which are separated by a divider 80. Each of the plurality of sub-compartments 76, 78 can include the same type of UV sources 12.

Alternatively, as shown in FIG. 21, the first sub-compartment 76 can include a first type of UV source 12A, and the second sub-compartment 78 can include a second type of UV source 12B. The computer system 20 can control the UV sources 12A, 12B, such that the first sub-compartment 76 is subjected to a first operating configuration and the second sub-compartment 78 is subjected to a second operating configuration. The particular operating configuration for each sub-compartment can differ. Furthermore, the computer system 20 can control the UV source 12A to have a first intensity and a first wavelength, and control the UV source 12B to have a second intensity and a second wavelength. For example, the UV source 12A can include a full intensity, while the UV source 12B includes a zero intensity. Conversely, the UV source 12A can include a zero intensity, while the UV source 12B includes a full intensity. Furthermore, the computer system 20 can independently tune the relative intensities of each UV source 12A, 12B, and either UV source 12A, 12B can have any intensity between zero and full.

Additionally, the shelves 772 may revolve, e.g., via a motor 80. The motor 80 may be controlled by the computer system 20 and rotate according to a timing schedule, such that the first sub-compartment 76 and the second sub-compartment 78 each receive ultraviolet light emitted by one of the UV sources 12A, 12B according to a particular operating configuration at a specific time. Although UV sources 12A, 12B are shown as mounted above the shelf 772, it is understood that UV sources can also be within the shelf 772, below the shelf 772, and/or the like.

Figure 22:
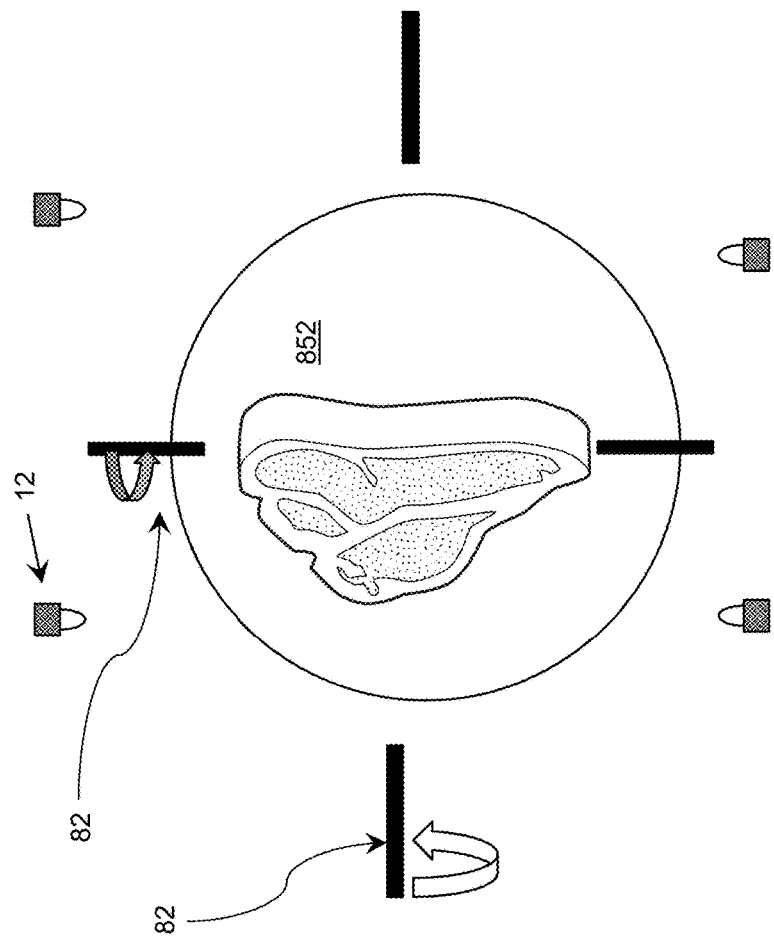
FIG. 22 shows a perspective view of an illustrative storage device according to an embodiment.

FIG. 22 shows a perspective view of another illustrative storage device 852 according to an embodiment. The storage device 852 can be attached to a gyroscopic suspension 82 so that the storage device 852 can rotate. As the storage device 852 rotates, ultraviolet radiation from ultraviolet radiation sources 12 can thoroughly illuminate any items located within the storage device 852 from all angles.

Returning to FIG. 3, it is understood that the system 10 may include a power component 19 that is implemented separately from the storage device 52 to supply power to one or more of the various components of system 10, such as ultraviolet radiation sources 12, motor 80 (FIG. 21), feedback component 14, computer system 20, and/or the like. For example, the storage device 52 may comprise a cooler or the like, which does not include or otherwise require any power source. Furthermore, the storage device 52 may comprise a power source that is insufficient to operate the various devices of system 10 in addition to maintaining one or more aspects of the environment within the storage area 54 for a desired period of time. Regardless, the power component 19 can be utilized to operate system 10. The power component 19 can comprise any source of power including, but not limited to, the power grid, a battery set, an automotive charger, a solar cell, and/or the like. In an embodiment, the computer system 20 can implement multiple modes of operation depending on the source of power. In particular, when a power component 19 of limited capacity is being utilized, one or more functions of system 10 can be disabled and/or reduced to lengthen an operating time for system 10. For example, use of ultraviolet radiation source 12 to prolong the life of items within the storage area 54 or disinfect the storage area 54 by generating a higher intensity of ultraviolet radiation can be disabled.

An environment within the storage area 54 can be controlled by an environmental control component 18. In an illustrative implementation, the environmental control component 18 can comprise a temperature control module, a humidity control module, and/or a convection control module. During normal operation of the environmental control component 18, a user 6 (FIG. 1) (e.g., using external interface component 26B) can select a desired temperature, humidity, and/or the like, to maintain within storage area 54. The environmental control component 18 can subsequently operate one or more cooling/heating components of temperature control module to maintain the desired temperature, operate one or more humidifying/dehumidifying components of humidity control module to maintain the desired humidity, operate one or more air or fluid convection components (e.g., fan, pump, vent, valve, etc.) of convection control module to assist in maintaining a relatively even temperature/humidity within storage area 54, and/or the like. Alternatively, local temperature control within storage area 54 can be maintained by cool air recirculation that is controlled by the environmental control component 18.

In an embodiment, the sensing device 16 can also include a humidity sensor that is configured to detect a humidity level within the storage area 54. In an embodiment, the computer system 20 can adjust the humidity level via the environmental control component 18 based on the weight distribution of the items 56 located within the storage area 54 (e.g., based on the data received by a load sensor). The sensing device 16 can also include a temperature sensor that is configured to detect a temperature within the storage area 54. In an embodiment, the temperature at which ultraviolet radiation is generated is at room temperature or at a temperature in the range of room temperature to a standard refrigerator's temperature. For example, the temperature of the storage area 54 can be approximately 70 degrees Fahrenheit, which is the temperature that is typically maintained in a grocery store. In an embodiment, the sensing device 16 can also include an ozone sensor. The ozone sensor can be configured to detect a level of ozone within the ambient. The ozone sensor can be located close to the ultraviolet radiation sources 12 for ozone level control.

The computer system 20 can be configured to adjust one or more operating parameters of the environmental control component 18 based on a set of current conditions in the storage area 54 and/or an operating configuration of the UV radiation source 12. For example, the computer system 20 can adjust one or more of: a temperature, a humidity, a gas convection, and/or a fluid convection of the storage area 54 in response to a set of biological activity dynamics and according to a currently selected operating configuration. In an embodiment where the storage area 54 includes a plurality of sub-compartments (e.g., FIG. 21), the computer system 20 can individually control the temperature, humidity, gas chemical composition, UV intensity and spectra in each sub-compartment. To this extent, each operating configuration can further define a set of target environmental conditions for use during the UV illumination. Such environmental conditions can include a target temperature, a target humidity, additional illumination by non-ultraviolet sources (e.g., visible, infrared), air circulation, and/or the like.

Furthermore, one or more of the environmental conditions can change over time during implementation of the operating configuration. In an illustrative embodiment, the computer system 20 can operate the environmental control component 18 to circulate air into the chamber 55, e.g., during implementation of the ethylene decomposition operating configuration. Furthermore, the set of current conditions in the storage area 54 can include an operating condition of one or more components of the system 10, such as the ultraviolet radiation source(s) 12. Information regarding the operating condition can be used to, for example, notify a user 6 of a problem using the alarm component 23, alter one or more aspects of an operating configuration, and/or the like. Additionally, the set of current conditions in the storage area 54 can include data corresponding to a dose of ultraviolet radiation delivered by an ultraviolet radiation source 12 during a predetermined time period. In this case, the computer system 20 can dynamically determine when to turn off the ultraviolet radiation source 12.

It is understood that the set of current conditions in the storage area 54 can include one or more attributes corresponding to a set of biological activity dynamics present within the storage area. The set of biological activity dynamics can include, for example, a presence of biological activity (e.g., exponential bacterial growth), a location of the biological activity, a type of biological activity (e.g., type of organism), a concentration of the biological activity, an estimated amount of time an organism has been in a growth phase (e.g., exponential growth and/or stationary), and/or the like. The set of biological activity dynamics can include information on the variation of the biological activity over time, such as a growth rate, a rate with which an area including the biological activity is spreading, and/or the like. In an embodiment, the set of biological activity dynamics are related to various attributes of bacteria activity within an area, including, for example, the presence of detectable bacteria activity, measured bacteria population/concentration time dynamics, growth phase, and/or the like.

As described herein, aspects of the invention can be implemented to treat (e.g., preserve, disinfect, and/or the like) various types of food stored in various types of environments. A typical environment can comprise a refrigerated environment, in which food is frequently stored to extend the shelf life of the food. However, embodiments can be implemented in other non-refrigerated environments, in which food is stored for a period of time, e.g., to ripen, prior to being used, and/or the like. Furthermore, an embodiment can be implemented in conjunction with a freezer, in which the temperature is maintained well below the freezing point of water. To this extent, the types of food items to which aspects of the invention can be implemented can include various types of food as described herein. As described herein, the foods can include various types of fruits and vegetables. However, the foods also can include frozen consumables, such as ice cubes, ice cream, and/or the like. Furthermore, the foods can include liquids, grains, cereals, and/or the like. Additionally, as described herein, embodiments can be implemented to treat non-food items stored in any type of environment. Such non-food items can include, for example, frozen/liquid chemicals, sand, wood, and/or the like. Regardless, it is understood that a treated item can be ultraviolet transparent (e.g., semi-transparent), ultraviolet absorbing, and/or ultraviolet reflective.

In an embodiment, the computer system 20 can be configured to operate the UV radiation source 12 (e.g., during the storage life preservation operating configuration 50A) to generate ultraviolet radiation to, for example, maintain and/or increase natural phenols, including one or more types of flavonoids, in the food items 56 within the storage area 54. In this case, the computer system 20 can increase the nutritional qualities, including antioxidant benefits, and/or increase storage life of the food items 56.

Figure 23:
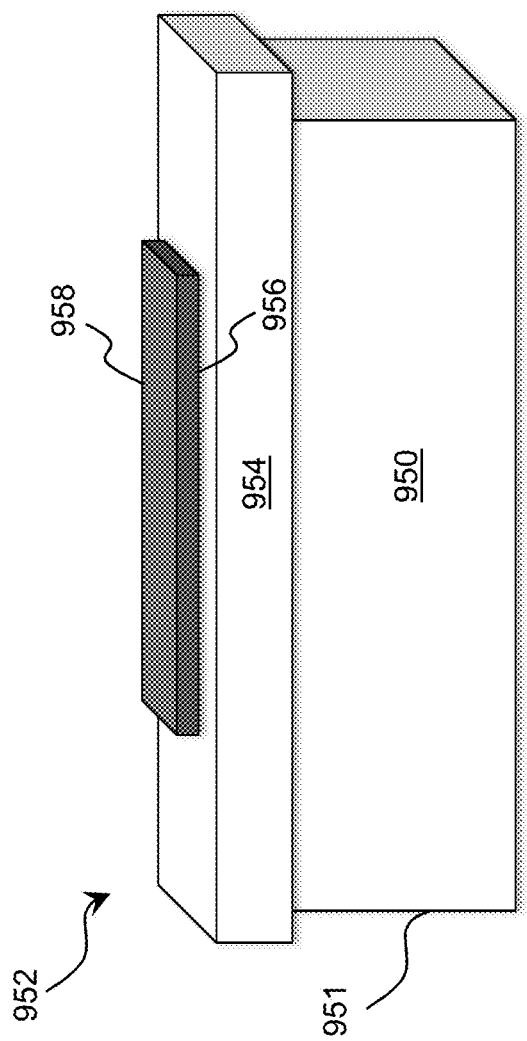
FIG. 23 shows an illustrative storage device for use with an ultraviolet radiation system according to an embodiment.

As described herein, embodiments of an ultraviolet radiation system can be implemented as part of and/or in conjunction with any type of storage device. In an embodiment, the storage device can include a transparent region for removably or permanently attaching and/or sealing an ultraviolet radiation source. For example, in FIG. 23, a storage device 952 can include a removable lid 954 with a transparent region 956 that is configured to be removably or permanently covered by an ultraviolet radiation source 958. Although the storage device 952 and lid 954 are shown as rectangular prism shapes capable of being physically separated from one another, it is understood that the storage device 952 can include any shape and access to an interior of the storage device 952 can be provided using any solution (e.g., a hinged door, a slidable cover, and/or the like). Furthermore, while the transparent region 956 is shown as being located on the lid 954, it is understood that the transparent region 956 (and therefore the ultraviolet radiation source 958) can be located on any combination of one or more surfaces forming the enclosure.

Figure 25:
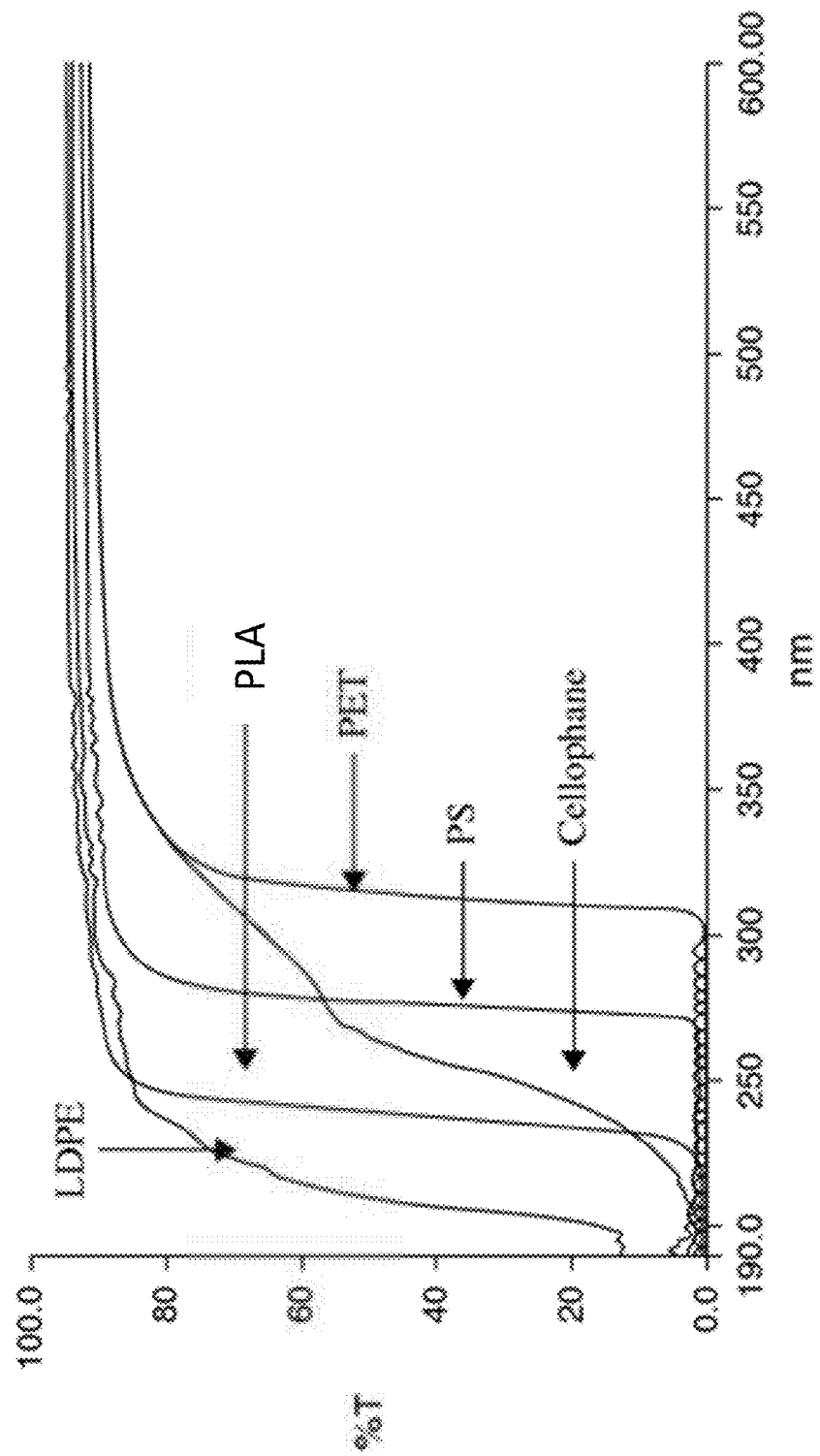
FIG. 25 shows a graph of ultraviolet transmission properties for several polymers.

The removable lid 954 can be attached and/or sealed to the container portion 950 of the storage device 952 by any means, such as a threading mechanism, a gasket, and/or the like. The transparent region 956 can be formed of any material that allows at least a portion of the ultraviolet radiation generated by the ultraviolet radiation source 958 to pass there through. In an embodiment, the transparent region 956 is formed of a polymer. FIG. 25 shows a graph of the ultraviolet transmission properties (T %) for several polymers. In an embodiment, the transparent region 956 includes a transparency of at least 50% of the ultraviolet radiation emitted by the ultraviolet radiation source 958 at a normal incidence. For example, the transparent region 956 can include a UV transparent material such as polytetrafluoroethylene (PTFE), fluorinated ethylene propylene (FEP), fluorinated ethylene-propylene (EFEP), low-density polyethylene (LDPE), polylactic acid (PLA), polystyrene (PS), a sheet of regenerated cellulose (e.g., Cellophane), and/or the like. In an embodiment, when the ultraviolet radiation source 958 is removed, the storage device 952 (e.g., the lid 954 and/or the container portion 950) can be readily cleaned using any desired solution, e.g., including a dishwasher. In this case, the materials, including the UV transparent material, can be selected to withstand repeated washing using a dishwasher (e.g., PTFE, FEP, and/or the like).

Figure 24:
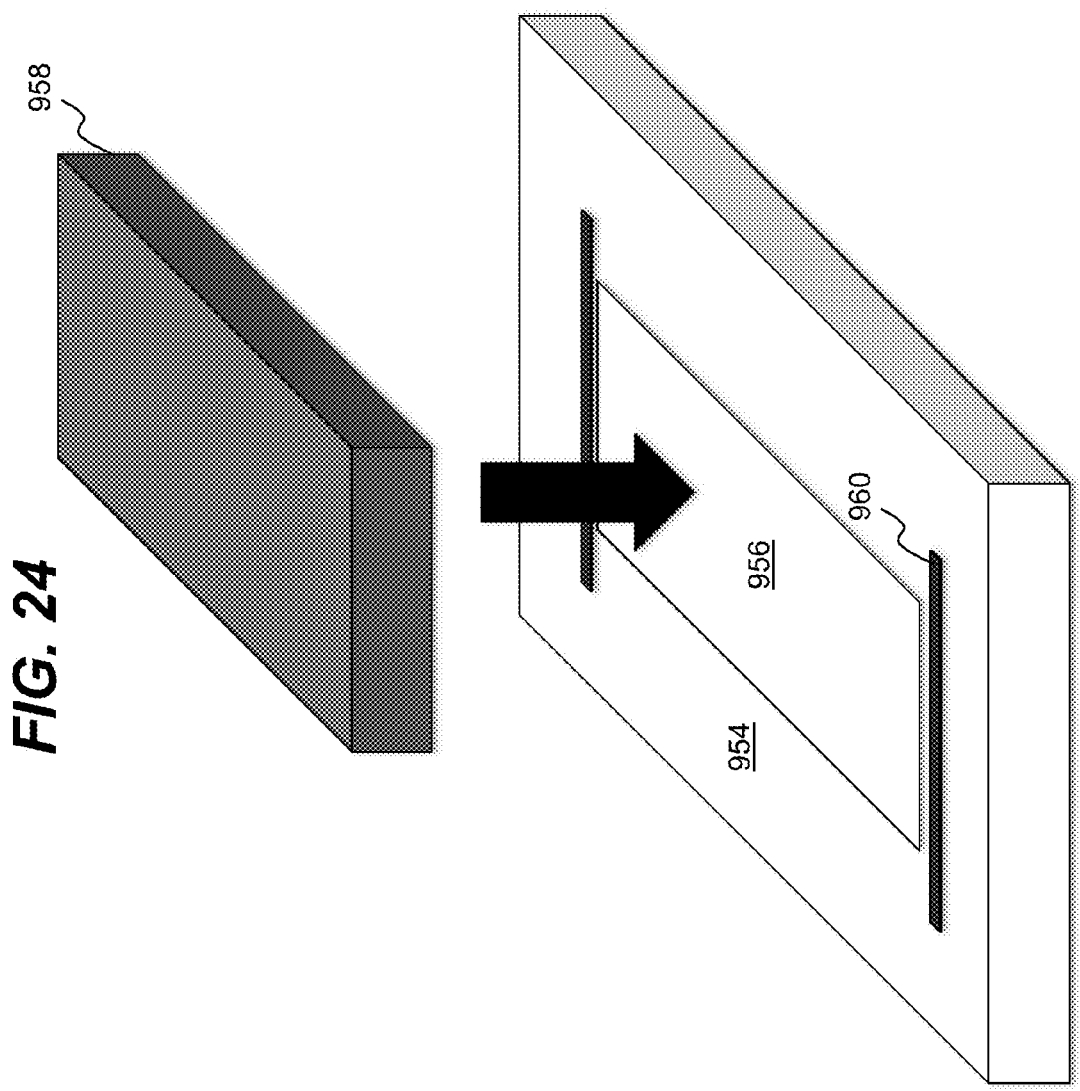
FIG. 24 shows a partial perspective view of an illustrative storage device according to an embodiment.

As illustrated in FIG. 24, the ultraviolet radiation source 958 can be permanently or removably attached to the removable lid 954 using any solution. For example, the lid 954 can include a set of fixtures 960, which are configured to hold the ultraviolet radiation source 958 in a proper position and/or secure the ultraviolet radiation source 958 to the lid 954. Illustrative fixtures 960 include, for example, a sliding rail designed for the ultraviolet radiation source 958 to slide into. In another embodiment, the fixtures 960 can include plastic clips for snapping the ultraviolet radiation source 958 into place. The plastic clips can be integrated into the ultraviolet radiation source 958 and snapped into an opening on the lid 954. In another embodiment, the fixtures 960 can include a hook and loop fastener (e.g., Velcro) to attach the ultraviolet radiation source 958 to the lid 954. When attached, the connection between the ultraviolet radiation source 958 and the removable lid 954 can provide an airtight connection and the ultraviolet radiation source 958 can cover the transparent region 956 so that ultraviolet radiation does not exit the storage device 952 via the transparent region 956 and/or exit from a gap between the ultraviolet radiation source 958 and the lid 954. In an embodiment, a feedback component, such as the feedback component 14 in FIG. 3, can be used to monitor the current set of conditions within the storage area, i.e., container portion 950 of the storage device 952. For example, the feedback component 14 can determine whether ultraviolet radiation can exit the storage device 952. In this case, the feedback component 14 can determine whether the removable lid 954 is securely attached to the container portion 950 of the storage device 952 and/or the ultraviolet radiation source 958 completely covers the transparent region 956. While the transparent region 956 has been shown and described in conjunction with use of an ultraviolet radiation source 958, it is understood that a transparent region 956 can be utilized in conjunction with a visible and/or infrared source 15 (FIG. 3) and/or sensing device(s) 16 (FIG. 3). Similarly, a single structure configured to cover a transparent region 956 can include any combination of one or more of: the ultraviolet radiation source 958, the visible and/or infrared source 15, sensing device(s) 16, and/or the like.

Returning to FIG. 23, an interior surface of the walls 951 of the remaining portion of the storage device 952 can be at least 50% reflective to ultraviolet radiation of a relevant wavelength at a normal incidence. Similarly, an interior surface of a remaining portion of the removable lid 954 (e.g., not including the transparent region 956) can also be at least 50% reflective to ultraviolet radiation of a relevant wavelength at a normal incidence. In an embodiment, at least a portion of an interior surface of the walls 951 of the storage device 952 can include a sterilizing agent or a photo-activated sterilizing agent, such as $TiO_2$ and MgO particles, as well as silver or copper nanoparticles, and/or the like, to increase an effectiveness of sterilization of an object located within the storage device 952. In another embodiment, at least a portion of the walls 951 of the storage device 952 can include a fluorescent agent for the purpose of indicating that the ultraviolet radiation is turned on. In an embodiment, the fluorescent agent can include fluorescent pigments and dyes, such as LUMW fluorescent pigment, and/or the like.

Turning to FIGS. 26A and 26B, a structure 1052 used to enclose an interior of a storage device described herein can be configured to emit diffuse ultraviolet radiation into the interior. For example, as described in U.S. application Ser. No. 14/478,266, the structure 1052 can include a plurality of transparent regions 1056 incorporated into one or more structures 1052 enclosing an interior of the storage device, e.g., including on a removable lid, a side wall, a bottom, and/or the like, to allow for ultraviolet radiation to be directed into the interior of the storage device. For example, the structure 1052 can form the transparent region 956 (FIG. 23), be incorporated as part of the ultraviolet radiation source 958 (FIG. 23), and/or the like. Regardless, each of the transparent regions 1056 can be covered by at least one ultraviolet radiation source, e.g., each transparent region 1056 is shown covered by a plurality of ultraviolet radiation sources 1058A-C. The transparent regions 1056 can be completely covered as described herein so that no ultraviolet radiation escapes from the interior of the corresponding storage device through the transparent regions 1056 or through a gap between the ultraviolet radiation sources 1058A-C and the corresponding transparent region 1056.

The structure 1052 also can include a set of reflecting mirrors 1060, each of which is located directly beneath a transparent region 1056. The reflecting mirrors 1060 can comprise a highly diffusive ultraviolet radiation material, such as a highly ultraviolet reflective expanded polytetrafluoroethylene (ePTFE) membrane (e.g., GORE® Diffuse Reflector Product (DRP)), and/or the like. In an embodiment, the reflecting mirrors 1060 can comprise a fluoropolymer, such as fluorinated ethylene-propylene (EFEP), fluorinated ethylene propylene (FEP), perfluoroalkoxy (PFA), tetrafluoroethylene hexafluoropropylene vinylidene fluoride (THV), polytetrafluoroethylene (PTFE), polyvinylidene fluoride (PVDF), ethylene-tetrafluoroethylene (ETFE), Teflon, and/or the like. In still another embodiment, the reflecting mirrors 1060 can be partially UV reflecting, partially UV transparent. For example, the reflecting mirrors 1060 can comprise an UV reflective film over an UV transparent film. In an embodiment, the reflecting mirrors 1060 can be configured to provide specular reflection and can comprise, for example, polished aluminum, and/or the like.

The reflecting mirrors 1060 can diffuse the ultraviolet radiation emitted by the ultraviolet radiation sources 1058A-1058C throughout an interior the structure 1052 prior to the ultraviolet radiation exiting out an exit surface 1062. The exit surface 1062 of the structure 1052 can include a diffusive film to further increase a uniformity of the ultraviolet radiation, which can be emitted out the exit surface 1062 into an interior of the storage device. In an embodiment, the exit surface 1062 is at least 40% transparent and at most, 30% absorbent to ultraviolet radiation of a relevant wavelength at a normal incidence. In an embodiment, the exit surface 1062 can also include an opening for ultraviolet radiation to exit the structure 1052.

Figure 28:
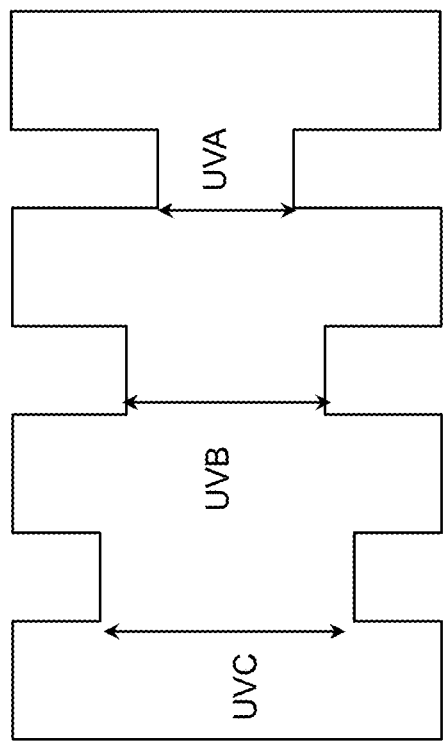
FIG. 28 shows a band diagram for an illustrative heterostructure including barriers and quantum wells according to an embodiment.

Each of the ultraviolet radiation sources 1058A-C can be selected/engineered to produce an emission with a particular peak radiation wavelength. For example, a first ultraviolet radiation source 1058A can produce an emission with a peak wavelength within the UV-A spectrum, a second ultraviolet radiation source 1058B can produce an emission with a peak wavelength within the UV-B spectrum, and a third ultraviolet radiation source 1058C can produce an emission with a peak wavelength within the UV-C spectrum. In another embodiment, a single ultraviolet radiation source can be configured to concurrently emit multi-peak ultraviolet radiation. For example, FIG. 28 shows a schematic of an illustrative band diagram incorporating barriers and quantum wells of different depth resulting in emission of several wavelengths.

Figure 27:
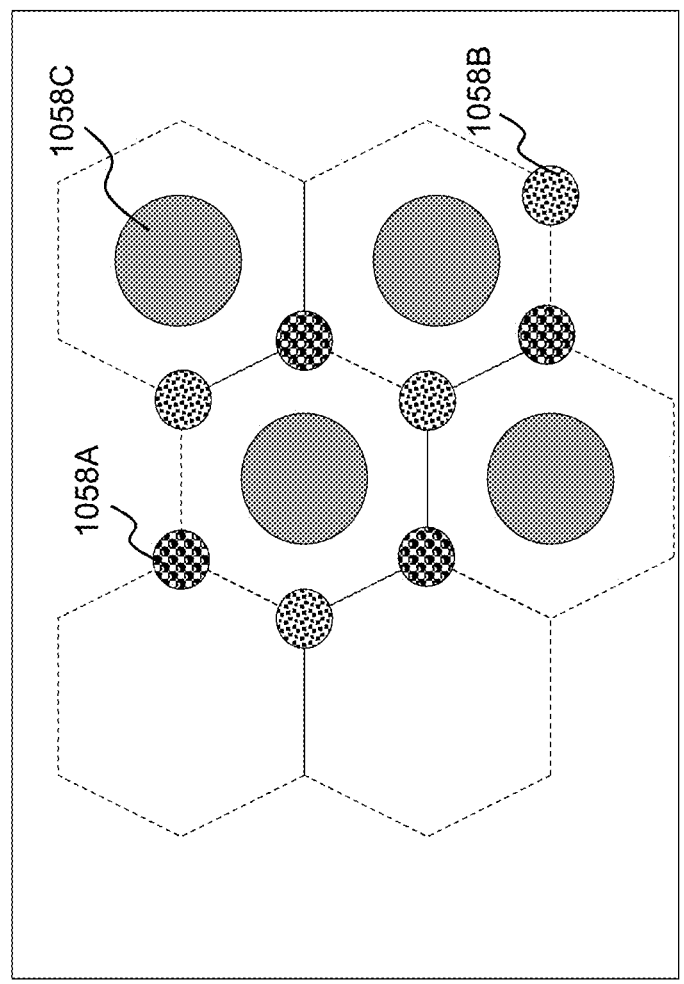
FIG. 27 shows an illustrative arrangement of ultraviolet radiation sources according to an embodiment.

When multiple ultraviolet radiation sources 1058A-C are utilized, the plurality of ultraviolet radiation sources 1058A-C can be arranged in any formation. For example, FIG. 26A shows the ultraviolet radiation sources 1058A-C arranged in a staggered formation. Alternatively, FIG. 27 illustrates the ultraviolet radiation sources 1058A-C arranged in a honeycomb formation. In this case, a larger third ultraviolet radiation source 1058C can be surrounded by the first ultraviolet radiation sources 1058A and the second ultraviolet radiation sources 1058B arranged in an alternating pattern in the honeycomb formation. However, it is understood that these arrangements are only illustrative of various possible arrangements that can be utilized in embodiments described herein. While the structure 1052 has been shown and described in conjunction with use of ultraviolet radiation sources 1058A-C, it is understood that a structure 1052 can be utilized in conjunction with a visible and/or infrared source 15 (FIG. 3). Similarly, a single structure 1052 can include any combination of one or more of: the ultraviolet radiation source 958, the visible and/or infrared source 15, and/or the like.

Figure 29:
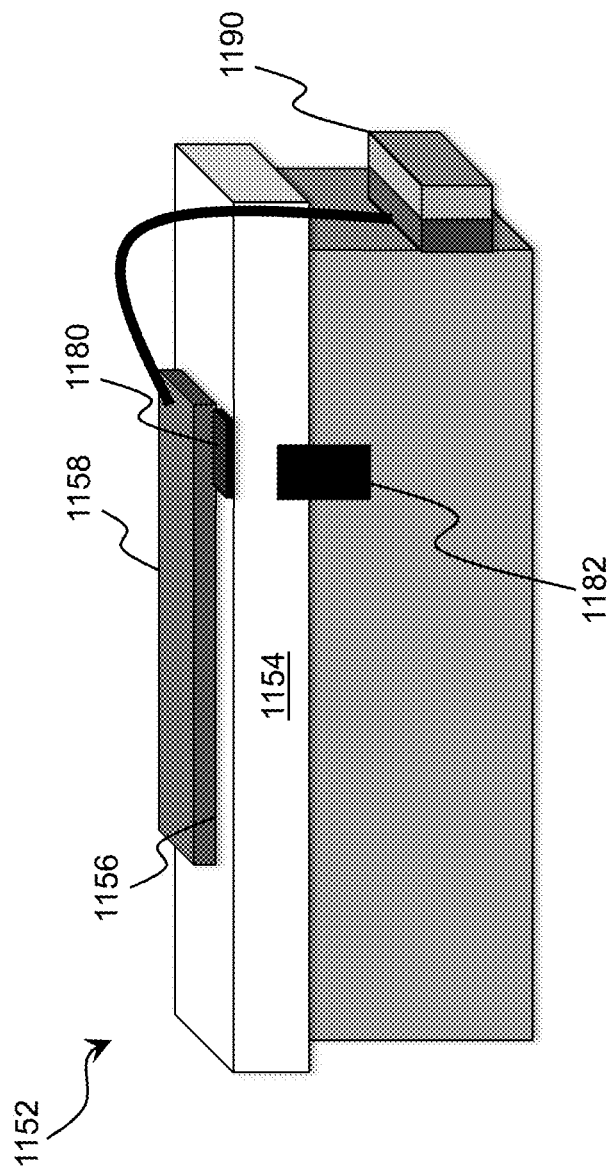
FIG. 29 shows a perspective view of an illustrative storage device according to an embodiment.

In an embodiment, a storage device described herein can include sensors for acquiring data indicating whether the storage device is in a configuration in which it is safe to turn on the ultraviolet radiation source. For example, in FIG. 29, a storage device 1152 is shown including a first sensor 1180 for indicating that the ultraviolet radiation source 1158 is securely attached to the removable lid 1154. When securely attached, the ultraviolet radiation source 1158 can be configured to completely cover the transparent region 1156 on the removable lid 1154. The storage device 1152 can also include a second sensor 1182 for indicating that the removable lid 1154 is securely attached to the remaining portion of the storage device 1152 so that an interior of the storage device is completely enclosed. A monitoring and/or control system 1190 can receive and process data acquired by the sensors 1180, 1182 to control the ultraviolet radiation source 1158 using any solution (e.g., allow the radiation source 1158 to be turned on, force a turn off, and/or the like). The monitoring and/or control system 1190 can be wired or wirelessly connected to the ultraviolet radiation source 1158, sensors 1180, 1182, and/or other portions of the storage device 1152.

Figure 30:
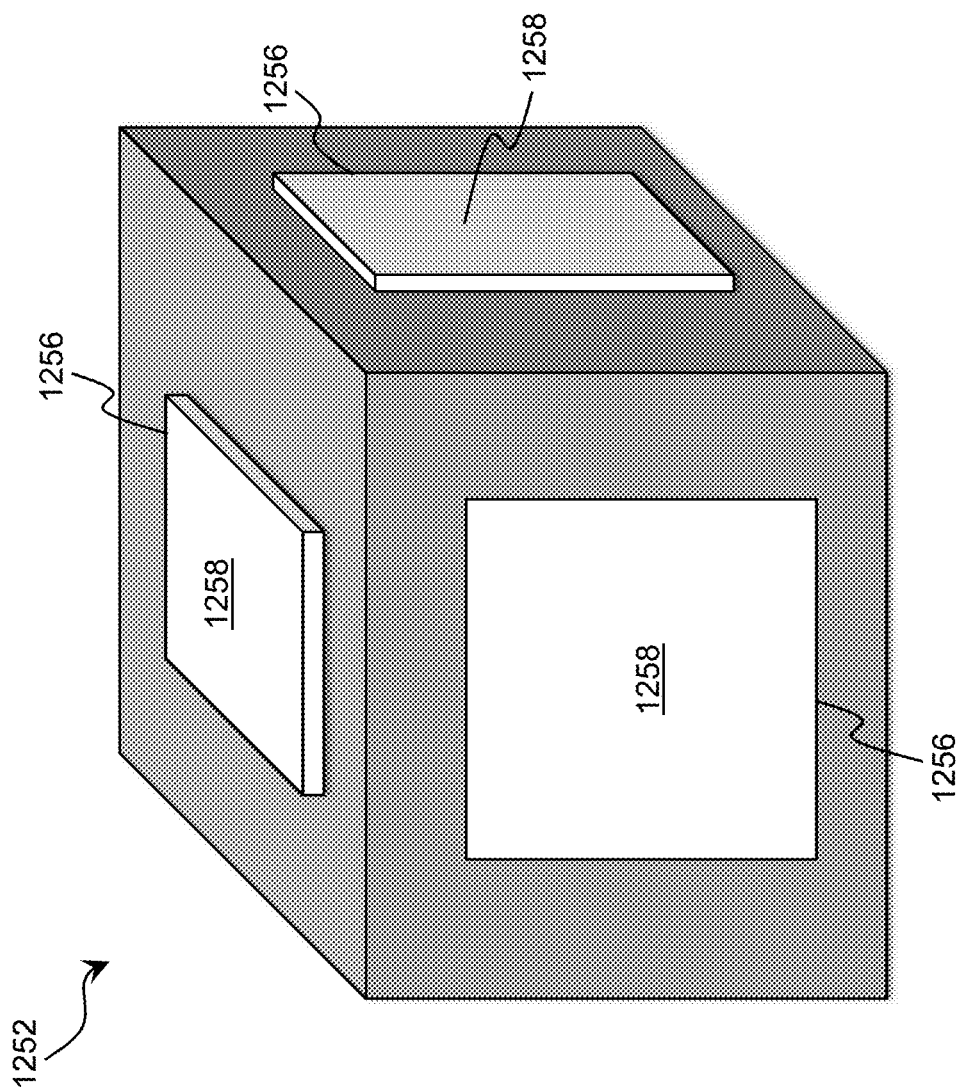
FIG. 30 shows a perspective view of an illustrative storage device according to an embodiment.

Additionally, it is understood that an ultraviolet radiation source 1158 can be implemented in multiple physical structures, each of which includes one or more ultraviolet radiation devices, and can be independently and/or collectively controlled by the monitoring and/or control system 1190. For example, as illustrated in FIG. 30, a storage device 1252 can include more than one transparent region 1256 and corresponding ultraviolet radiation source 1258. Although not shown, it is understood that the storage device 1252 can include a sensor for each ultraviolet radiation source 1258, e.g., to acquire data indicative of whether the ultraviolet radiation source 1258 is properly secured to the storage device 1252. In response to an indication that at least one of the ultraviolet radiation sources 1258 is not securely attached to the storage device 1252, the monitoring and/or control system 1190 (FIG. 29) can inactivate all of the remaining ultraviolet radiation sources 1258.

Figure 31:
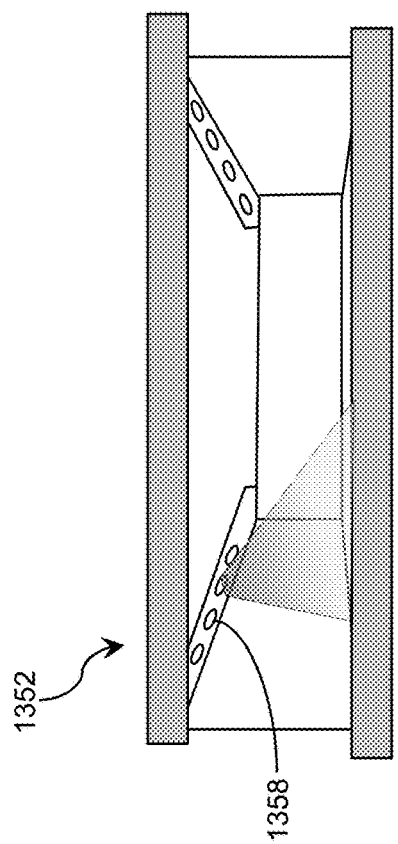
FIG. 31 shows a refrigerator drawer including an illustrative ultraviolet radiation system according to an embodiment.

As mentioned above in FIG. 4A, an illustrative storage device for use with an ultraviolet radiation system can include a refrigerator and/or freezer. For example, an ultraviolet radiation system discussed herein can be used in a storage drawer of a refrigerator. Turning now to FIG. 31, an illustrative drawer 1352 can include a set of ultraviolet radiation sources 1358 of an ultraviolet radiation system. Although the set of ultraviolet radiation sources 1358 are shown located on an upper left side of the drawer 1352, it is understood that the set of radiation sources 1358 can be located anywhere within the drawer 1352. The set of ultraviolet radiation sources 1358 are located in a position within the drawer 1352, so that during normal use of the refrigerator (FIG. 4A) and/or the drawer 1352, the set of ultraviolet radiation sources 1358 do not obscure the use of the drawer 1352. Furthermore, the set of ultraviolet radiation sources 1358 are located in a position within the drawer 1352 so that the set of ultraviolet radiation sources 1358 are not easily visible during normal use of the drawer 1352 and/or the refrigerator.

Figure 32B:
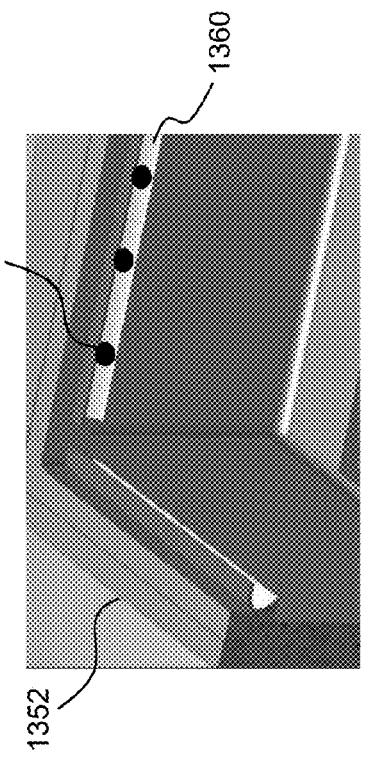
FIGS. 32A and 32B show perspective views of a refrigerator drawer including a reflector according to an embodiment.
Figure 32A:
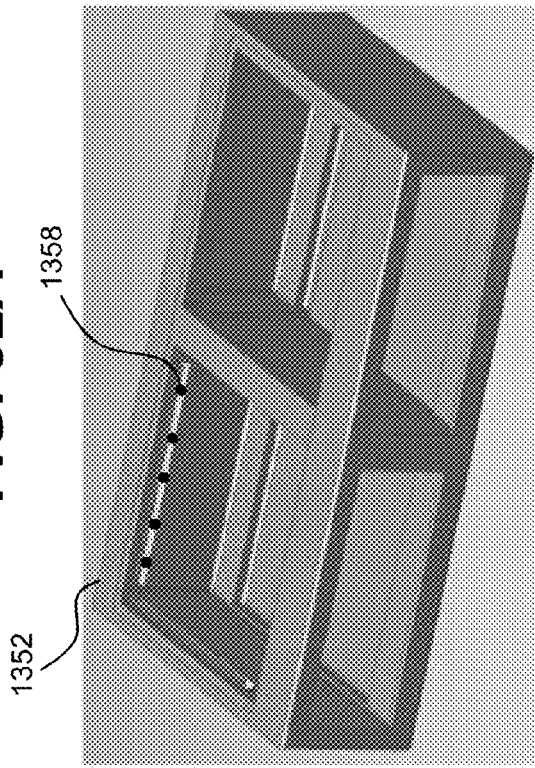
Figure 33:
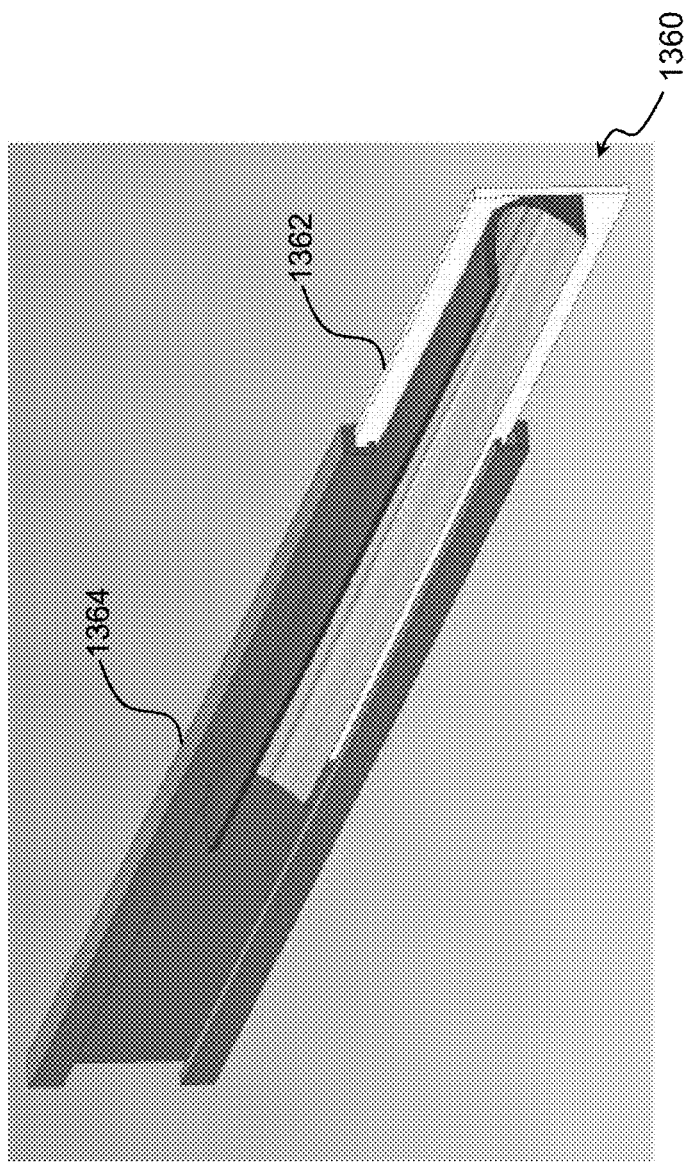
FIG. 33 shows a partial perspective view of an illustrative rail system for connecting a reflector according to an embodiment.

The ultraviolet radiation sources 1358 can be permanently or removably mounted within the drawer 1352 using any solution. For example, turning now to FIGS. 32A and 32B, the ultraviolet radiation sources 1358 can be mounted on a reflector 1360, which is attached to an interior surface of the drawer 1352. The reflector 1360 can made of any material that reflects ultraviolet radiation, such as polished aluminum, a highly ultraviolet reflective ePTFE membrane (e.g., GORE® Diffuse Reflector Material), and/or the like. The ultraviolet radiation sources 1358 can be mounted within a curved portion of the reflector 1360 in order to increase an amount of ultraviolet radiation that is reflected into the drawer 1352. The reflector 1360 can be permanently or removably attached to the interior surface of the drawer 1352 using any solution. For example, as shown in FIG. 33, the reflector 1360 can include a segment 1362 that slides into a rail system 1364, which is attached to and/or forms a part of the interior surface of the drawer 1352.

Figure 34:
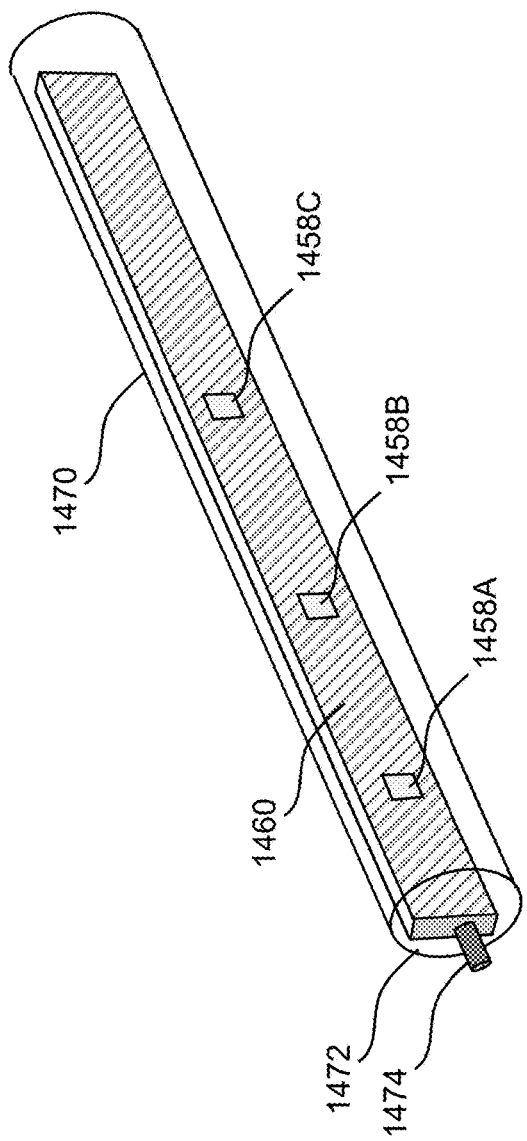
FIG. 34 shows a perspective view of an illustrative arrangement of ultraviolet radiation sources within a transparent enclosure according to an embodiment.

Turning now to FIG. 34, in another embodiment, a reflector 1460 including a set of ultraviolet radiation sources 1458A-C can be contained within an enclosure 1470 that is partially transparent to ultraviolet radiation. In this embodiment, the enclosure 1470 can completely surround the reflector 1460. The set of ultraviolet radiation sources 1458A-C within the reflector 1460 can be spaced at distances that are smaller than the diameter of an irradiation spot on the enclosure 1470 opposite each ultraviolet radiation source 1458A-C. The enclosure 1470 can comprise a fluoropolymer, such as EFEP, FEP, PFA, THV, and/or the like. The sides of the enclosure 1470 can be covered by caps 1472, which include an electrical connection 1474 for powering the set of ultraviolet radiation sources 1458A-C. The enclosure 1470 including the reflector 1460 with the set of ultraviolet radiation sources 1458A-C, can be mounted within a drawer, such as the drawer 1352 shown in FIGS. 32A and 32B, using any solution. For example, although not shown, the enclosure 1470 can be mounted within a drawer using a rail system, such as the rail system 1364 shown in FIG. 33.

Turning now to FIGS. 35A and 35B, light diffusions of illustrative systems 1452A, 1452B are shown. In this case, the system 1452A includes a set of ultraviolet radiation sources without an enclosure 1470 (FIG. 34) and the system 1452B includes a set of ultraviolet radiation sources with the enclosure 1470, e.g., an FEP tube. While each system 1452A, 1452B is shown including four ultraviolet radiation devices (each corresponding to a bright spot), it is understood that this is only illustrative. In the system 1452B, the power of the ultraviolet radiation diffused through the enclosure 1470 is approximately 5% less than the power of the ultraviolet radiation diffused within the system 1452A due to some of the ultraviolet radiation being absorbed by the enclosure. However, the ultraviolet radiation in the system 1452B is diffused more uniformly throughout the area than is the ultraviolet radiation in the system 1452A.

Figure 36B:
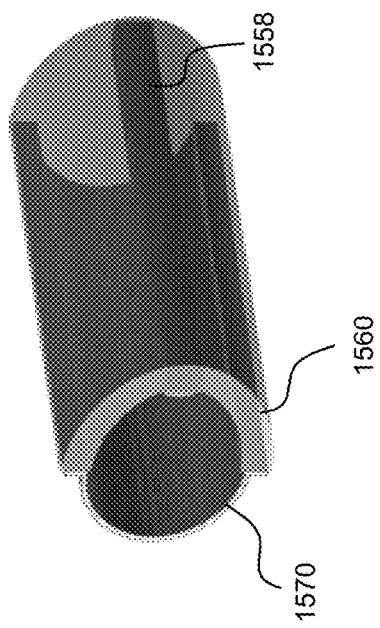
FIGS. 36A and 36B show a cross-sectional and a perspective three-dimensional view, respectively, of an illustrative ultraviolet radiation system according to an embodiment.
Figure 36A:
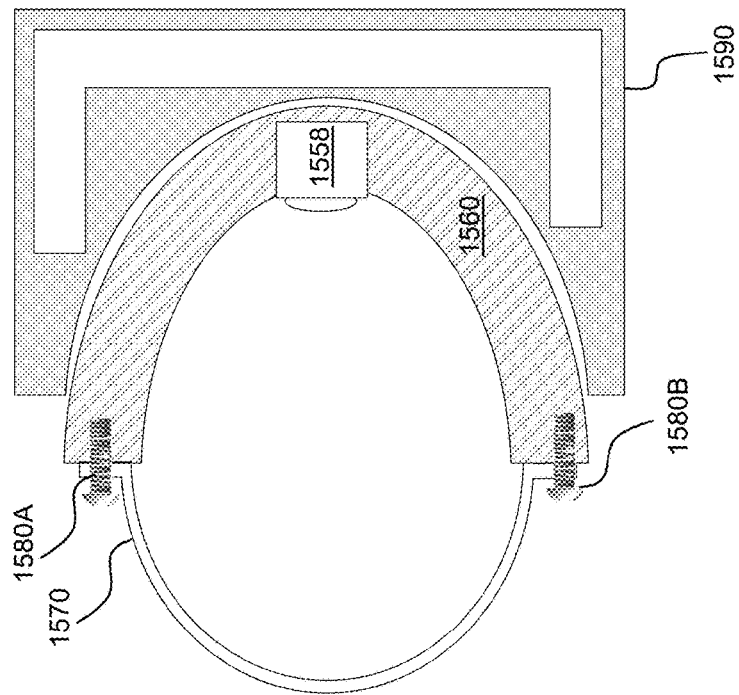

Turning now to FIGS. 36A and 36B, in an embodiment, a reflector 1560 including a set of ultraviolet radiation sources 1558 mounted on the reflector 1560 is shown. FIG. 36A shows a cross-sectional view, while FIG. 36B shows a perspective three-dimensional view. In this embodiment, an enclosure 1570 covers the open portion of the reflector 1560 to form a round shape, such as a circle, an ellipse, an oval, and/or the like. Similar to the enclosure 1470 shown in FIG. 34, the enclosure 1570 is partially transparent to ultraviolet radiation and can comprise a fluoropolymer, such as EFEP, FEP, PFA, THV, and/or the like. The enclosure 1570 can be attached to the reflector 1560 using any solution. For example, as shown in FIG. 36A, a set of bolts 1580A, 1580B can be used to attach the enclosure 1570 to the reflector 1560. In another embodiment, the enclosure 1570 can be attached to the reflector 1560 by other means, such as latches, clips, grooves, and/or the like. In an embodiment, the enclosure 1570 is attached to the reflector 1560 using a solution that enables easily disassembly. For example, the enclosure 1570 can be easily detached from the reflector 1560 so that parts can be replaced. For example, the enclosure 1570 can be easily detached from the reflector 1560 so that the enclosure 1570 can be replaced, one or more of the set of ultraviolet radiation sources 1558 can easily be replaced, the reflector 1560 can be easily replaced, and/or the like. The reflector 1560 can be mounted on a second enclosure 1590, which houses the electrical components for powering the set of ultraviolet radiation sources 1558 and enables the structure to be permanently or removably attached to a surface (e.g., an interior wall of a storage device) using any solution.

Figure 37:
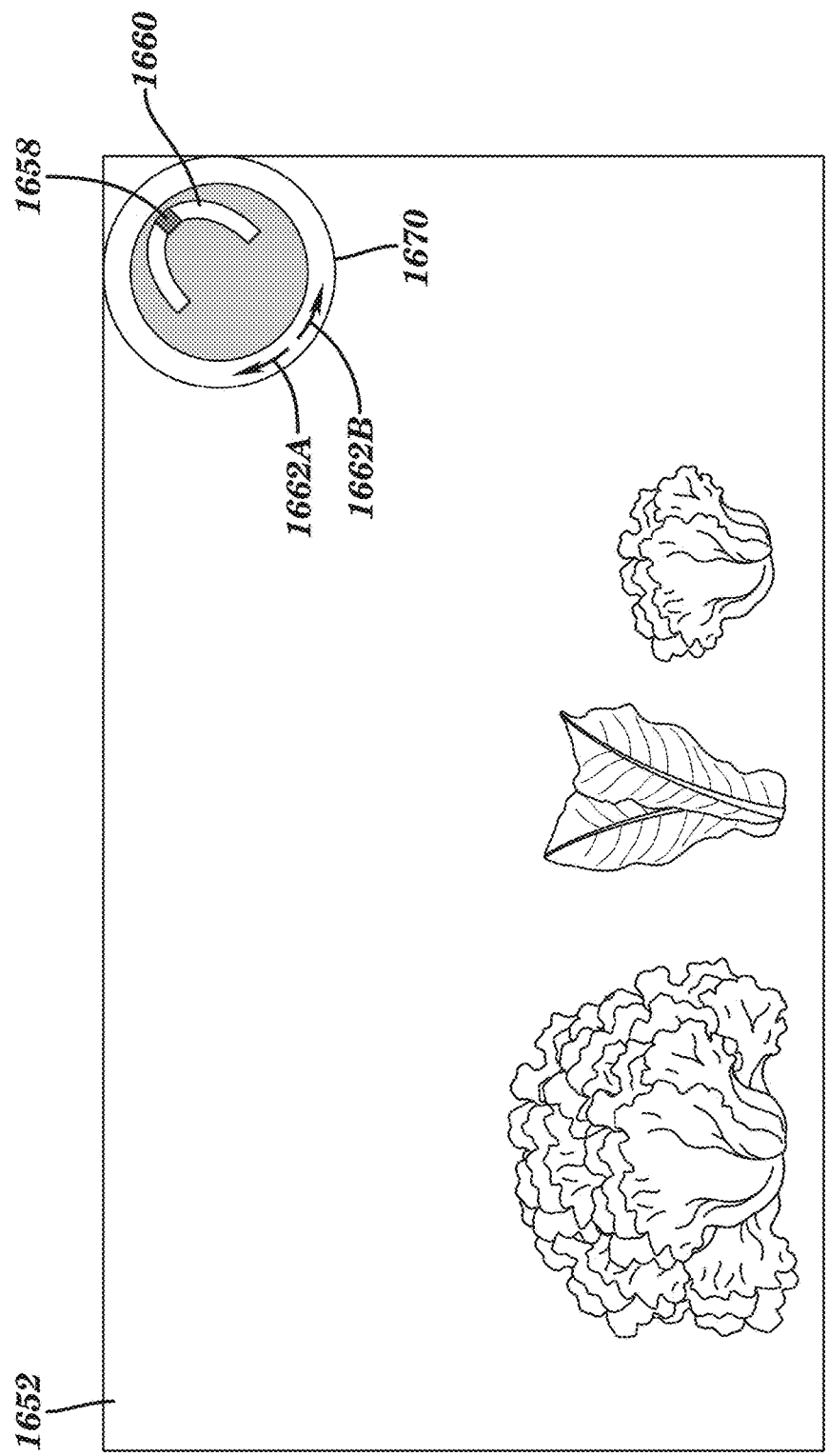
FIG. 37 shows an illustrative storage device for use with an ultraviolet radiation system according to an embodiment.

Turning now to FIG. 37, in an embodiment, an enclosure 1670 including a reflector 1660 with a set of ultraviolet radiation sources 1658 can be mounted in a corner of a drawer 1652. The enclosure 1670 and/or the reflector 1660 can be configured to be rotated (e.g., by the monitoring and/or control system 11 shown in FIG. 1) according to arrows 1662A, 1662B in order to redirect the ultraviolet radiation into a target area within the drawer 1652. In an embodiment, the monitoring and/or control system 11 selects the target area and rotates the enclosure 1670 and reflector 1660 accordingly based on conditions within the drawer 1652 (e.g., using data acquired by the feedback component 14 (FIG. 3), based on a current operating configuration, and/or the like. The degree of rotation for the enclosure 1670 and/or the reflector 1660 is not limited to the directions shown by the arrows 1662A, B. Rather, the enclosure 1670 and/or the reflector 1660 can rotate at any angle and in any direction within the drawer 1652 in order to direct ultraviolet radiation at any area within the drawer 1652.

The enclosure 1670 can be diffusively partially transparent to ultraviolet radiation, similar to the enclosures shown in FIGS. 32A, 32B, 34, 36A and 36B. However, if diffusive properties are not desired, then the partially transparent enclosure 1670 can include no diffusive properties and can comprise fused silica, sapphire, and/or the like. Regardless, the enclosure 1670 can transmit a majority portion of the ultraviolet radiation and can be at least approximately 50% transparent to ultraviolet radiation. In any of the embodiments for the enclosure discussed herein, the enclosure can include a patterning, roughening, lenses, and/or the like. The reflector 1660 can be highly reflective to ultraviolet radiation and reflect at least approximately 50% of the ultraviolet radiation. In all embodiments discussed herein, the reflector can be specularly reflective or diffusively reflective.

Figure 38:
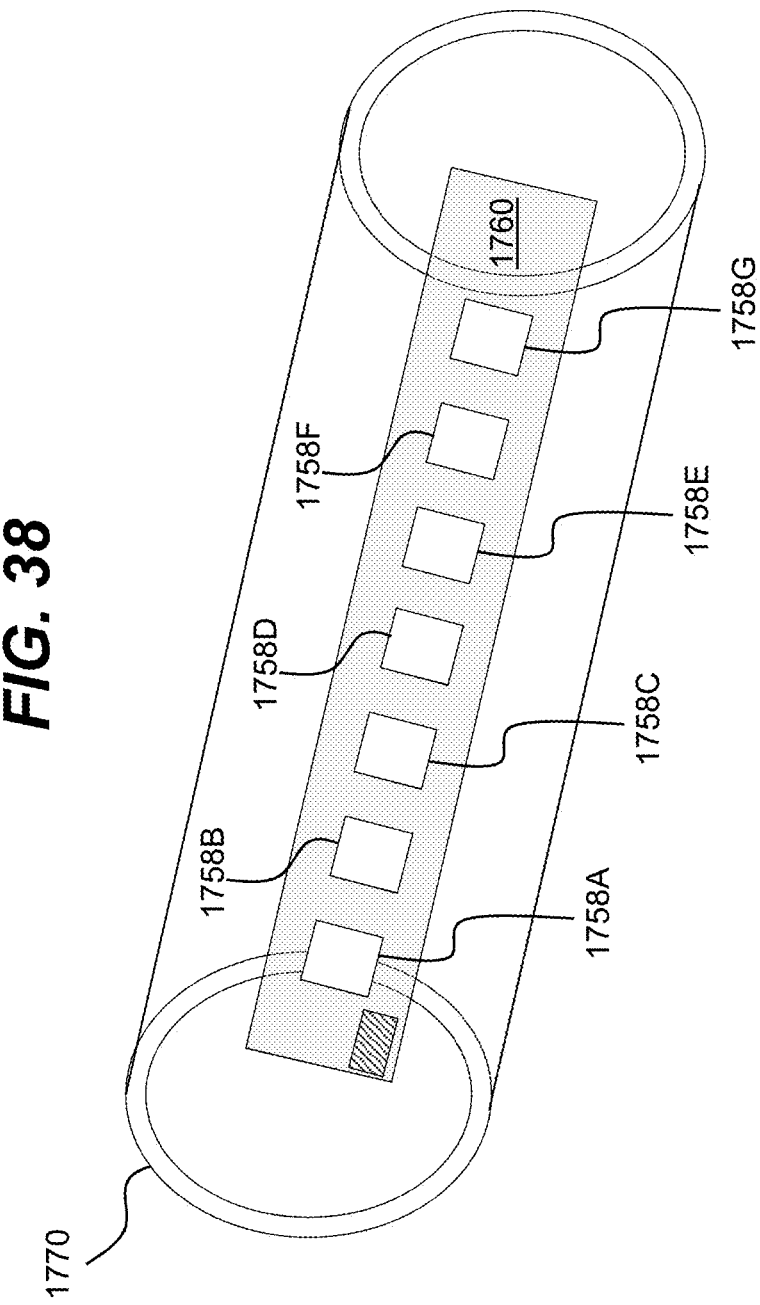
FIG. 38 shows an illustrative ultraviolet radiation system according to an embodiment.

Turning now to FIG. 38, in an embodiment, the reflector 1760 can include different radiation sources operating at difference wavelengths. For example, radiation sources 1758B, 1758E, and 1758G can include ultraviolet radiation sources, which operate in the ultraviolet radiation wavelength range. Radiation sources 1758A, 1758C, 1758D, and 1758F can include visible and/or infrared radiation sources, which operate in the visible and/or infrared wavelength ranges. The monitoring and/or control system 11 (FIG. 1) can be configured to turn on ultraviolet radiation sources 1758B, 1758E, and 1758G only when the drawer, such as drawer 1352 in FIG. 32A, is closed, whereas the visible and/or infrared radiation sources 1758A, 1758C, 1758D, and 1758F can be turned on when a door to a refrigerator, such as the refrigerator shown in FIG. 4A, is opened. In an embodiment, the ultraviolet radiation sources 1758B, 1758E, and 1758G and/or the visible and/or infrared radiation sources 1758A, 1758C, 1758D, and 1758F can be configured to generate radiation at a different wavelengths.

Figure 39A:
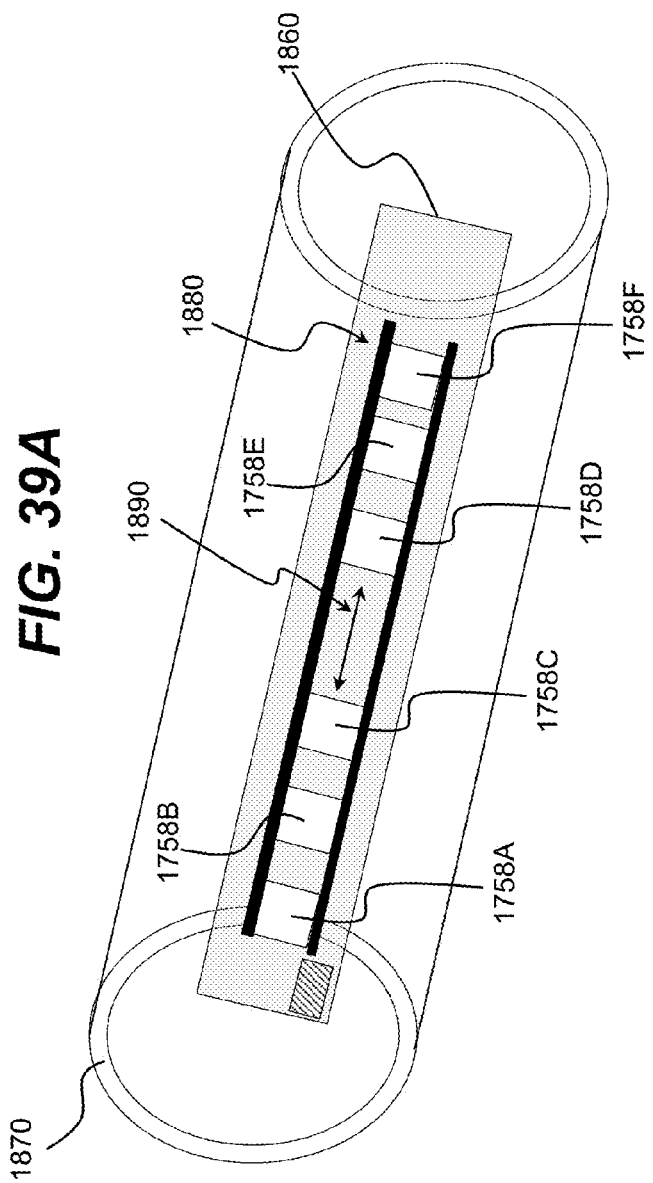
Figure 39B:
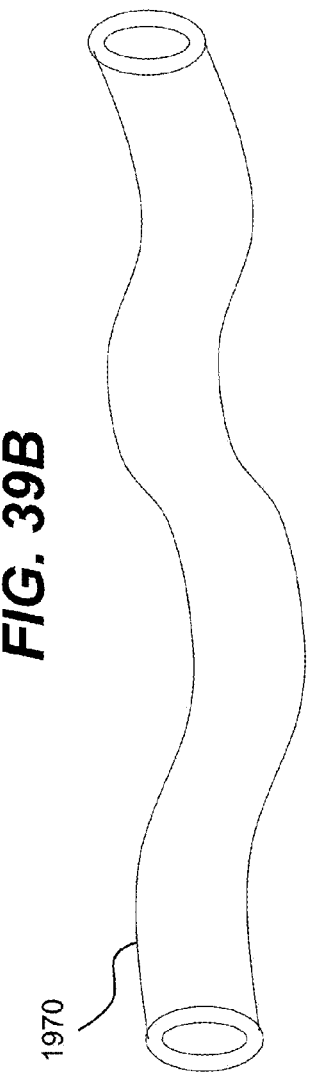
FIG. 39B shows an illustrative ultraviolet radiation system including a flexible transparent enclosure according to an embodiment.

Turning now to FIG. 39A, in an embodiment, the radiation sources 1758A-F can be movable within the enclosure 1870. For example, the enclosure 1870 can include a rail system 1880 for a set of radiation sources 1758A-F. The rail system 1880 can be mounted on a reflector 1860. The set of radiation sources 1758A-F can be configured to be moved along the rail system 1880 by the monitoring and/or control system 11 (FIG. 1) in either direction, according to an arrow 1890. Turning now to FIG. 39B, in an embodiment, the enclosure 1970 can include flexible material. In an embodiment, the flexible material for the enclosure 1970 can include a fluoropolymer. The flexibility of the enclosure 1970 can be used for easy placement of the enclosure 1970.

Figure 40:
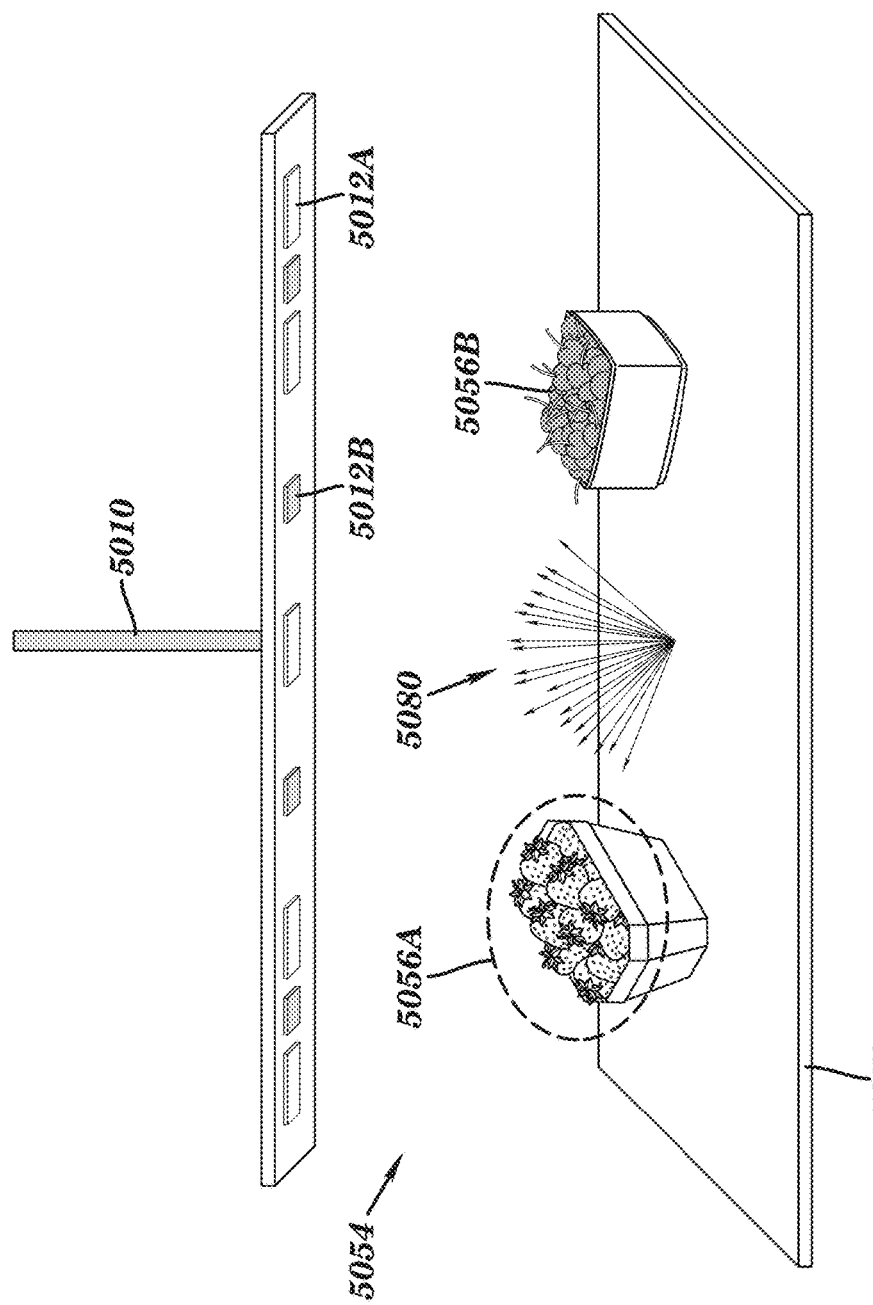
FIG. 40 shows an illustrative storage area for use with an ultraviolet radiation system according to an embodiment.

Turning now to FIG. 40, in an embodiment, a storage area 5054 can include a suspended lamp 5010 positioned over a shelf 5072 with a set of items 5056A, 5056B. The suspended lamp 5010 includes several sets of ultraviolet radiation sources 5012A, 5012B. Although only two sets are shown, it is understood that the suspended lamp 5010 can include any numbers of ultraviolet radiation sources. Further, it is understood that the suspended lamp 5010 can include other radiation sources, such as visible light sources, infrared light sources, and/or the like. Each set of ultraviolet radiation sources 5012A, 5012B can operate in a target wavelength range for a desired result. For example, the first set of ultraviolet radiation sources 5012A can operate in a range of approximately 285 nm to approximately 315 nm in order to prolong the storage life of the set of items 5056A, 5056B. This radiation can have a uniform emission over the storage area 5054 occupied by the set of items 5056A, 5056B, with an intensity variation of no more than 50%. The second set of ultraviolet radiation sources 5012B can operate in a range of approximately 260 nm to approximately 285 nm in order to suppress the growth of mildew and bacteria within the storage area 5054. For all the sets of ultraviolet radiation sources 5012A, 5012B, it is understood that the UV dose, the intensity, the spectral power, the visible illumination, the direction, and/or the like for the radiation can be changed, depending on the set of items 5056A, 5056B, which can be determined by a sensing device 16 (e.g., a visual camera) (FIG. 3).

In any of the embodiments discussed herein, the surface of a shelf can be covered by a photo-catalyst, such as $TiO_2$, which can be activated by ultraviolet radiation. For example, at least a portion of the shelf 5072 in FIG. 40 can include a photo-catalyst. The photo-catalyst can improve disinfection within the ambient of the storage area 5054 and can help to eliminate the undesirable smells present in the ambient of the storage area 5054. The ultraviolet radiation used for activating the photo-catalyst can include UV-A, UV-B, and UV-C. However, UV-C is more likely to be absorbed in the thin photo-catalyst (e.g., $TiO_2$) layers. In an embodiment, the UV radiation interacting with the photo-catalyst $TiO_2$ can have a wavelength lower than an absorption edge of the $TiO_2$ photo-catalyst. For example, the absorption edge of the $TiO_2$ photo-catalyst can be approximately 380 nm.

In an embodiment, the suspended lamp 5010 can include at least three sets of ultraviolet radiation sources 5012A, 5012B, and each of the sets of ultraviolet radiation sources 5012A, 5012B can radiate at UV-A wavelengths, UV-B wavelengths, and UV-C wavelengths. In an embodiment, the ultraviolet radiation can be used to eliminate the presence of ethylene in the ambient of the storage area 5054. In an embodiment, a portion of the surface of the shelf 5072 can include a diffusive material that allows for diffusive scattering 5080 of the ultraviolet radiation within the storage area 5054 in order to improve ultraviolet radiation recycling and coverage. In an embodiment, the shelf 5072 can include ultraviolet radiation transparent regions with a set of ultraviolet radiation sources embedded within the shelf 5072 in order to direct ultraviolet radiation from the bottom of the set of items 5056A, 5056B.

Figure 41:
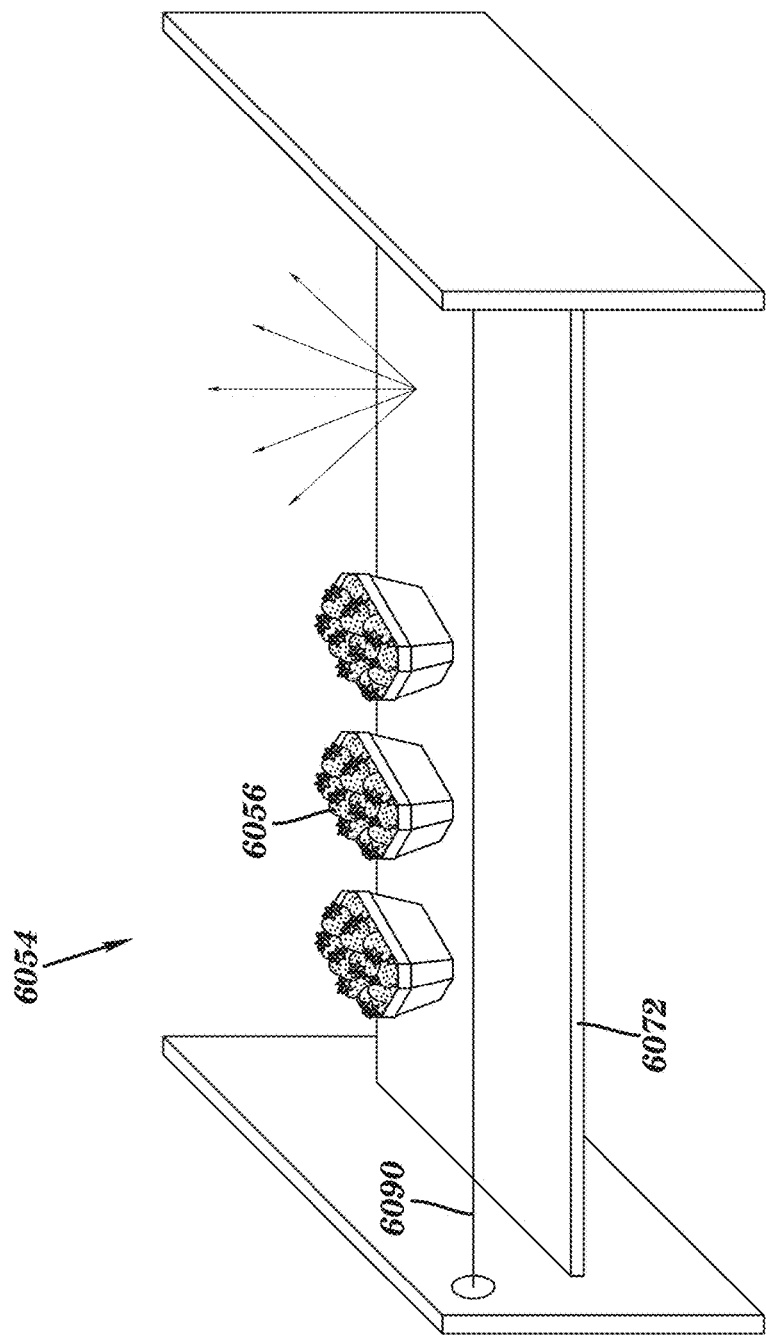
FIG. 41 shows an illustrative storage area for use with an ultraviolet radiation system according to an embodiment.

Turning now to FIG. 41, a storage area 6054 according to an embodiment is shown. In this embodiment, the storage area 6054 can include a sensing device 16 (FIG. 3) that is used to determine whether a person is in proximity of the shelf 6072. In response to a person in proximity to the shelf 6072 from the sensing device 16, the computer system 20 (FIG. 3) can turn off the ultraviolet radiation source. For example, as shown in FIG. 41, the sensing device 16 can include a laser switch 6090. In another embodiment, the sensing device 16 can include a visual camera to determine if a person is close to the shelf 6072. In another embodiment, the sensing device 16 can include sensors that are located on the floor near the storage area 6054.

Figure 42A:
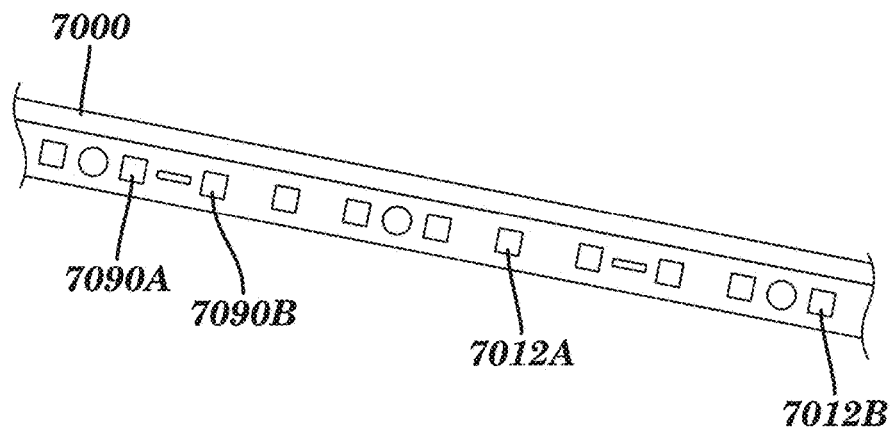

Turning now to FIG. 42A, a lamp 7000 according to an embodiment is shown. The lamp 7000 can be used in any of the embodiments discussed herein. The lamp 7000 can include any number of sources 7012A, 7012B, each of which can vary in wavelength, intensity, distribution of intensity over polar angles, and/or the like. The lamp 7000 can also include any number of electronic components 7090A, 7090B that are part of a power component 19 (FIG. 3) and used to deliver power to the sources 7012A, 7012B. Although it is not shown, the lamp 7000 can include fluorescent and visible light sensors, visible light sources, and/or the like. The visible light sources can be selected to prolong storage life for the set of items within the storage area and improve the presentation of the set of items. For example, the color of the visible light source can be selected to achieve a natural rendering of the set of items.

Figure 42B:
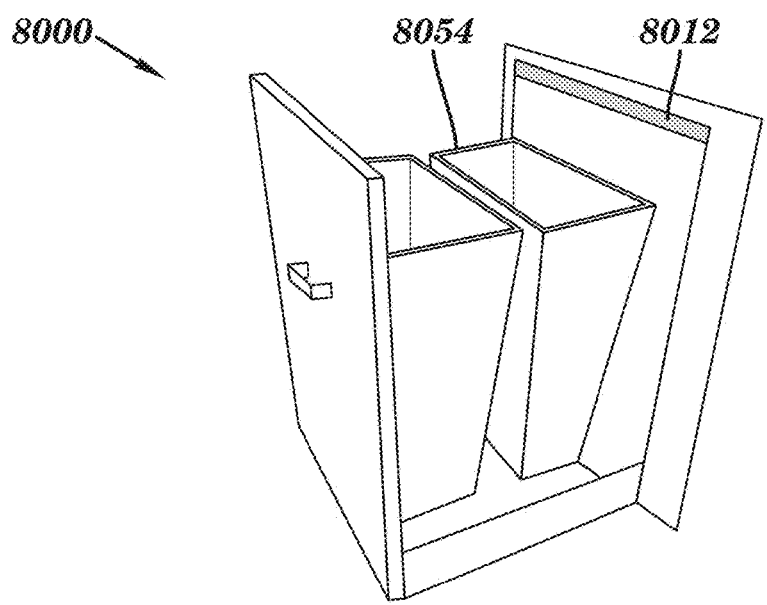
FIG. 42B shows an illustrative storage device according to an embodiment.

Turning now to FIG. 42B, a storage device 8000 according to an embodiment is shown. The storage device 8000 includes a set of trash containers 8054. In this embodiment, the smell/odor of the set of trash containers 8054 may need to be controlled. A set of ultraviolet radiation sources 8012 can be coupled with a photo-catalyst, as discussed herein, in order to eliminate any undesired smells and odors within the storage device 8000. In an embodiment, the storage device 8000 can also include a chemical means to control the presence of undesired smells, such as baking soda, and/or the like to deodorize the storage device 8000. Although the set of ultraviolet radiation sources 8012 are located at the top of the storage device 8000, it is understood that the set of ultraviolet radiation sources 8012 can be located anywhere within the storage device 8000. For example, the set of ultraviolet radiation sources 8012 can be positioned so that ultraviolet radiation is not directed towards a user. Furthermore, a power component 19 (FIG. 3) can turn off the set of ultraviolet radiation sources 8012 upon opening of the storage device 8000.

While shown and described herein as a method and system for managing a storage area, it is understood that aspects of the invention further provide various alternative embodiments. For example, in one embodiment, the invention provides a computer program fixed in at least one computer-readable medium, which when executed, enables a computer system to manage the storage area using a process described herein. To this extent, the computer-readable medium includes program code, such as the analysis program 30 (FIG. 1), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the analysis program 30 (FIG. 1), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for managing the storage area. In this case, the generating can include configuring a computer system, such as the computer system 20 (FIG. 1), to implement a method of managing the storage area as described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
a storage device configured to contain a set of produce items;
a set of ultraviolet radiation sources configured to generate ultraviolet radiation over a portion of the set of produce items;
a set of infrared radiation sources configured to generate infrared radiation over the set of produce items in order to excite a set of fluorescent signals from a set of microorganisms located on the set of produce items;
a set of sensing devices configured to monitor a set of current conditions of at least one of: the storage device or the set of produce items, wherein the set of current conditions includes a proximity of a user and the set of fluorescent signals; and a control system configured to control the infrared radiation generated by the set of infrared radiation sources in order to excite the set of fluorescent signals and control the set of ultraviolet radiation sources based on the set of current conditions.

2. The system of claim 1, wherein the set of ultraviolet radiation sources comprises a lamp with a plurality of ultraviolet light emitting diodes.

3. The system of claim 2, further comprising an ultraviolet transparent enclosure for enclosing the lamp.

4. The system of claim 2, wherein at least one ultraviolet light emitting diode in the plurality of ultraviolet light emitting diodes are configured to operate at a wavelength in the range of 280 nanometers to 300 nanometers.

5. The system of claim 2, wherein the plurality of ultraviolet light emitting diodes includes a first set of ultraviolet light emitting diodes operating at a first wavelength range and a first target intensity configured to prolong a storage life for the set of produce items and a second set of ultraviolet light emitting diodes operating at a second wavelength range and a second target intensity configured to suppress mildew and growth of bacteria, wherein radiation from the first set of ultraviolet light emitting diodes has an intensity variation of at most 50%.

6. The system of claim 1, wherein the set of sensing devices includes a set of fluorescent sensors configured to monitor the set of fluorescent signals from the set of produce items over a period of time.

7. The system of claim 6, further comprising a set of visible light sources, wherein at least one visible light source operates at a peak wavelength of approximately 430 nanometers and at least one visible light source operates at a peak wavelength of approximately 630 nanometers.

8. The system of claim 7, wherein the control system is configured to determine a presence of flavonoids in the set of produce items.

9. The system of claim 1, wherein the set of sensing devices includes a visual camera.

10. A storage device comprising:
a storage area including at least one shelf for holding at least one produce item;
a set of ultraviolet radiation sources configured to generate ultraviolet radiation into the storage area and over a portion of the set of produce items;
a set of infrared radiation sources configured to generate infrared radiation over the set of produce items in order to excite a set of fluorescent signals from a set of microorganisms located on the set of produce items;
a set of sensing devices configured to monitor a set of current conditions of at least one of: the storage device or the set of produce items, wherein the set of current conditions includes a proximity of a user and the set of fluorescent signals; and
a control system configured to control the infrared radiation generated by the set of infrared radiation sources in order to excite the set of fluorescent signals and control the set of ultraviolet radiation sources based on the set of current conditions.

11. The storage device of claim 10, wherein the set of ultraviolet radiation sources comprises a lamp with a plurality of ultraviolet light emitting diodes.

12. The storage device of claim 11, further comprising an ultraviolet transparent enclosure for enclosing the lamp.

13. The storage device of claim 11, wherein the plurality of ultraviolet light emitting diodes includes a first set of ultraviolet light emitting diodes operating at a first wavelength range and a first target intensity configured to prolong a storage life for the set of produce items and a second set of ultraviolet light emitting diodes operating at a second wavelength range and a second target intensity configured to suppress mildew and growth of bacteria, wherein radiation from the first set of ultraviolet light emitting diodes has an intensity variation of at most 50%.

14. The storage device of claim 10, wherein the set of sensing devices includes a set of fluorescent sensors configured to monitor the set of fluorescent signals from the set of produce items over a period of time.

15. The storage device of claim 14, further comprising a set of visible light sources, wherein at least one visible light source operates at a peak wavelength of approximately 430 nanometers and at least one visible light source operates at a peak wavelength of approximately 630 nanometers.

16. The storage device of claim 15, wherein the control system is configured to determine a presence of flavonoids in the set of produce items.

17. A storage device comprising:
a storage area including at least one shelf for holding at least one produce item;
a lamp located over the at least one shelf, the lamp including a set of ultraviolet radiation sources configured to generate ultraviolet radiation into the storage area and over a portion of the set of produce items;
a set of infrared radiation sources configured to generate infrared radiation over the set of produce items in order to excite a set of fluorescent signals from a set of microorganisms located on the set of produce items;
a set of sensing devices configured to monitor a set of current conditions of at least one of: the storage device or the set of produce items, wherein the set of current conditions includes a proximity of a user and the set of fluorescent signals; and
a control system configured to control the infrared radiation generated by the set of infrared radiation sources in order to excite the set of fluorescent signals and control the set of ultraviolet radiation sources based on the set of current conditions.

18. The storage device of claim 17, further comprising an ultraviolet transparent enclosure for enclosing the lamp.

19. The storage device of claim 17, wherein the set of sensing devices includes a set of fluorescent sensors configured to monitor the set of fluorescent signals from the set of produce items over a period of time.

20. The storage device of claim 19, further comprising a set of visible light sources, wherein at least one visible light source operates at a peak wavelength of approximately 430 nanometers and at least one visible light source operates at a peak wavelength of approximately 630 nanometers, wherein the control system is configured to determine a presence of flavonoids in the set of produce items.

* * * * *